(12) United States Patent
Littman et al.

(10) Patent No.: US 12,103,946 B2
(45) Date of Patent: Oct. 1, 2024

(54) STEROID COMPOUNDS AS TREG MODULATORS AND USES THEREOF

(71) Applicant: New York University, New York, NY (US)

(72) Inventors: Dan R. Littman, New York, NY (US); Jun R. Huh, Newton, MA (US); Michael Fischbach, Stanford, CA (US)

(73) Assignee: New York University, New York, NY (US)

(*) Notice: Subject to any disclaimer, the term of this patent is extended or adjusted under 35 U.S.C. 154(b) by 765 days.

(21) Appl. No.: 17/284,227

(22) PCT Filed: Oct. 8, 2019

(86) PCT No.: PCT/US2019/055176
§ 371 (c)(1),
(2) Date: Apr. 9, 2021

(87) PCT Pub. No.: WO2020/076815
PCT Pub. Date: Apr. 16, 2020

(65) Prior Publication Data
US 2021/0347811 A1 Nov. 11, 2021

Related U.S. Application Data

(60) Provisional application No. 62/742,680, filed on Oct. 8, 2018.

(51) Int. Cl.
| | | |
|---|---|---|
| *A61K 31/575* | (2006.01) | |
| *A61P 37/00* | (2006.01) | |
| *C07J 9/00* | (2006.01) | |
| *C12N 5/0783* | (2010.01) | |

(52) U.S. Cl.
CPC .......... *C07J 9/005* (2013.01); *A61P 37/00* (2018.01); *C12N 5/0637* (2013.01); *A61K 31/575* (2013.01); *C12N 2501/15* (2013.01); *C12N 2501/2302* (2013.01); *C12N 2501/999* (2013.01)

(58) Field of Classification Search
CPC ..................................................... C07J 9/005
See application file for complete search history.

(56) References Cited

U.S. PATENT DOCUMENTS 9,522,155 B2   12/2016 Moriarty et al.

FOREIGN PATENT DOCUMENTS

WO   2015/161078 A1   10/2015
WO   2018/102606 A1   6/2018

OTHER PUBLICATIONS

Pols et al. PLoS One 12(5): e0176715, pp. 1-16 (Year: 2017).*
Normanton et al. einstein(São Paulo) 2013;11(2):237-246 (Year: 2013).*
Schmidt et al. PLoS One. Feb. 17, 2016;11(2):e0148474, pp. 1-31 (Year: 2016).*
Hu et al. J Immunol. May 15, 2008;180(10):6544-6552 (Year: 2010).*
Miltenyi Biotec—T cell isolation kit, accessed Jan. 2, 2024 (Year: 2024).*
Earle et al Clinical Immunology 115 (2005) 3-9 (Year: 2005).*
Lee, E., et al., Ursodeoxycholic acid attenuates experimental autoimmune arthritis by targeting Th17 and inducing pAMPK and transcriptional corepressor SMILE, Immunology Letters, 2017, vol. 188, pp. 1-8.
Pubchem CID No. 159621, Chol-4-en-24-oic acid, 3-oxo-, Aug. 8, 2005, pp. 1-11.
Katona, B.W., et al., Synthesis, Characterization, and Receptor Interaction Profiles of Enantiomeric Bile Acids J. Med. Chem., 2007, vol. 50, pp. 6048-6058.
Earle, K.E., et al., In vitro expanded human CD4+CH25+ regulatory T cells suppress effector T cell proliferation, Clinical Immunology, 2005, vol. 115, pp. 3-9.

* cited by examiner

Primary Examiner — Craig D Ricci
(74) Attorney, Agent, or Firm — Hodgson Russ LLP

(57) ABSTRACT

Steroid compounds are disclosed that have a formula represented by the following: (I) and wherein $R^1$, $R^2$, $R^{3a}$, $R^{3b}$, $R^{4a}$, $R^{4b}$, $R^5$, $R^{6a}$, $R^{6b}$, $R^7$, $R^8$, and n are as described herein. The compounds may be prepared as pharmaceutical compositions, and may be used for promoting differentiation of T regulatory (Treg) lymphocytes, and for the prevention and treatment of a variety of conditions in mammals including humans, including by way of non-limiting example, inflammatory conditions, autoimmune disorders, and graft-versus-host disease.

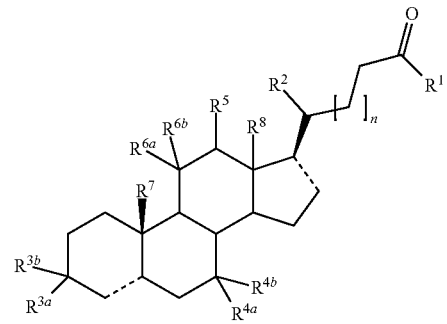

5 Claims, 59 Drawing Sheets
Specification includes a Sequence Listing.

d e

STEROID COMPOUNDS AS TREG MODULATORS AND USES THEREOF

CROSS REFERENCE TO RELATED APPLICATIONS

This application claims priority to U.S. Provisional Application No. 62/742,680, filed on Oct. 8, 2018, the disclosure of which is incorporated by reference herein.

STATEMENT REGARDING FEDERALLY SPONSORED RESEARCH

This invention was made with government support under contract no. DK110559 and AI080885 awarded by the National Institutes of Health. The government has certain rights in the invention.

FIELD OF THE INVENTION

The present invention relates to steroid compounds capable of promoting differentiation of T regulatory (Treg) lymphocytes and suppressing inflammatory Th17 cells. More particularly, the invention relates to methods for promoting differentiation of Treg lymphocytes using steroid compounds.

BACKGROUND OF THE INVENTION

Treg cells are long-lived cells that suppress excessive or uncontrolled immune responses in vivo in a dominant and antigen-specific manner. Genetic mutations in the forkhead box protein 3 (FoxP3), a key transcription factor required for differentiation of Treg cells, lead to severe autoimmunity. Indeed, research in a variety of animal models has demonstrated that Tregs can be used to treat many auto-inflammatory diseases such as type 1 diabetes, inflammatory bowel disease, systemic lupus erythematosus, multiple sclerosis (MS), rheumatoid arthritis, and auto-immune gastritis. Tang et al. (2012, J Molec Cell Biol 4:11-21). Treg cell therapy has, moreover, been shown to be efficacious in controlling alloimmune responses in the context of GVHD, as well as organ and cell transplantation in animal models. In light of the above, Treg cell therapy has been proposed as a way to control autoimmune diseases such as type 1 diabetes and MS and to treat GVHD in humans. Such an approach is envisioned to involve expansion of patient-derived and/or umbilical cord blood-derived Treg cells in vitro, after which the expanded Treg population is re-introduced into a patient in need thereof.

Pro-inflammatory Th17 cells are a subset of T helper cells. These cells are capable of mediating an inflammatory reaction. Th17 cells produce interleukin 17 (IL-17) and are thought to play a key role in autoimmune diseases and in microbial infections.

Bile acids are cholesterol-derived natural surfactants, produced in the liver and secreted into the duodenum. They are critical for lipid digestion, antibacterial defense and glucose metabolism ((1). While 95% of bile acids are re-absorbed through the terminal ileum of the small intestine and recirculated to the liver, hundreds of milligrams of bile acids are subject to bacterial-mediated transformation and become secondary bile acids with unique chemical structures and biological activities (2, 3). In the healthy human gut, the concentrations of secondary bile acids are in the hundreds of micromolar range (2, 4). While some bile acids disrupt cellular membranes due to their hydrophobic nature (5), other bile acids protect the gut epithelium (6) and confer resistance to infection with invasive pathogens such as *Clostridium difficile* (7). In addition, bile acids were shown to influence gut-associated inflammation, suggesting their potential to regulate gut mucosal immune cells (8, 9). The immune-modulatory effects of bile acids have mostly been studied in the context of innate immunity (10-12).

Although a recent study reported the cytotoxic effects of bile acids on gut-residing T cells (13), whether they modulate T cell function directly has not been thoroughly examined. While bile acids have been shown to affect host metabolism, cancer progression and innate immunity, it is unknown whether bile acids affect the function of adaptive immune cells such as T cells expressing IL-17a (Th17 cells) and regulatory T cells (Tregs) that mediate inflammatory and anti-inflammatory responses, respectively.

Given the above, it is clinically important to devise ways to potentiate Treg differentiation and function and/or suppress Th17 cell function in controlling immune responses.

SUMMARY OF THE INVENTION

Steroid compounds described herein may be used to reduce symptoms associated with an autoimmune or inflammatory disorder. In a particular embodiment, steroid compounds described herein may be used in the context of organ or tissue transplantation, wherein complications due to graft-versus-host disease (GVHD) or host-mediated rejection of the transplant occur. Also encompassed herein, are compositions of steroid compounds, pharmaceutical compositions of steroid compounds, and assays and methods for using same to promote differentiation of Treg lymphocytes and/or suppress Th17 cell function.

The present invention provides methods for promoting differentiation of T regulatory (Treg) lymphocytes and/or suppress Th17 cell function, which comprises contacting naive CD4+ T lymphocytes with an effective amount of a compound according to formula I.

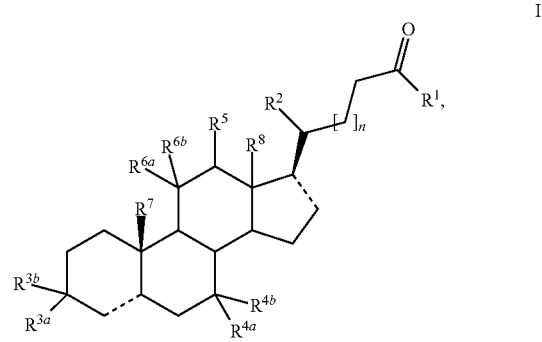

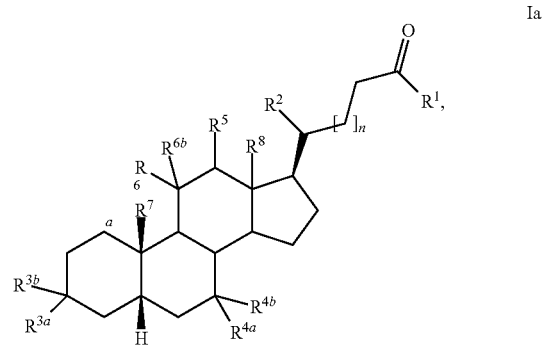

Ib
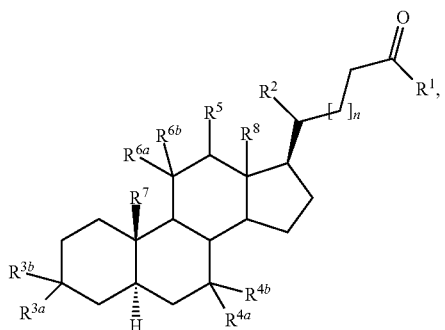

Ic
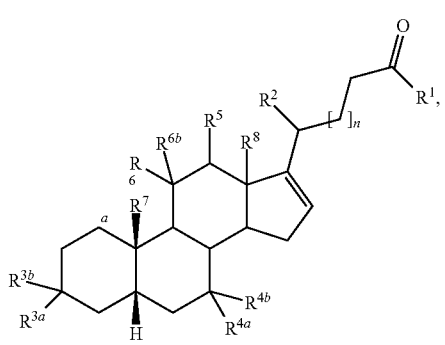

Id
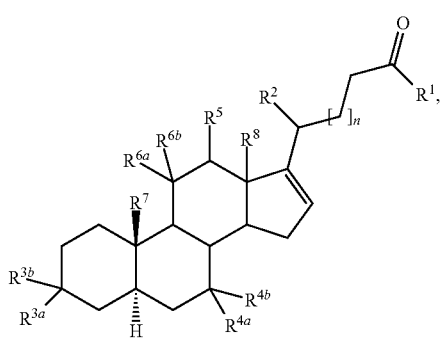

Ie
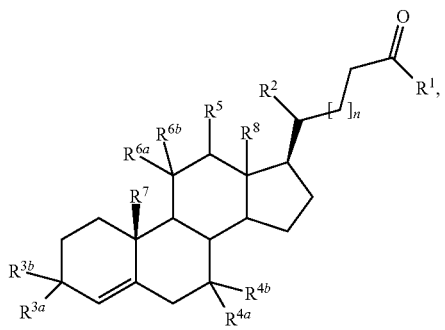

If
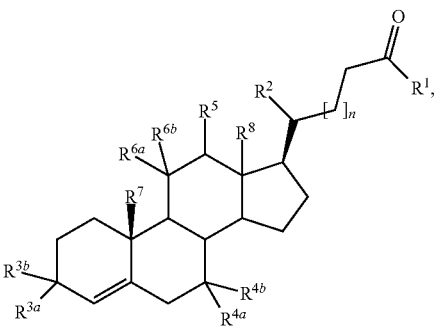

Ig
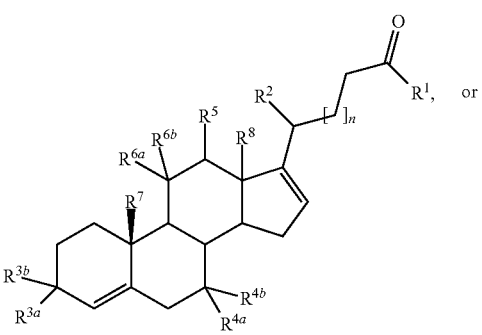

Ih
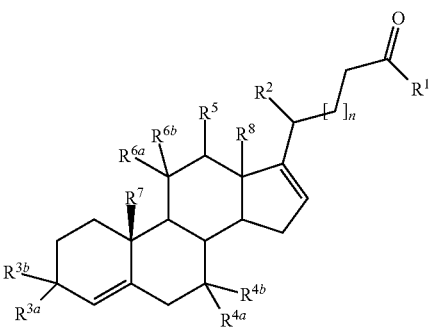

wherein:
R$^1$ is substituted or unsubstituted alkyl, substituted or unsubstituted hydroxyl, or substituted or unsubstituted amino;
R$^2$ is H, alkyl, or substituted or unsubstituted cycloalkyl;
R$^{3a}$ is —OH, —OC(O)R$^{3c}$, or —O—S(O)$_2$OH; R$^3$, is substituted or unsubstituted alkyl;
R$^{3b}$ is selected from H, substituted or unsubstituted alkyl, substituted or unsubstituted alkenyl, or substituted or unsubstituted alkynyl;
or R$^{3a}$ and R$^{3b}$ are joined to form an oxo (=O) group;
each R$^{4a}$, R$^{4b}$, R$^5$, R$^{6a}$, and R$^{6b}$ is independently H, OH, substituted or unsubstituted amino, or substituted or unsubstituted alkyl;
or each R$^{4a}$ and R$^{4b}$ or R$^{6a}$ and R$^{6b}$ are joined to form an oxo (=O) group;
R$^7$ is H or substituted or unsubstituted alkyl;
R$^8$ is H or substituted or unsubstituted alkyl;
and n is independently 0, 1, 2, 3, 4, 5, or 6;
and each dotted bond is independently a single or a double bond;
or a pharmaceutically acceptable salt, solvate, hydrate, prodrug, or stereoisomer, thereof,
or a combination thereof.

In one embodiment, with respect to the compounds of formula I, the compound is other than ursodeoxycholic acid or tauroursodeoxycholic acid.

In a particular embodiment, with respect to the compounds of formula I-IId, each of $R^{4a}$, and $R^{4b}$ is H.

In a particular embodiment, with respect to the compounds of formula I, the compound is according to formula IIIa-XVIId.

In a further aspect, the present invention provides compositions of compounds according to formula I wherein $R^7$ is H.

In a further aspect, the present invention provides compositions of compounds according to formula I wherein $R^{3b}$ is other than H.

In one particular embodiment, with respect to the method, of the compound is according to formula I-XVIId.

In a further aspect, the present invention provides pharmaceutical compositions comprising a compound according to formula I and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect, a method is presented for treating a mammal susceptible to or afflicted with a condition from among those listed herein, and particularly, such condition as may be associated with excessive or uncontrolled immune responses and/or insufficient Treg responses. Autoimmune and auto-inflammatory conditions typify conditions wherein promoting Treg differentiation and/or activity would be beneficial. Such conditions include, without limitation, type 1 diabetes, MS (and the animal model thereof, EAE), inflammatory bowel disease, systemic lupus erythematosus, rheumatoid arthritis (and the animal model thereof, CIA), psoriasis, uveitis, and auto-immune gastritis. Methods for treating a mammal who is the recipient of an organ or tissue transplant to treat or prevent GVHD or host-mediated rejection of the organ or tissue transplant are also envisioned herein.

Other objects and advantages will become apparent to those skilled in the art from a consideration of the ensuing detailed description.

BRIEF DESCRIPTION OF THE FIGURES

For a fuller understanding of the nature and objects of the disclosure, reference should be made to the following detailed description taken in conjunction with the accompanying figures.

Figure 5:
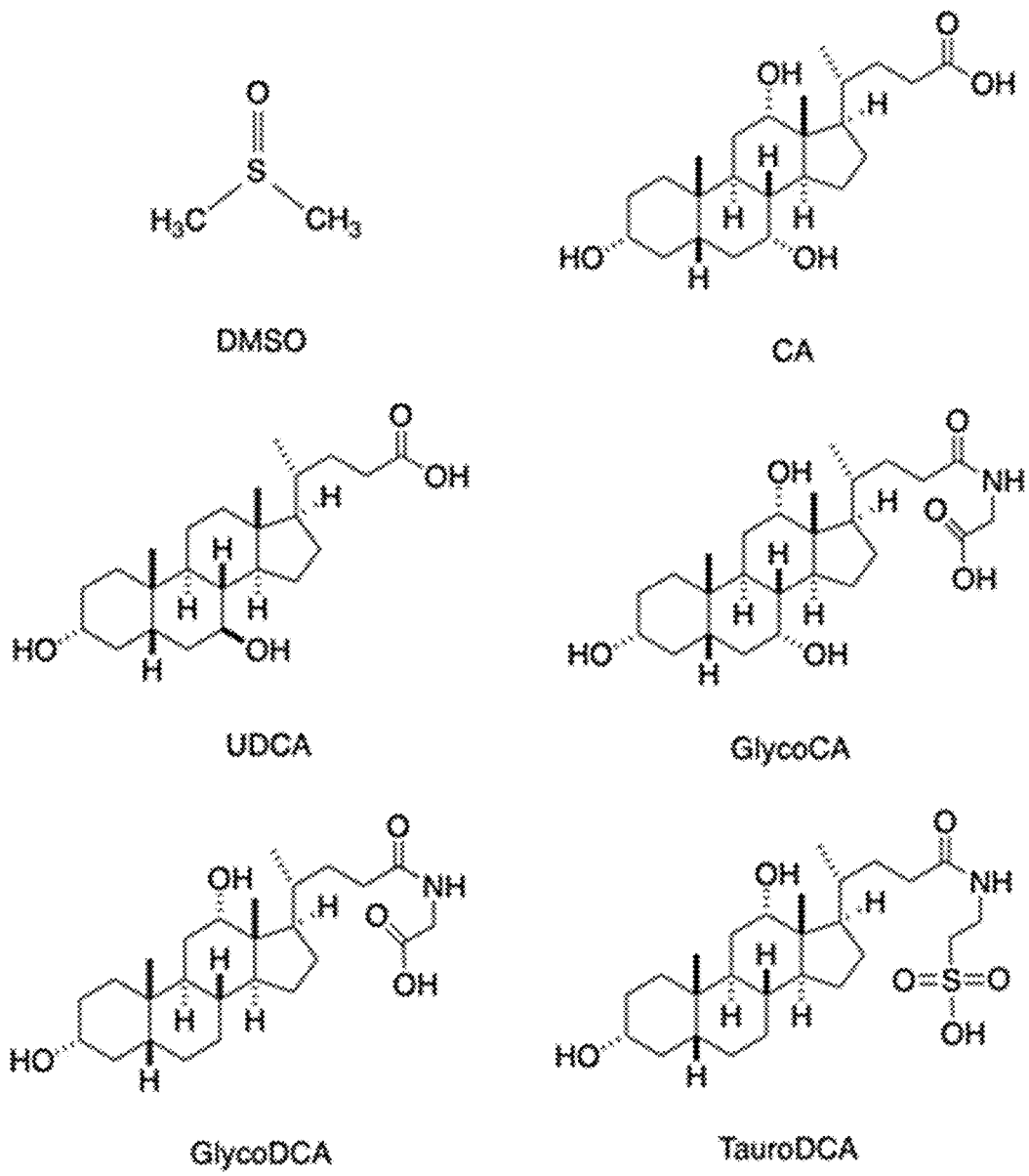
Figure 5:
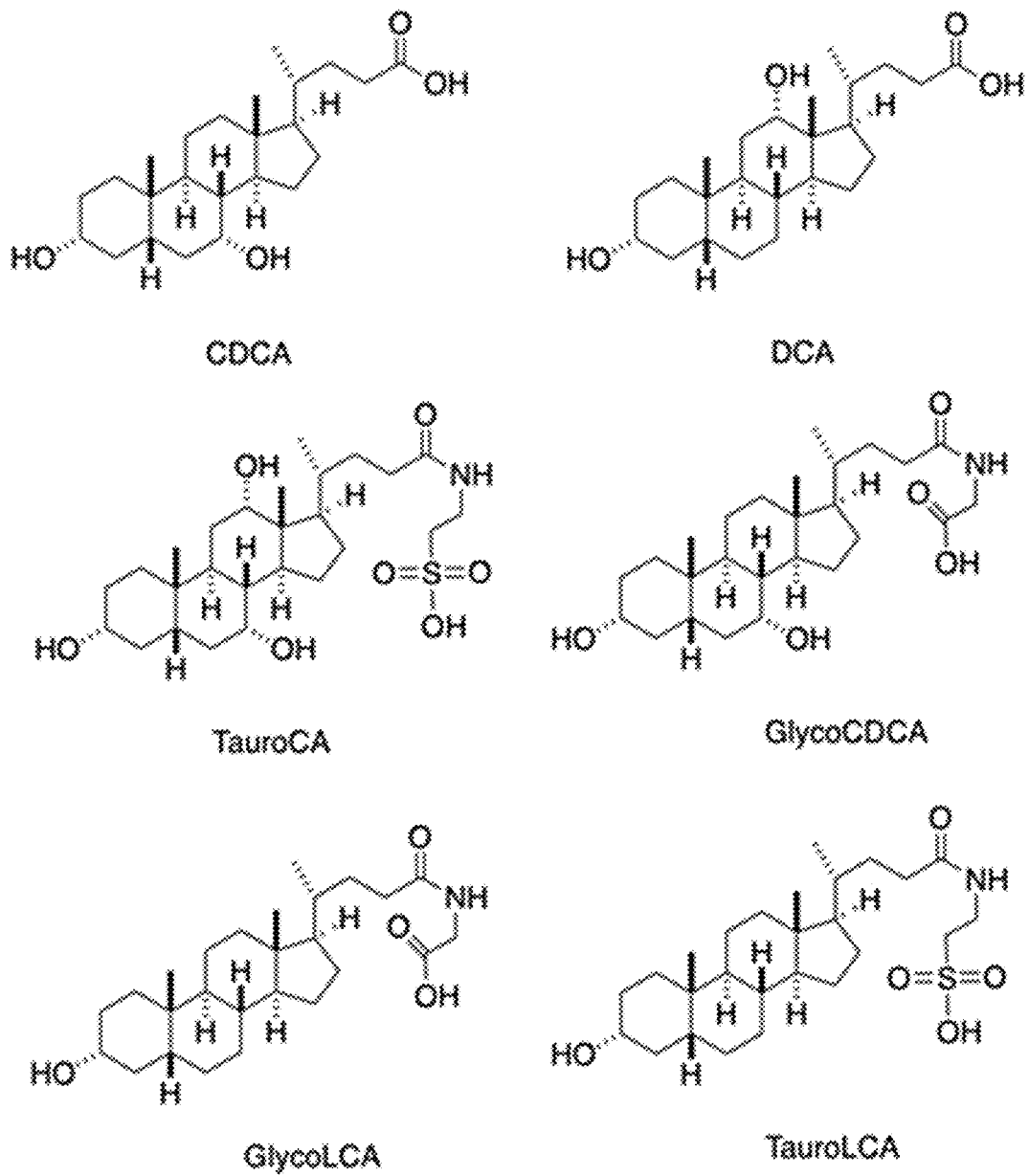
Figure 5:
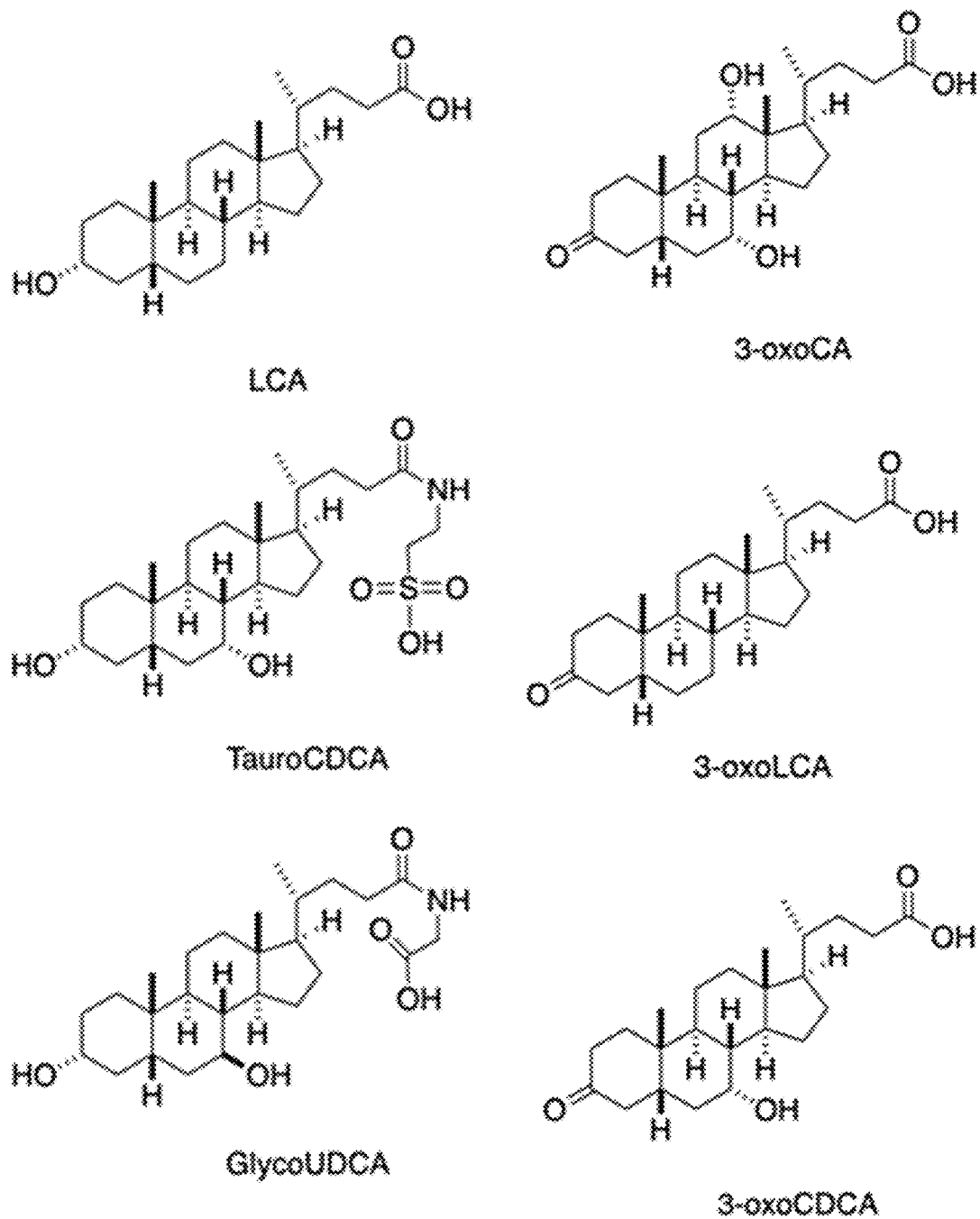
Figure 5:
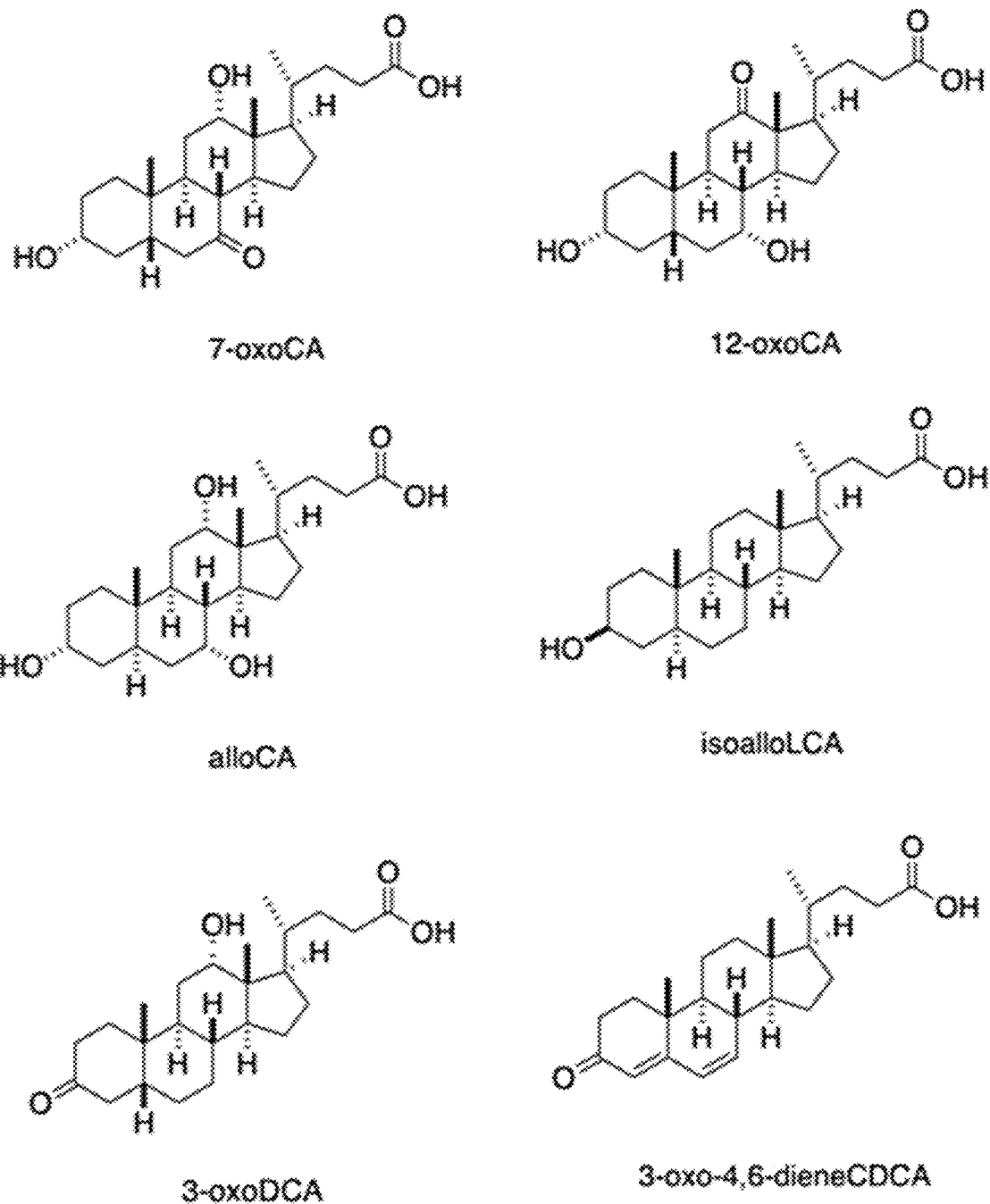
Figure 5:
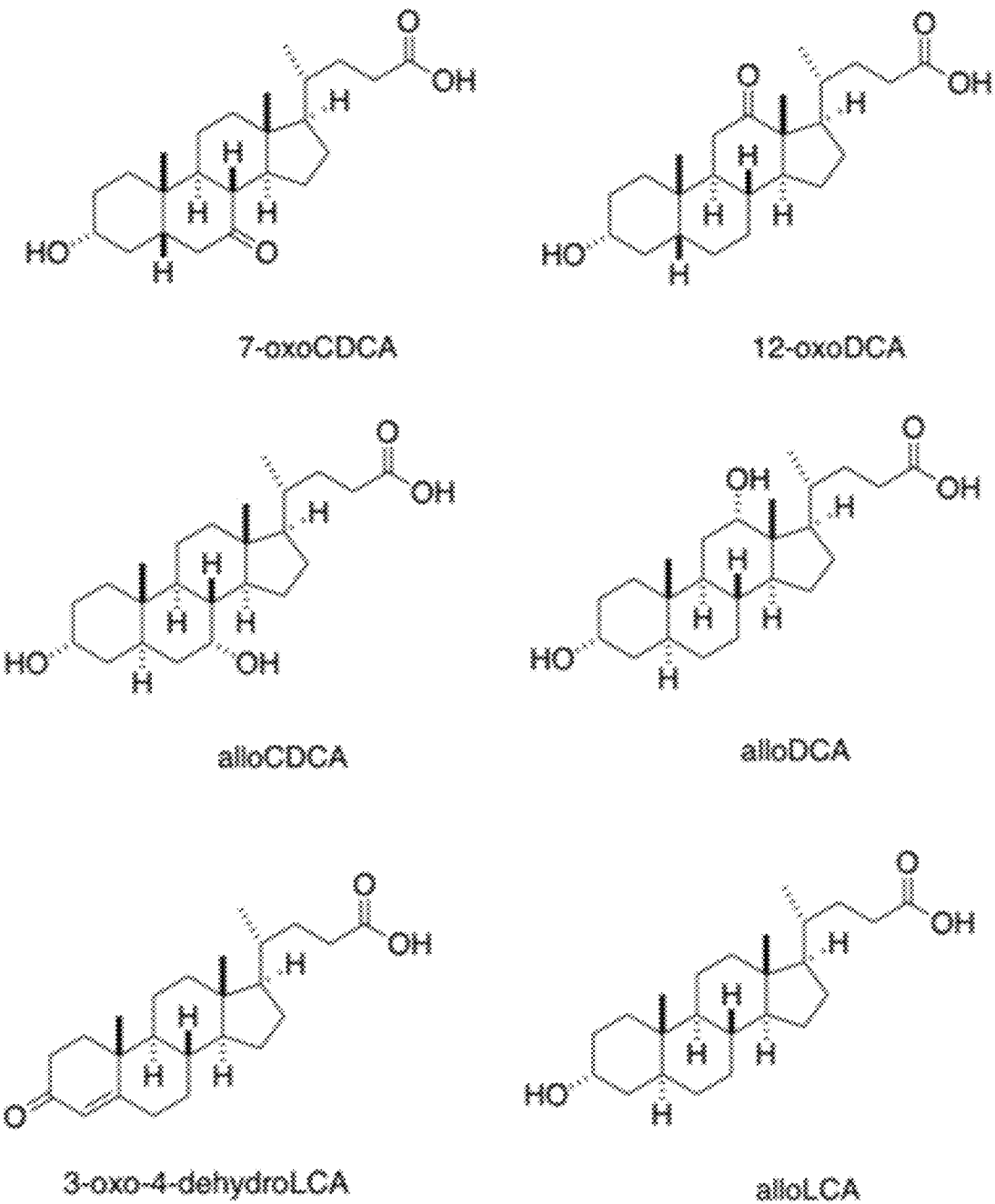

FIG. 5 shows chemical structures of bile acid derivatives used for T cell differentiation assay.

Figure 6:
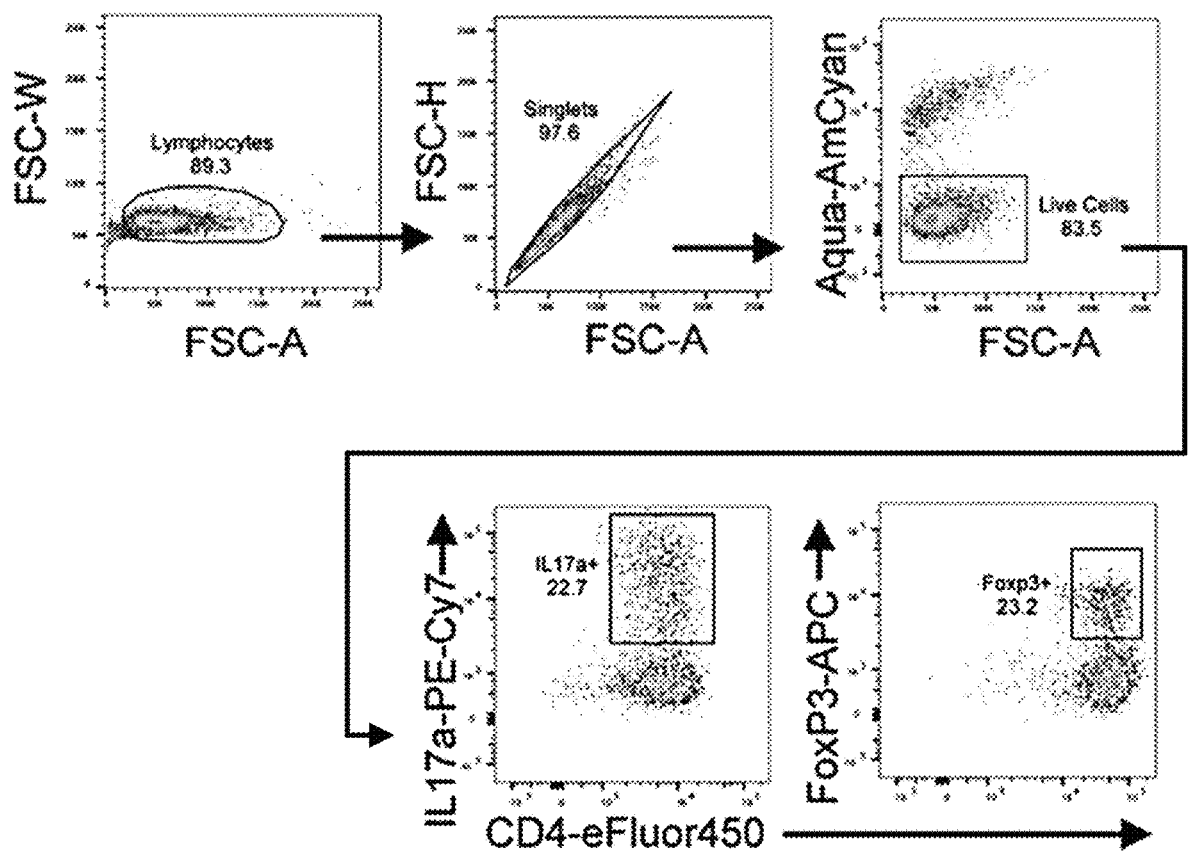
Figure 6:
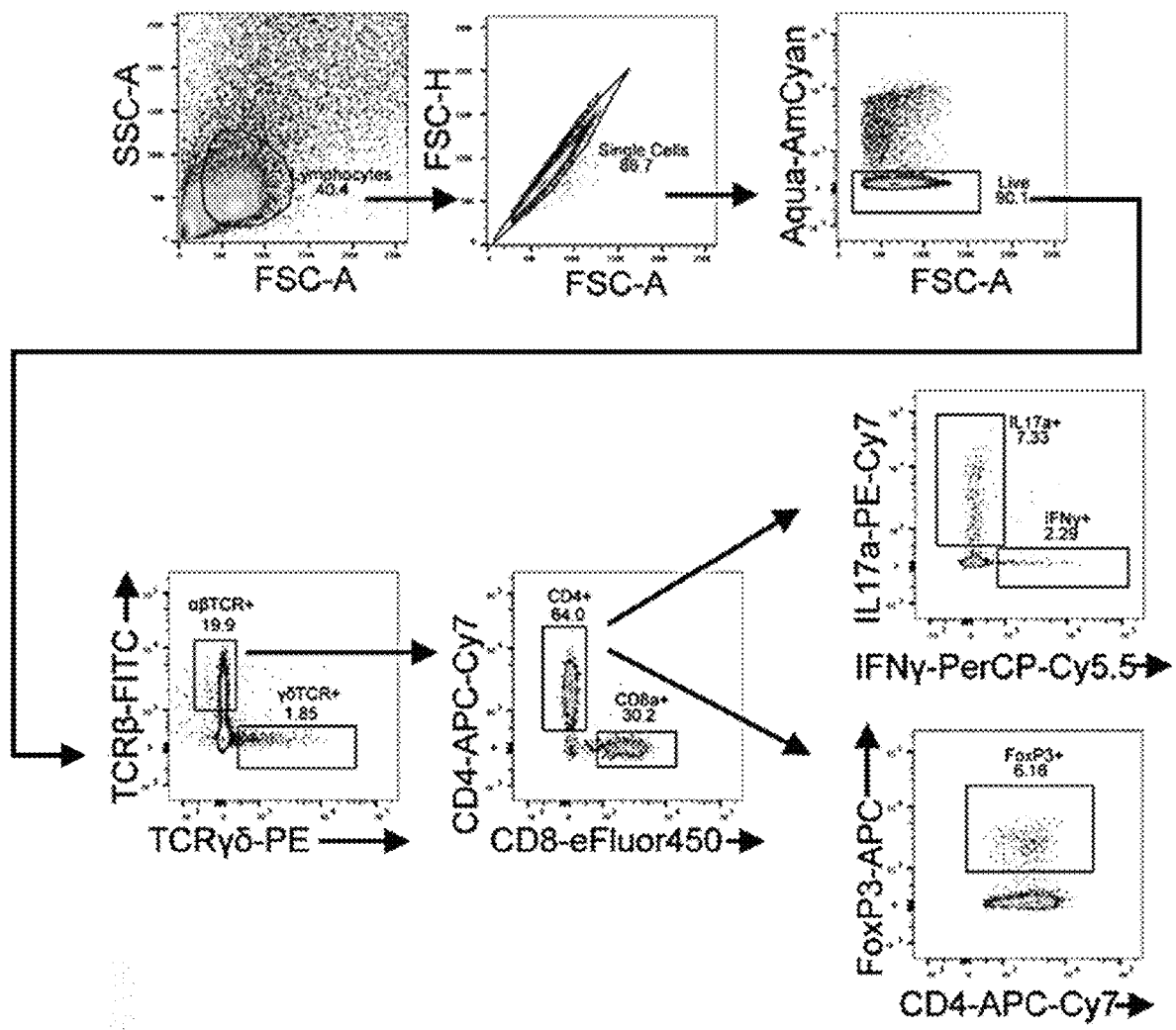
Figure 6:
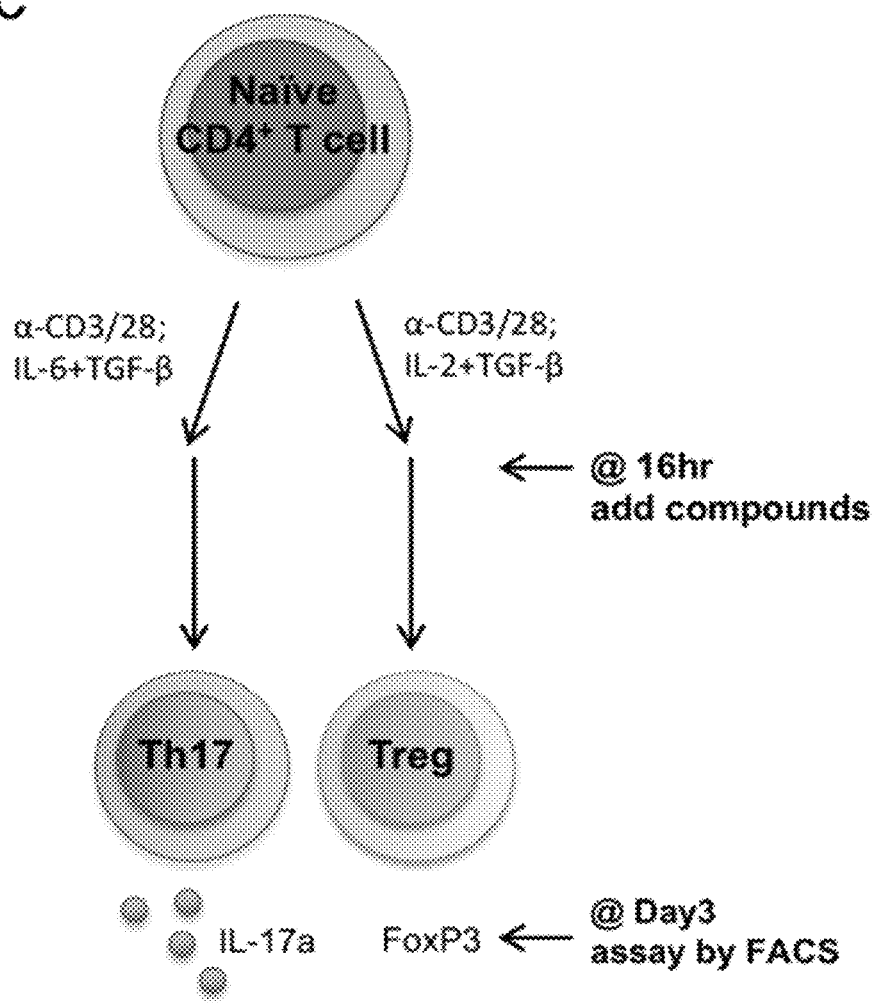
Figure 6:
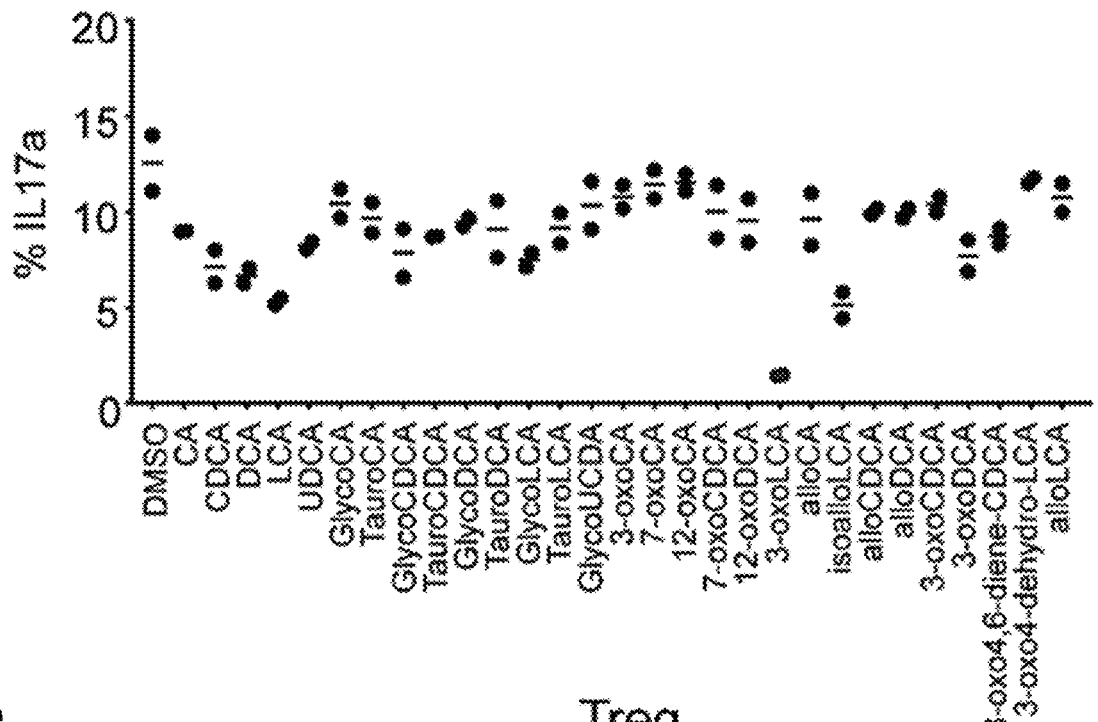
Figure 6:
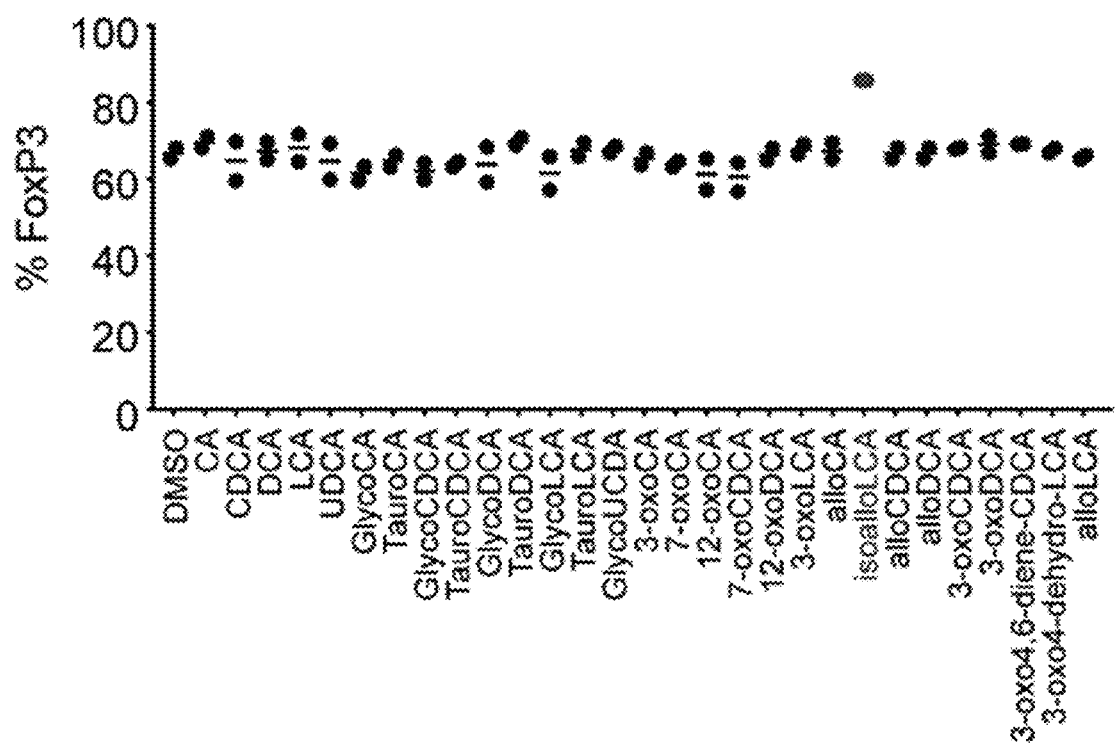

FIG. 6 shows 3-oxoLCA and isoalloLCA affect Th17 and Treg differentiation. a and b, Gating strategy for the flow cytometric analyses of in vitro cultured T cells (a) and in vivo derived cells from the lamina propria (b). c, Schematic of the screening procedure. d and e, Naïve CD4+ T cells isolated from B6 mice (n=2) were cultured under Th17 (IL-6=10 ng/ml; TGF-β=0.5 ng/ml) (d) and Treg (IL-2=100 U/ml; TGF-β=0.1 ng/ml) (e) polarization conditions for 3 days. DMSO or various bile acids at 20 μM concentration were added to the cell cultures on day 1. n, number of biologically independent samples. Data are shown as the mean.

Figure 7:
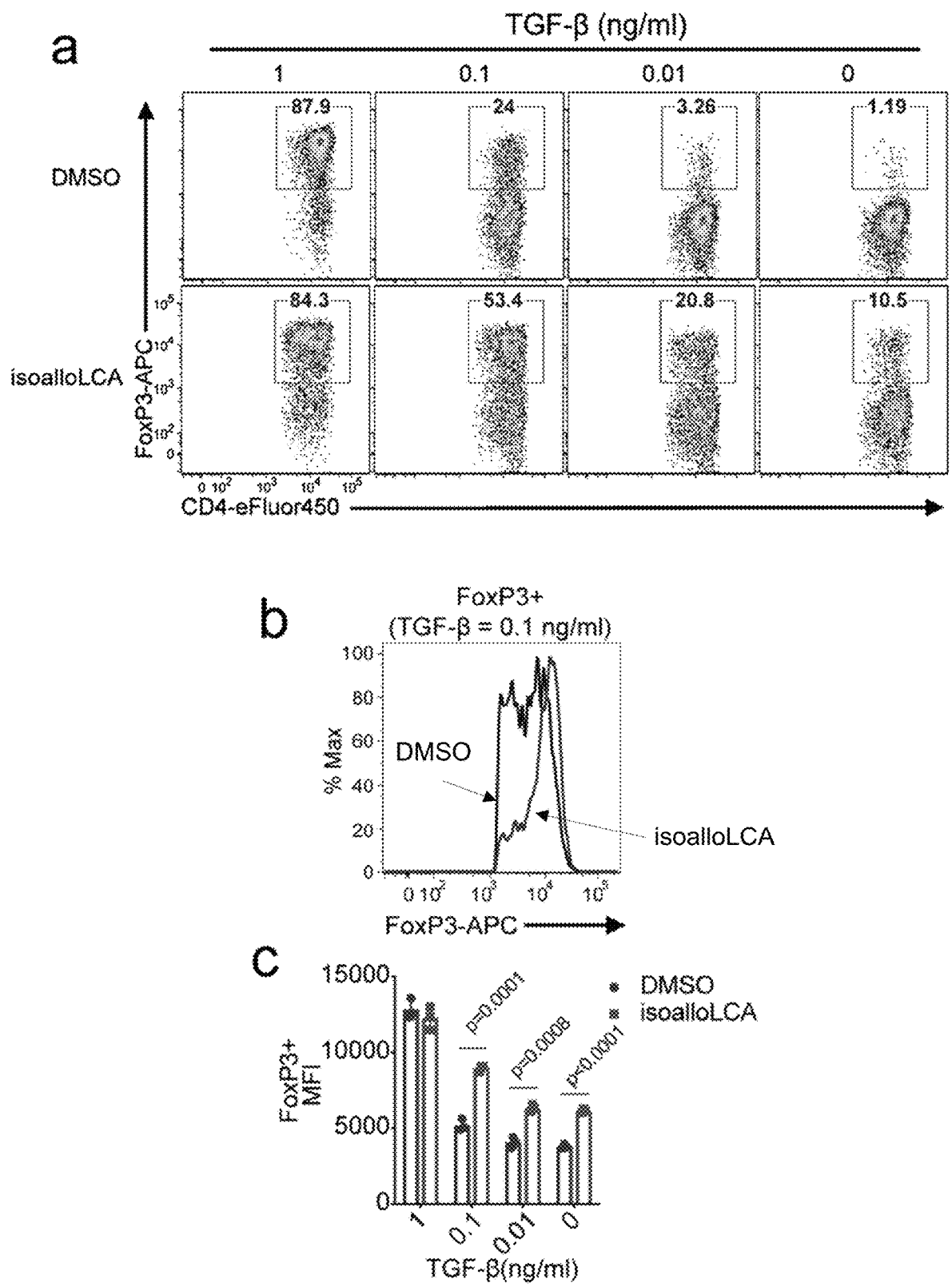
Figure 7:
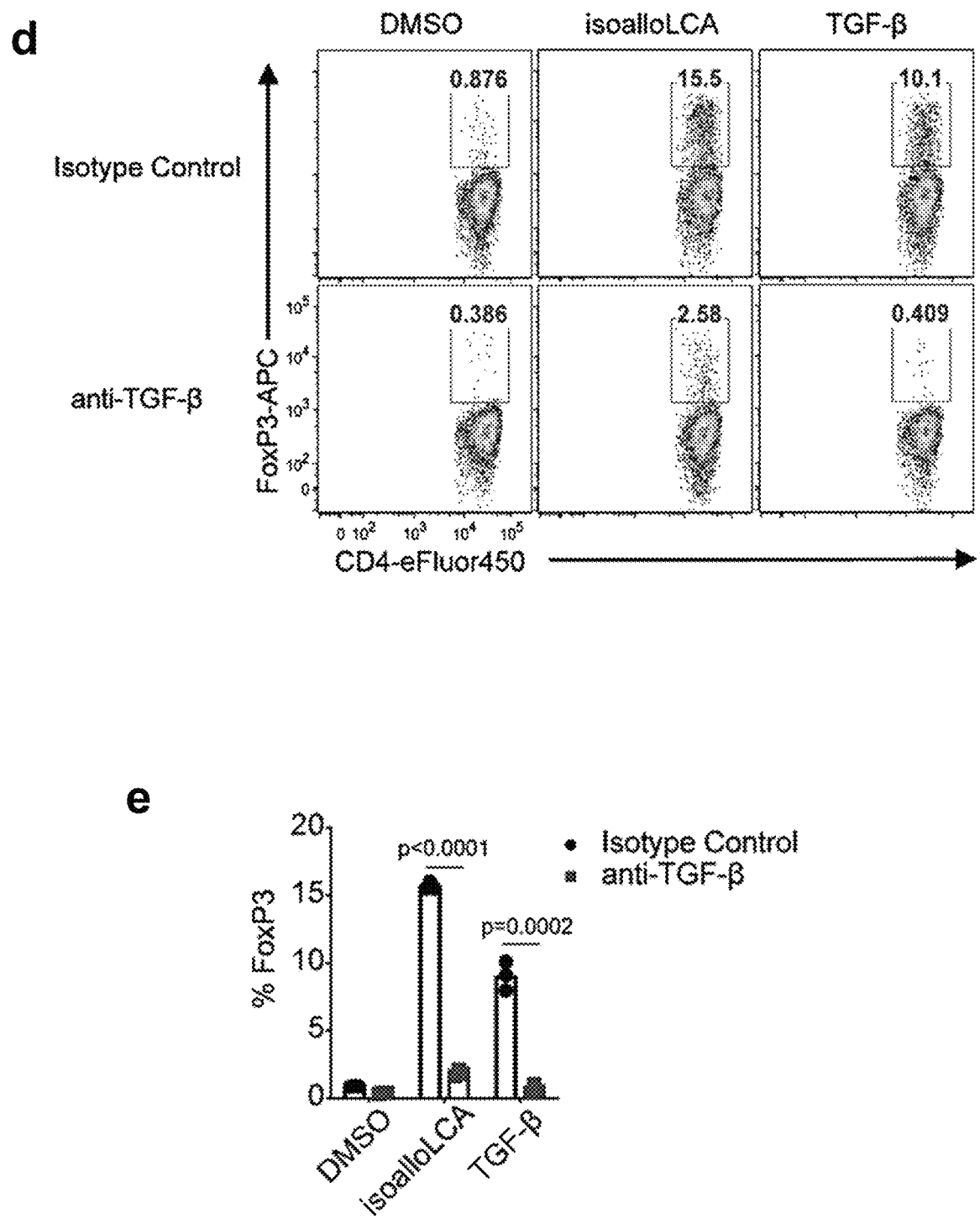
Figure 7:
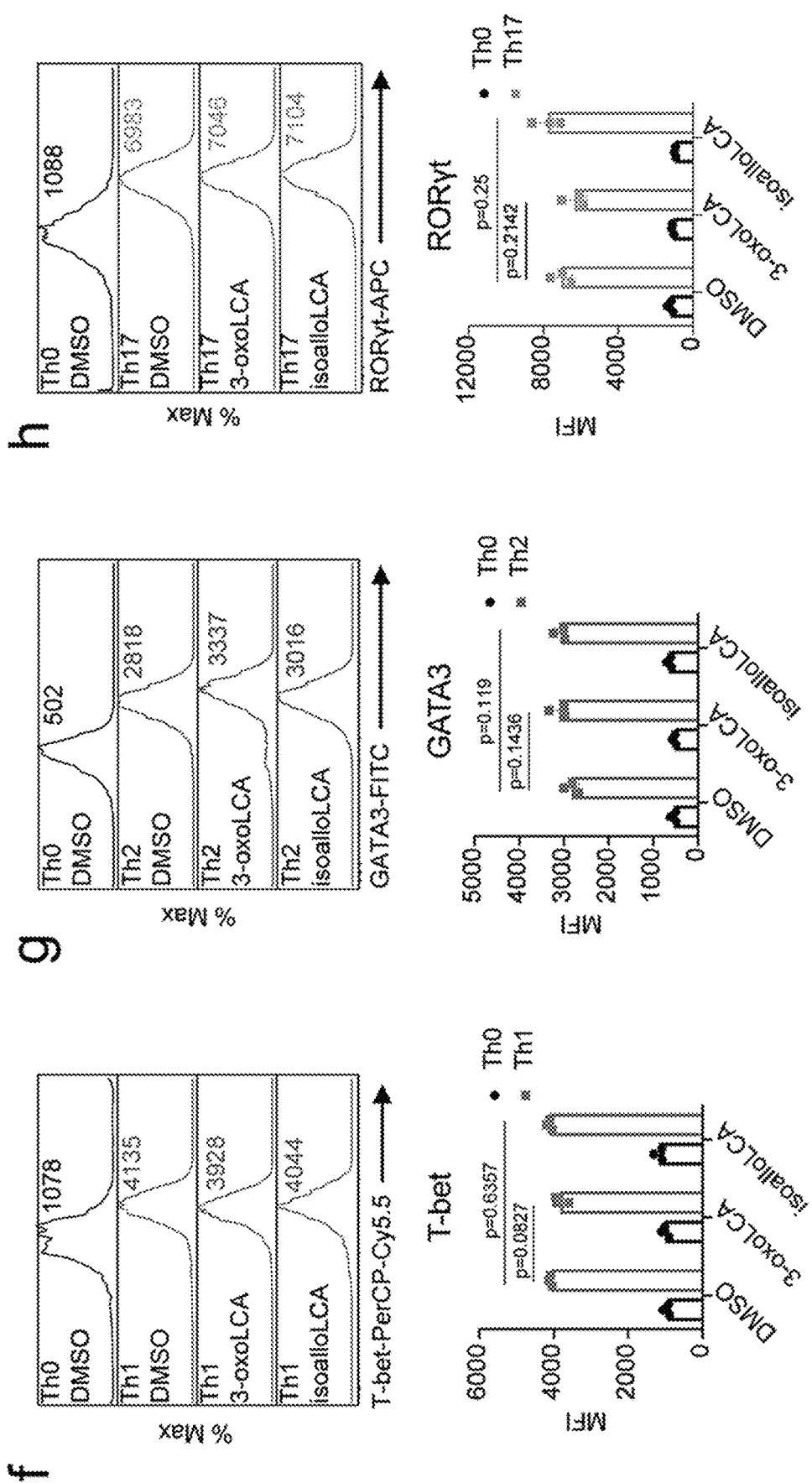

FIG. 7 shows isoalloLCA-induced Treg expansion requires TGF-β. a-c, Flow cytometry and histogram of CD4+ T cells, cultured for 3 days with different amounts of TGF-β (1, 0.1, 0.01 or 0 ng/ml) and IL-2 (100 U/ml) in the presence of DMSO or isoalloLCA (20 μM) and intracellularly stained for FoxP3 (n=3/group). d and e, Flow cytometry of CD4+ T cells, cultured for 3 days in the presence of DMSO, isoalloLCA (20 μM) or TGF-β (0.05 ng/ml). In addition, anti-TGF-β antibody (10 μg/ml, 1D11) or isotype control were added to the culture (n=3/group). f-h, 3-oxoLCA and isoalloLCA do not affect key transcription factor expression. T cells were cultured under Th0, Th1, Th2 or Th17 conditions, in the presence of DMSO, 3-oxoLCA (20 μM) or isoalloLCA (20 μM). T cell lineage determining transcription factors such as T-bet, GATA3 or RORγt were intracellularly stained (n=3/group). MFI denotes mean fluorescence intensity. n, number of biologically independent samples. Data are shown as the mean±standard deviation by unpaired t-test with 2-tailed p-value.

Figure 8:
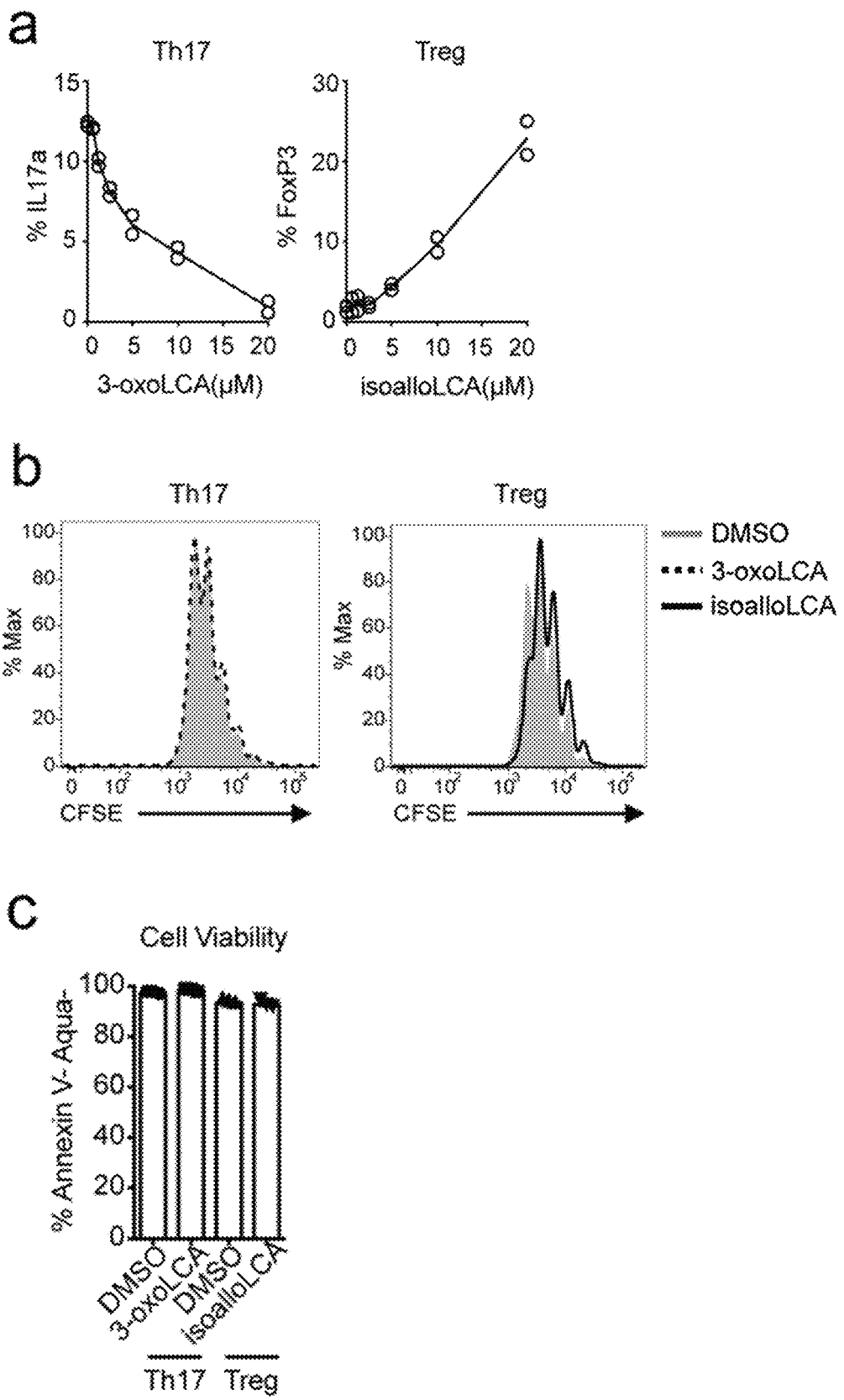
Figure 8:
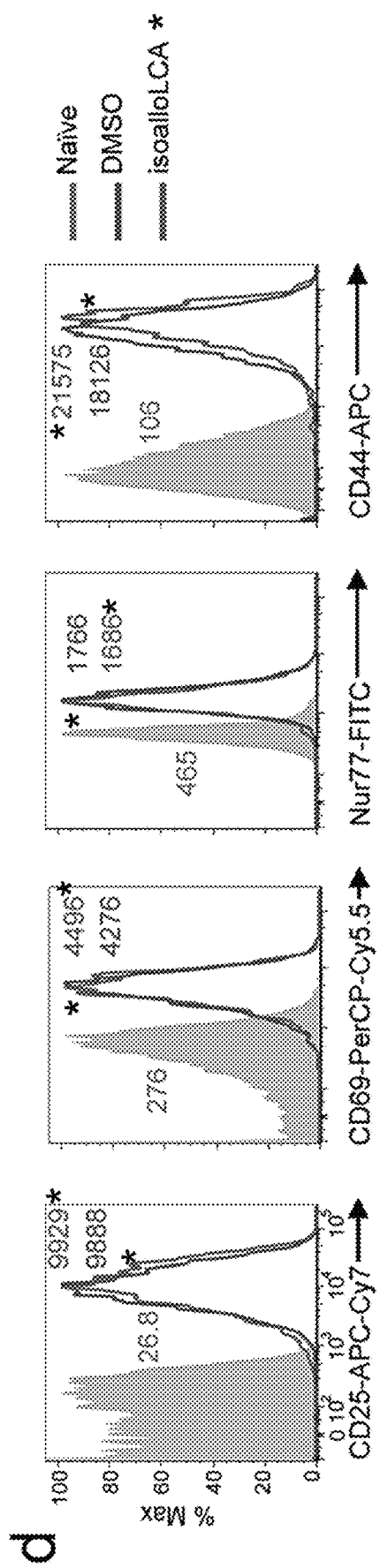
Figure 8:
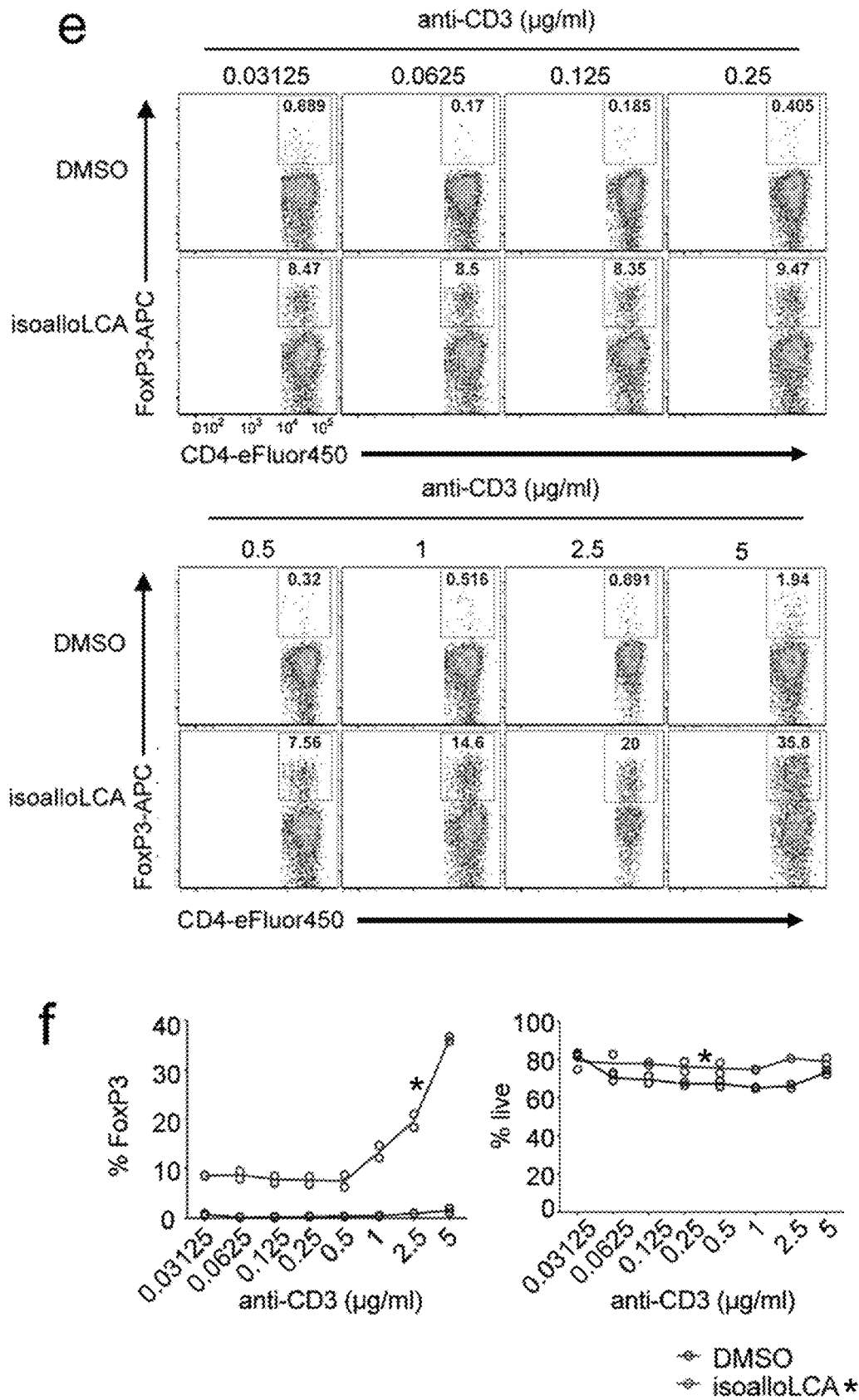

FIG. 8 shows Effects of isoalloLCA on FoxP3 expression require strong TCR stimulation. a, 3-oxoLCA and isoalloLCA demonstrate dose-dependent effects on Th17 cell and Treg differentiation, respectively (n=2). A low concentration of TGF-β (0.01 ng/ml) was used for Treg culture. b-d, 3-oxoLCA and isoalloLCA do not significantly affect cell proliferation, cell viability, or T cell activation. b, Naïve CD4+ T cells were labeled with a cell proliferation dye CFSE and cultured for 3 days in the presence of DMSO, 3-oxoLCA or isoalloLCA under Th17 or Treg polarization conditions. c, Live cell percentages at the end of the 3-day culture were determined based on both Annexin V and fixable live/dead staining (n=3/group). d, Both DMSO and isoalloLCA treatment lead to comparable levels of expression of CD25, CD69, Nur77 and CD44. Naïve CD4+ T cells were used as a negative control. e and f, T cells were cultured with different concentrations of anti-CD3 antibody, in the presence of DMSO or isoalloLCA (20 μM). Representative FACS plots of CD4+ T cells cultured for 3 days and stained intracellularly for FoxP3 (e). Quantification of FoxP3+ and viable T cells after 3-day culture (f) (n=2/group). n, number of biologically independent samples. Data are representative of two independent experiments (b, d). Data in (c) are shown as the mean±standard deviation.

Figure 9:
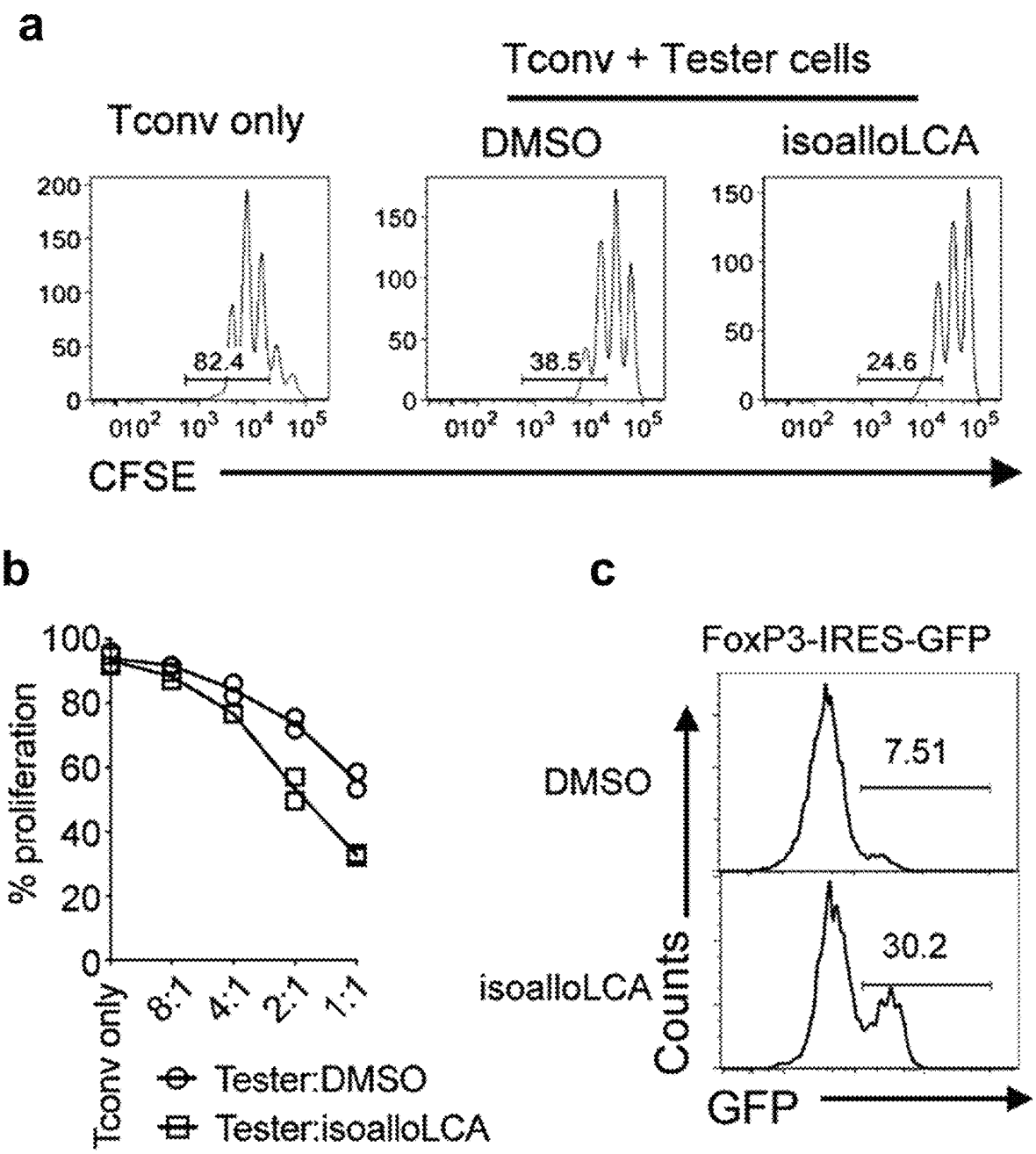
Figure 9:
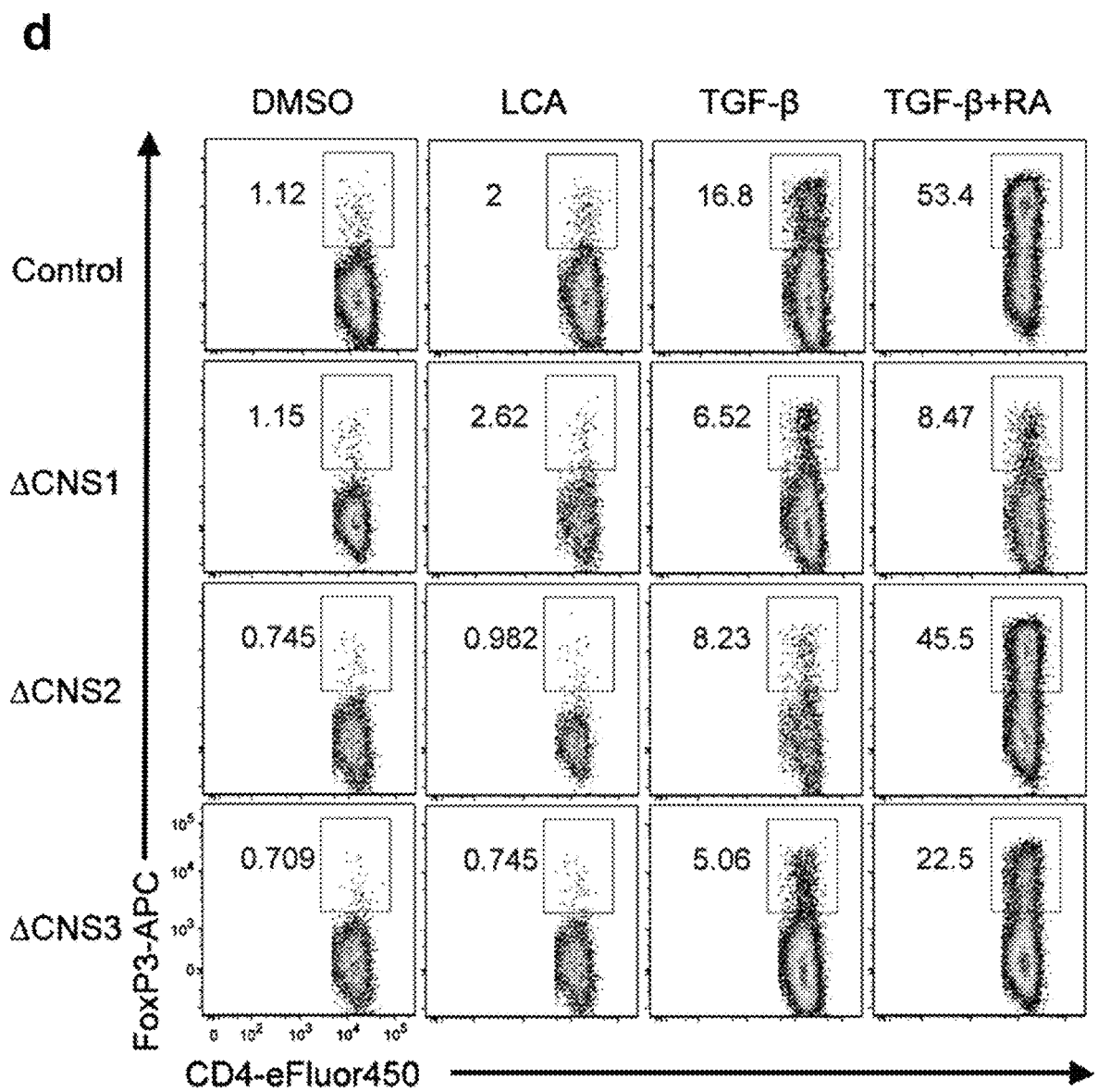
Figure 9:
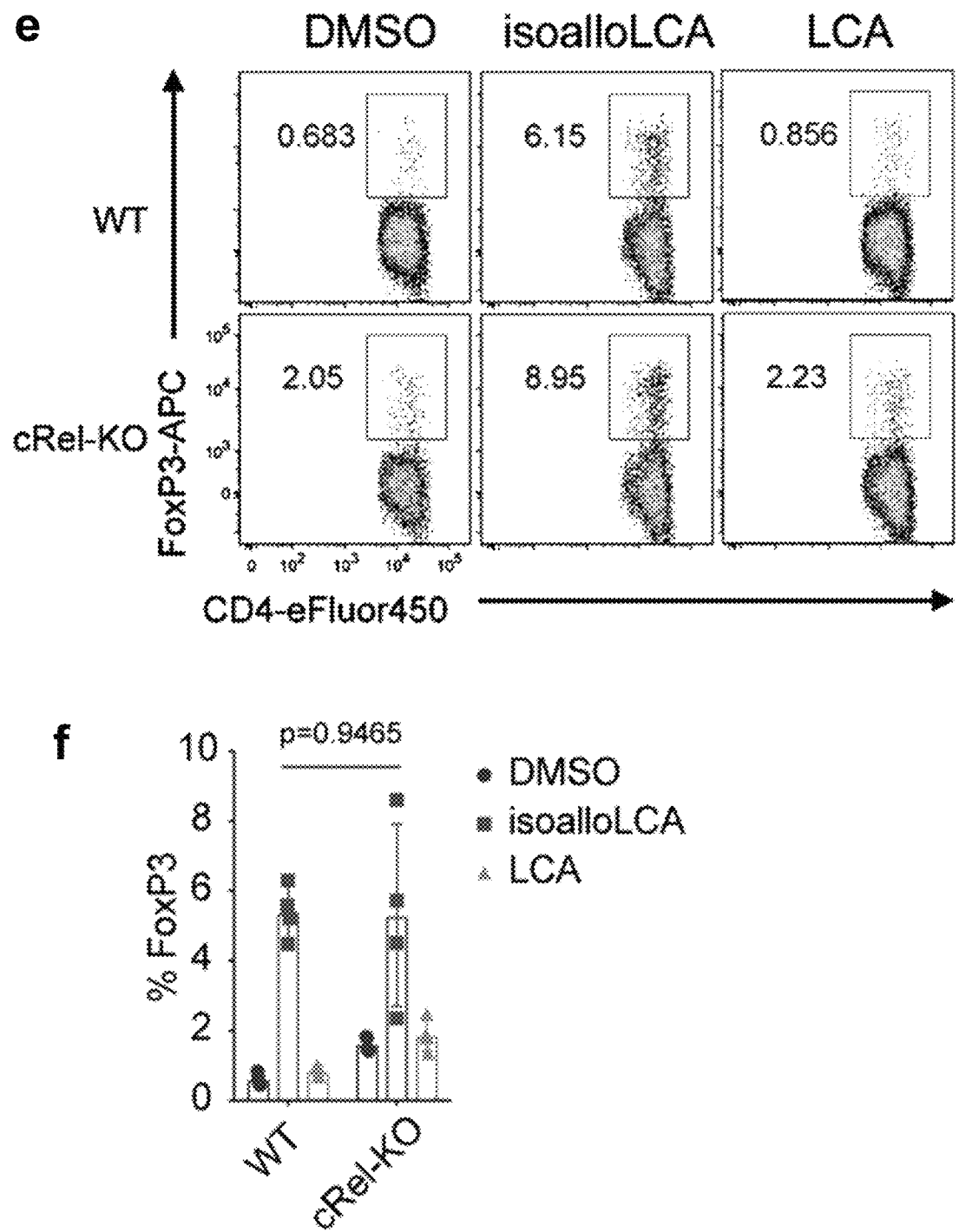
Figure 9:
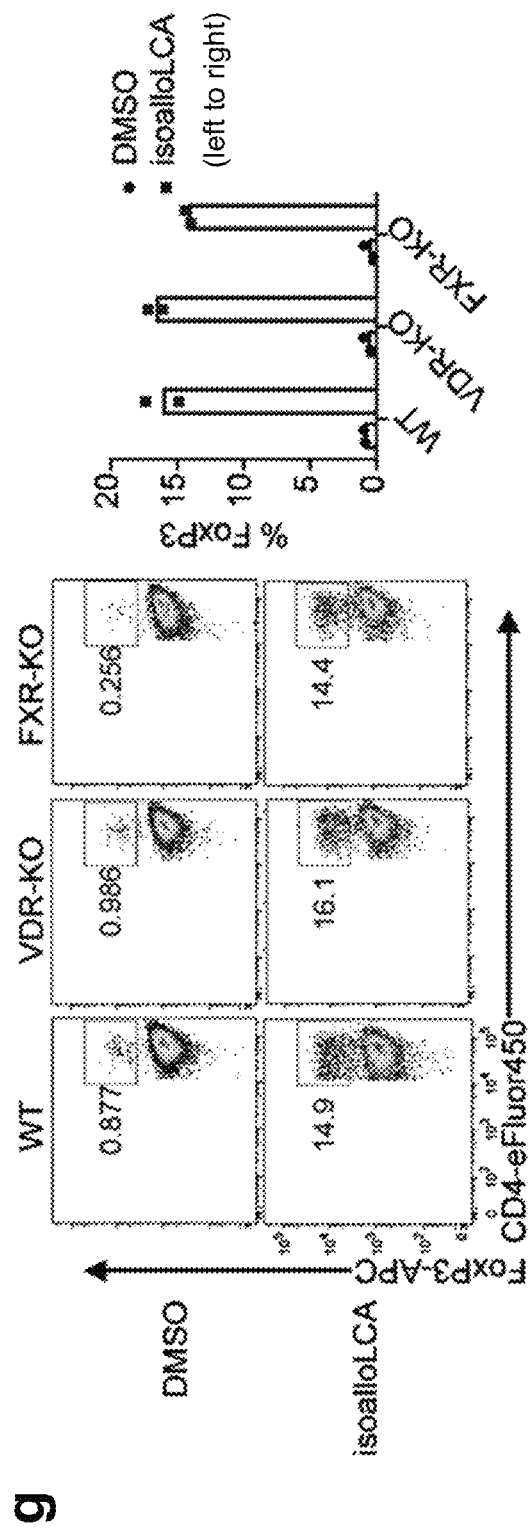
Figure 9:
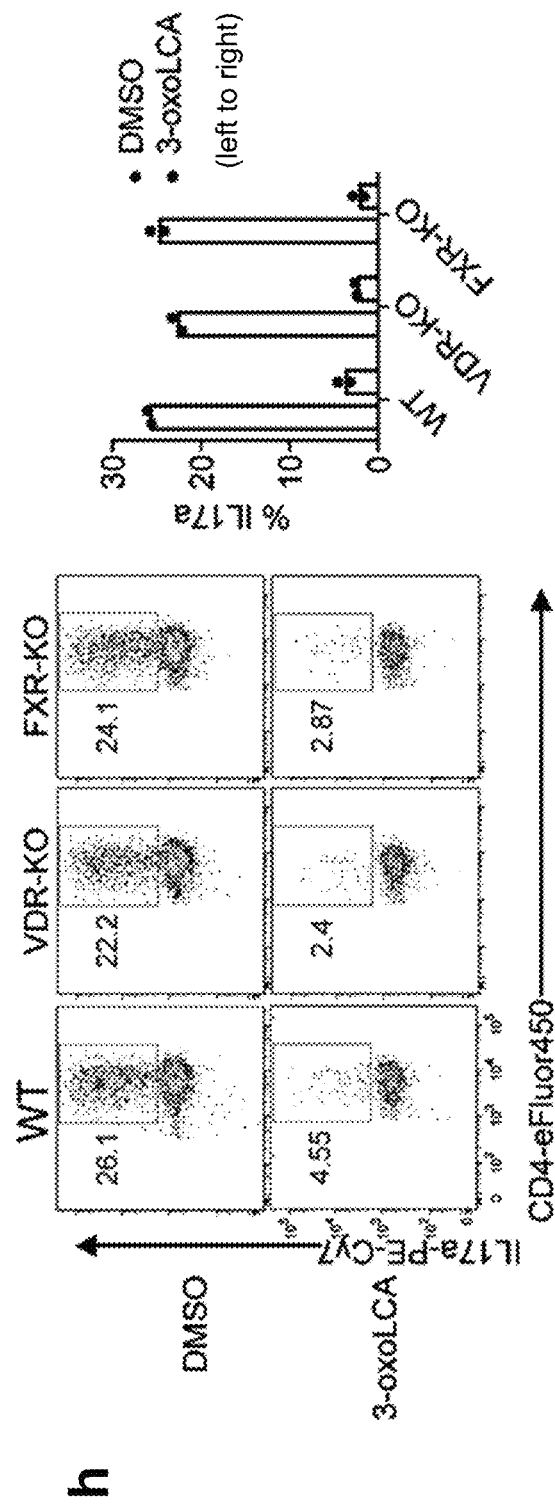
Figure 9:
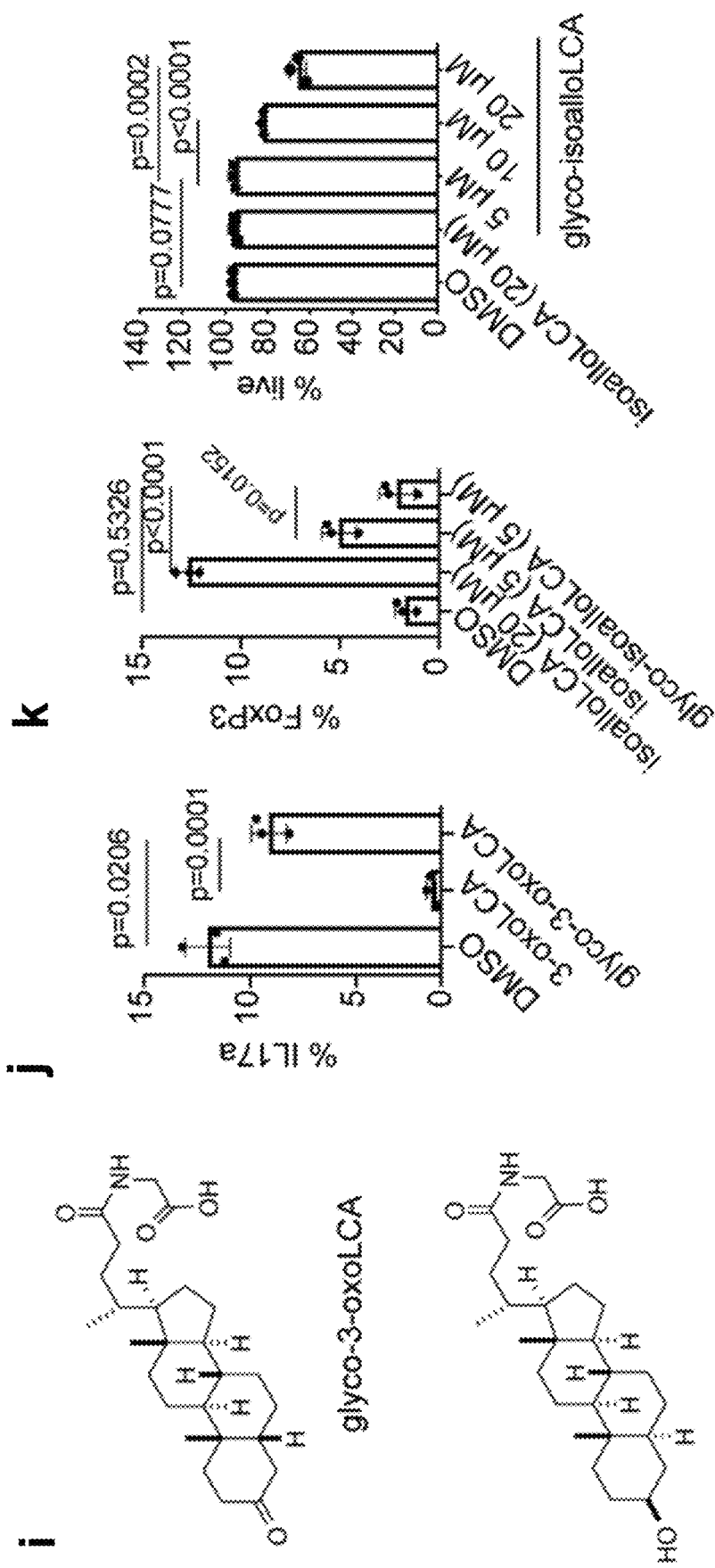

FIG. 9 shows cRel, VDR and FXR are dispensable for isoalloLCA-dependent induction of FoxP3. a and b, In vitro suppression assay. CD4+ effector T cells were labeled with CFSE and mixed with DMSO- or isoalloLCA-treated Treg cells at different ratios of Tconv: Tester cells (n=2/group). c, Expression of GFP in DMSO- or isoalloLCA-treated T cells cultured with anti-CD3/28, IL-2 and TGF-β (0.01 ng/ml). Naïve CD4+ T cells were isolated from FoxP3-IRES-GFP mice. d, Flow cytometry of CD4+ T cells stained intracellularly for FoxP3. Naïve CD4+ T cells isolated from WT, CNS1, CNS2 or CNS3 knockout mice (n=3/group) were cultured with anti-CD3/28 and IL-2, LCA (20 μM), TGF-β (0.05 ng/ml) and additional retinoic acid (RA; 1 ng/ml). e and f, Flow cytometry (e) and its quantification (f) of CD4+ T cells stained intracellularly for FoxP3. Naïve CD4+ T cells were isolated from WT control mice or cRel-KO mice (n=4/group) and cultured with anti-CD3/28 and IL-2 in the presence of DMSO, isoalloLCA (20 μM) or LCA (20 μM). g and h, Naïve CD4+ T cells isolated from WT control, VDR knockout or FXR knockout (n=mice/group) were cultured with anti-CD3/28 and IL-2 (g) or anti-CD3/28, IL-6 and TGF-β (h) for 3 days in the presence of DMSO, isoalloLCA (20 μM), or 3-oxoLCA (20 μM). Representative FACS plots of T cells intracellularly stained for FoxP3 or IL-17a. i, Chemical structures of glycine conjugated 3-oxoLCA (glyco-3-oxoLCA) and isoalloLCA (glyco-isoalloLCA). j and k, Quantifications of Th17 (j) and Treg (k) differentiation in vitro. T cells were cultured with anti-CD3/28, IL-6 and TGF-β (j) or anti-CD3/28 and IL-2 (k) in the presence of DMSO, 3-oxoLCA (20 μM), glyco-3-oxoLCA (20 μM), isoalloLCA (5 or 20 μM) or glyco-isoalloLCA (5, 10, or 20 μM). Glyco-isoalloLCA exhibited enhanced cytotoxicity at 10 or 20 μM compared to isoalloLCA (n=3/group). n, number of biologically independent samples. Data are representative of two independent experiments (c, d). Data are shown as the mean±standard deviation by unpaired t-test with 2-tailed p-value.

Figure 10:
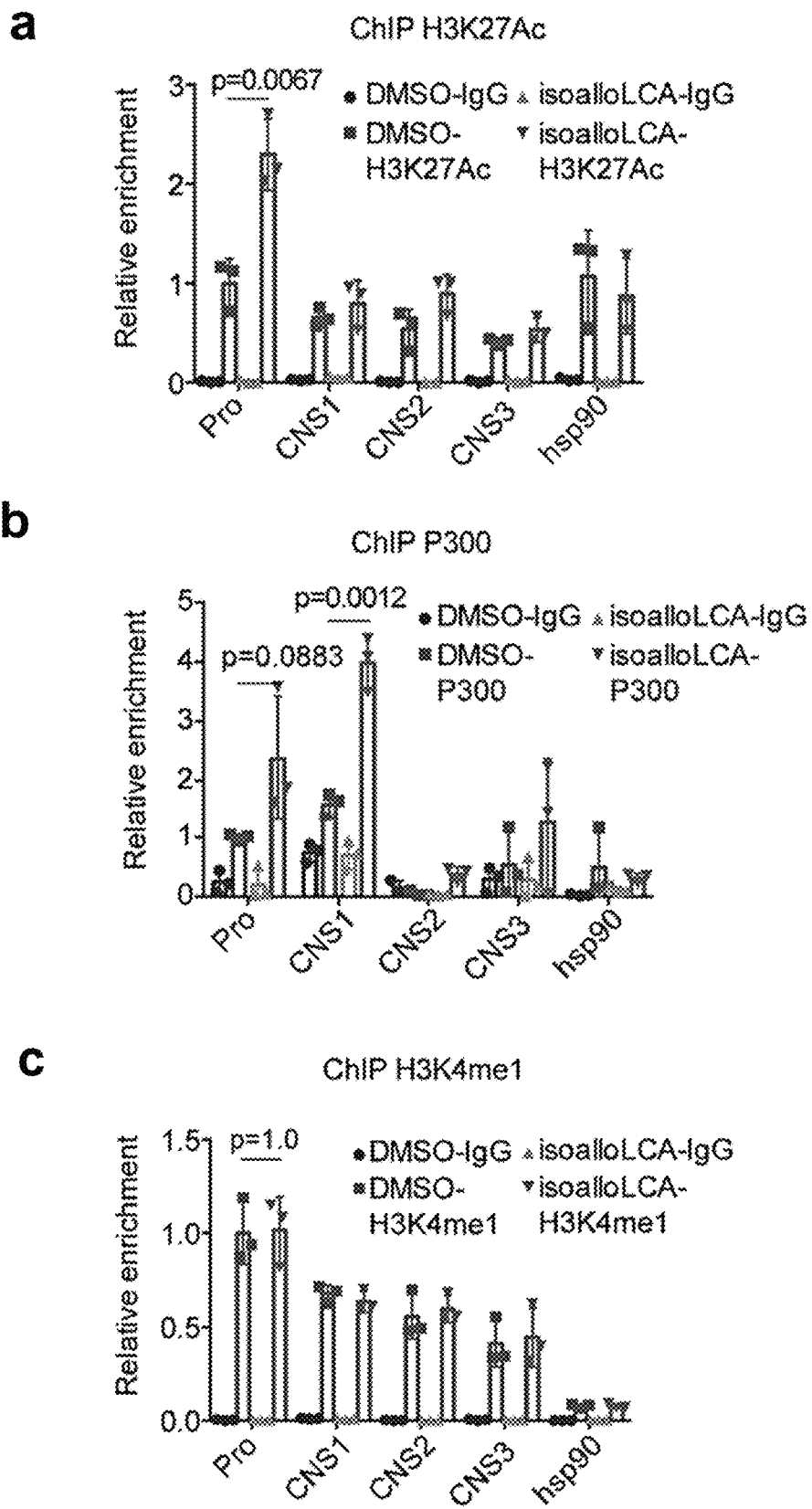
Figure 10:
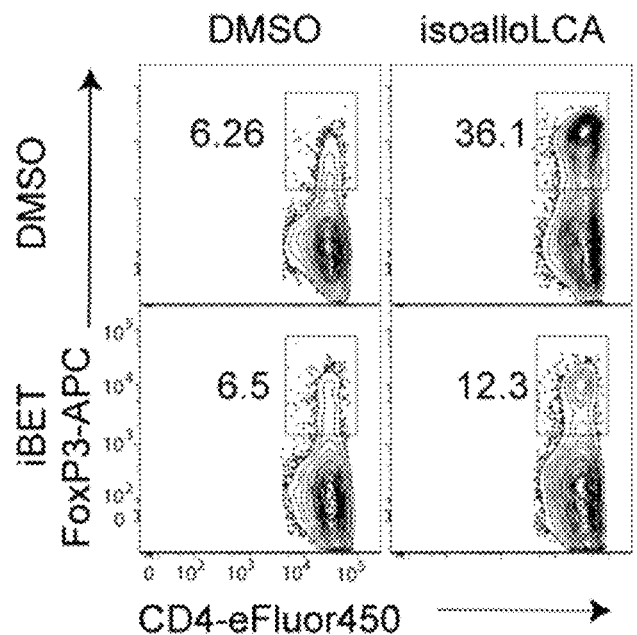
Figure 10:
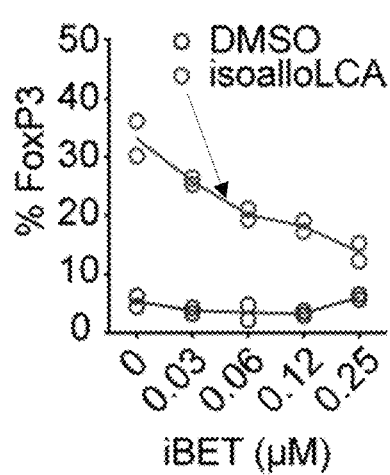
Figure 10:
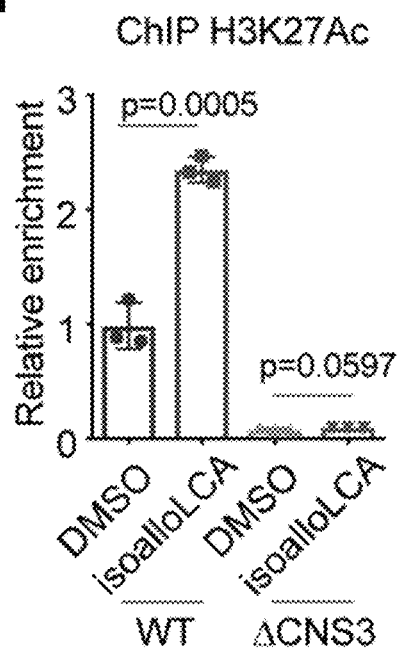
Figure 10:
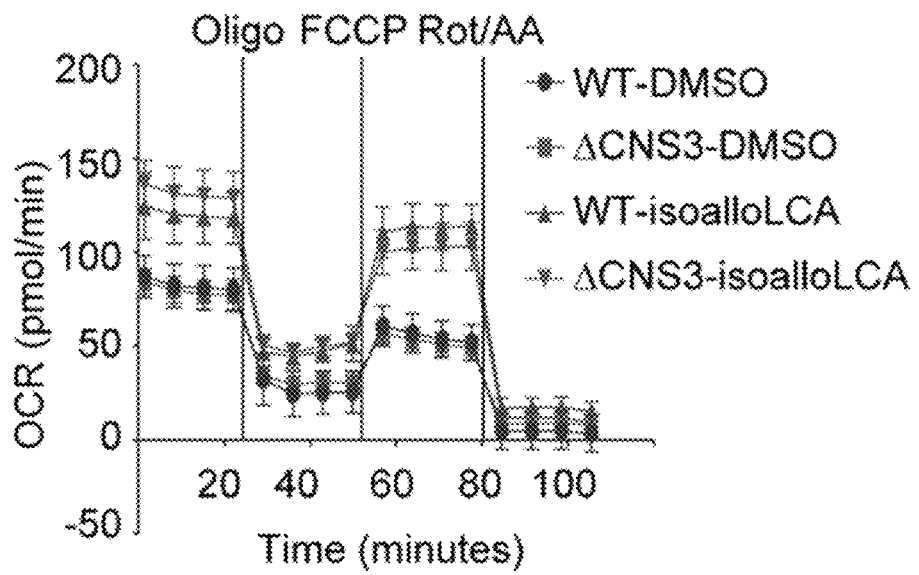
Figure 10:
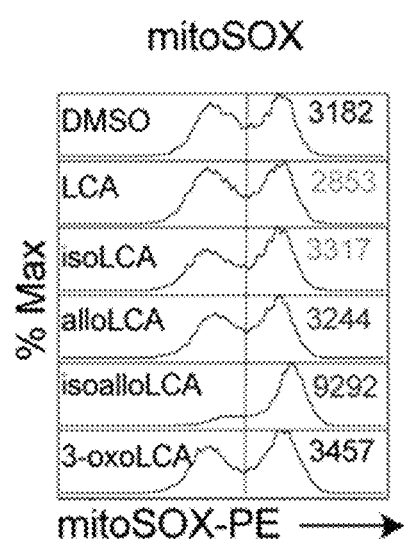
Figure 10:
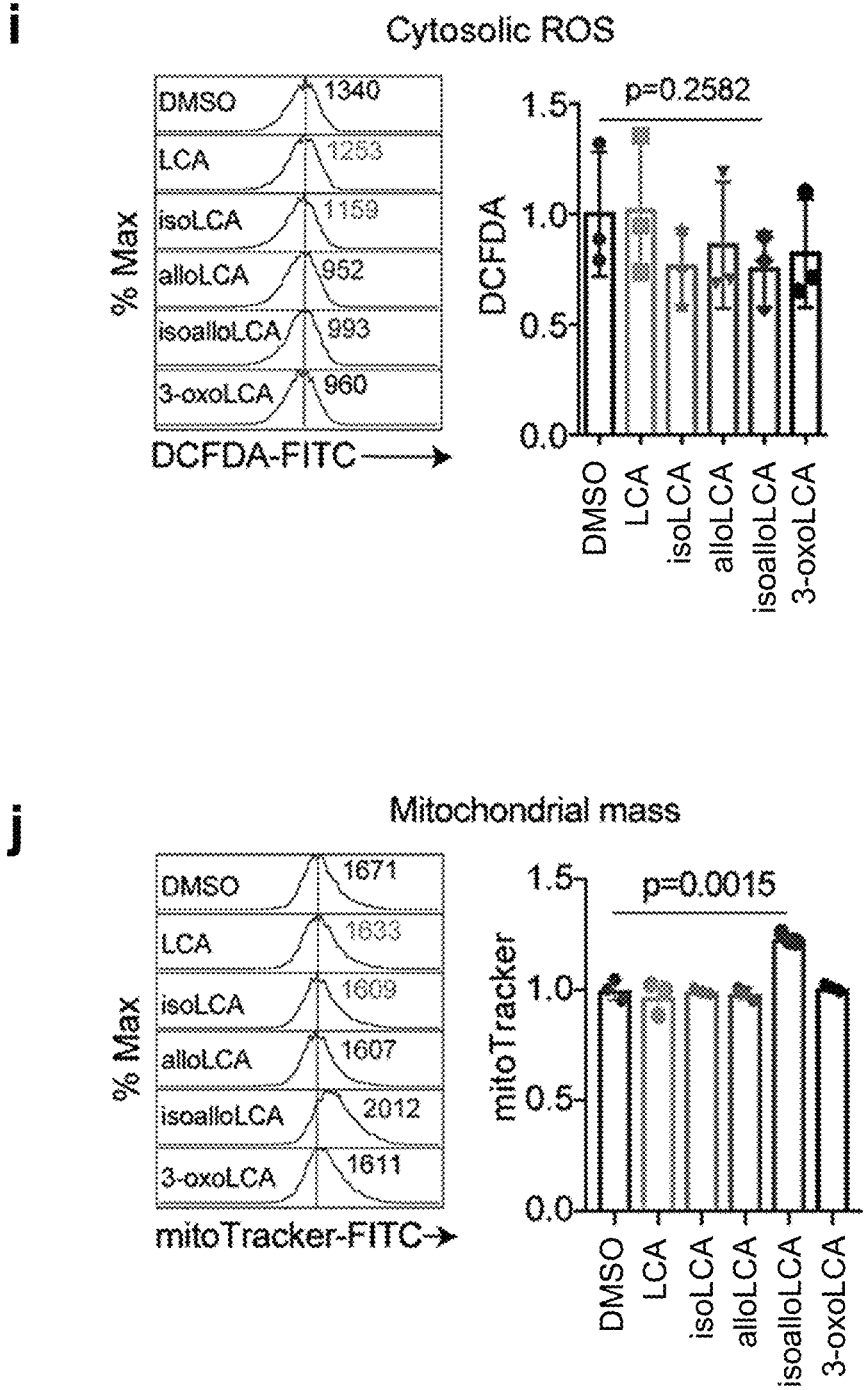
Figure 10:
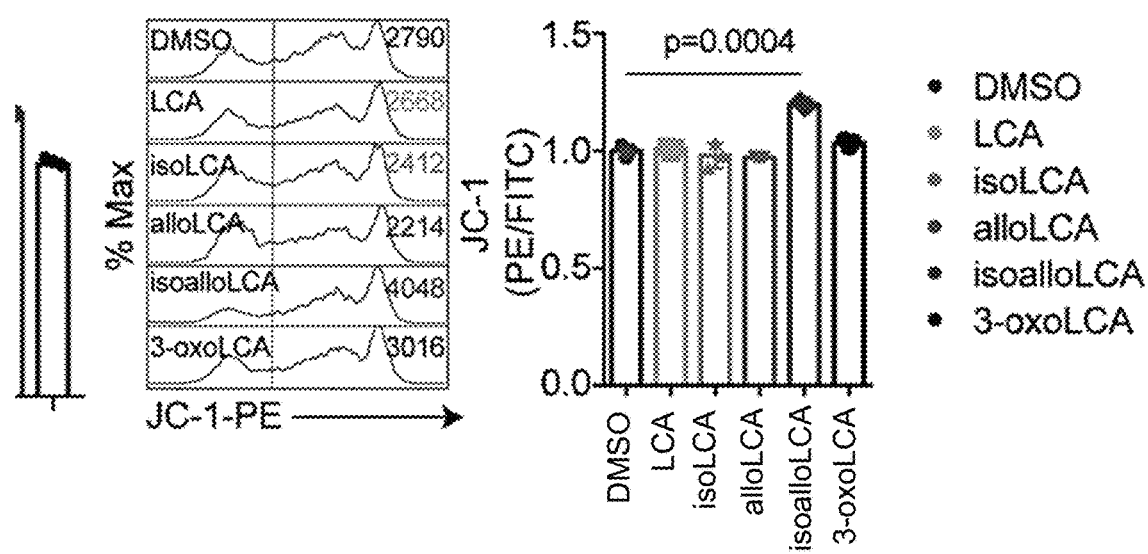
Figure 10:
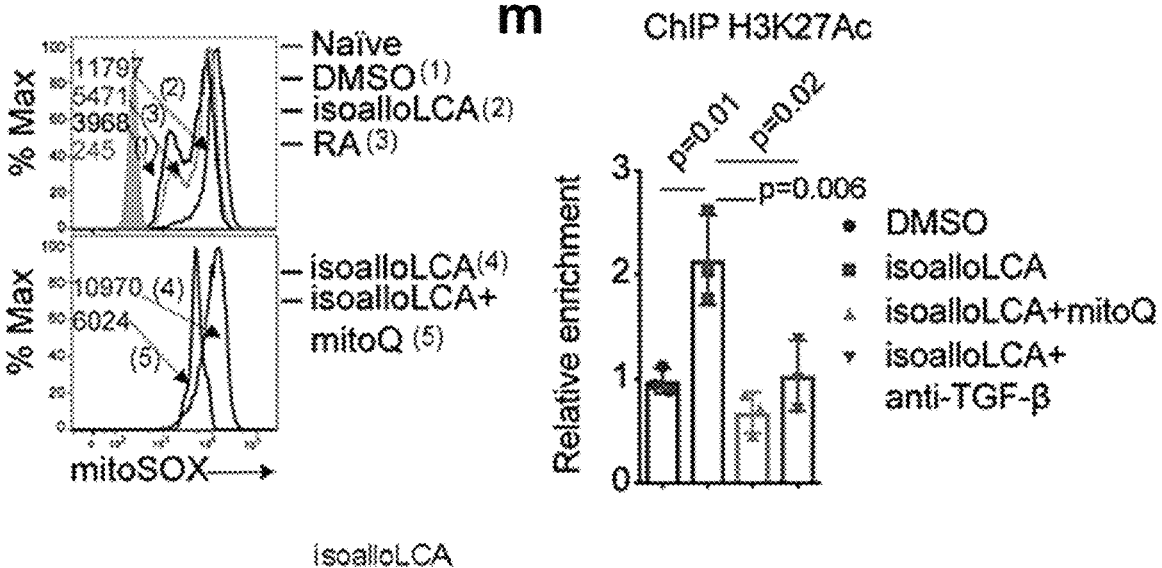
Figure 10:
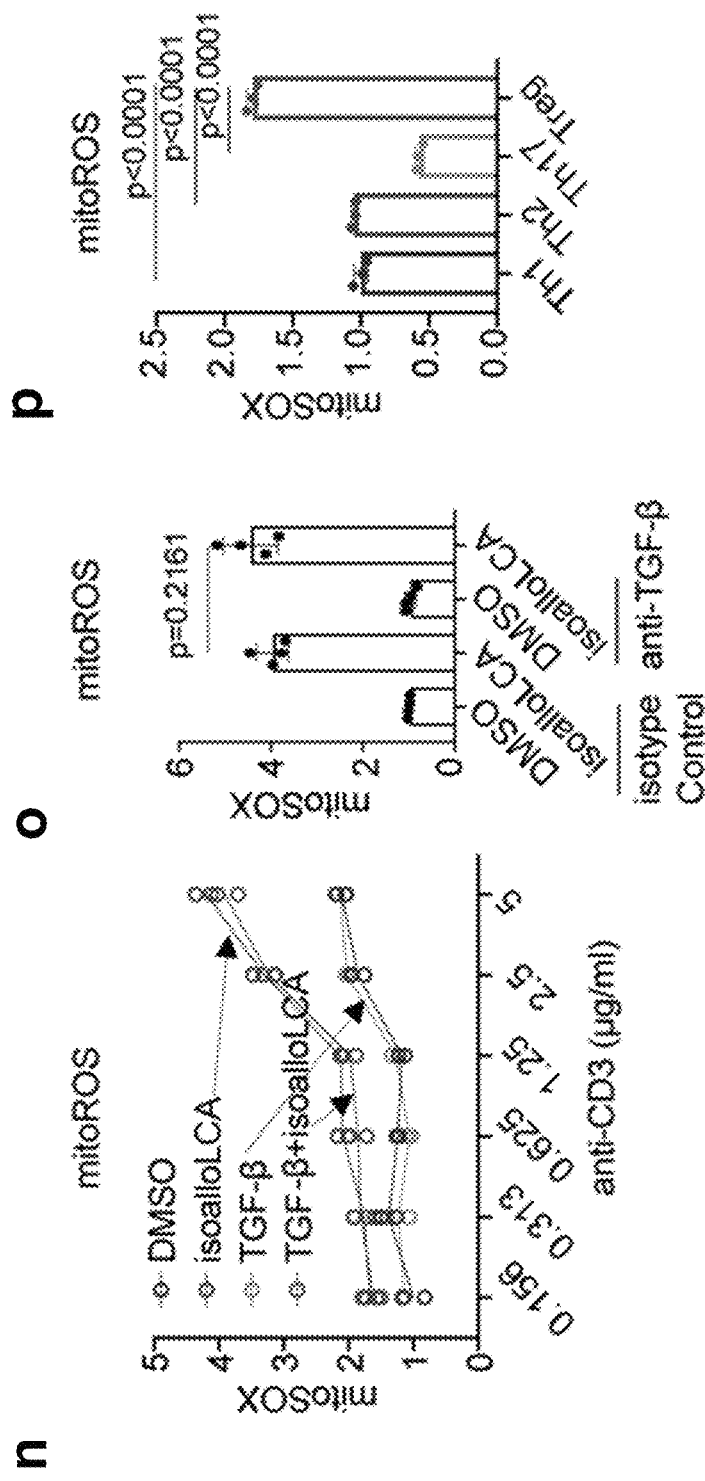
Figure 10:
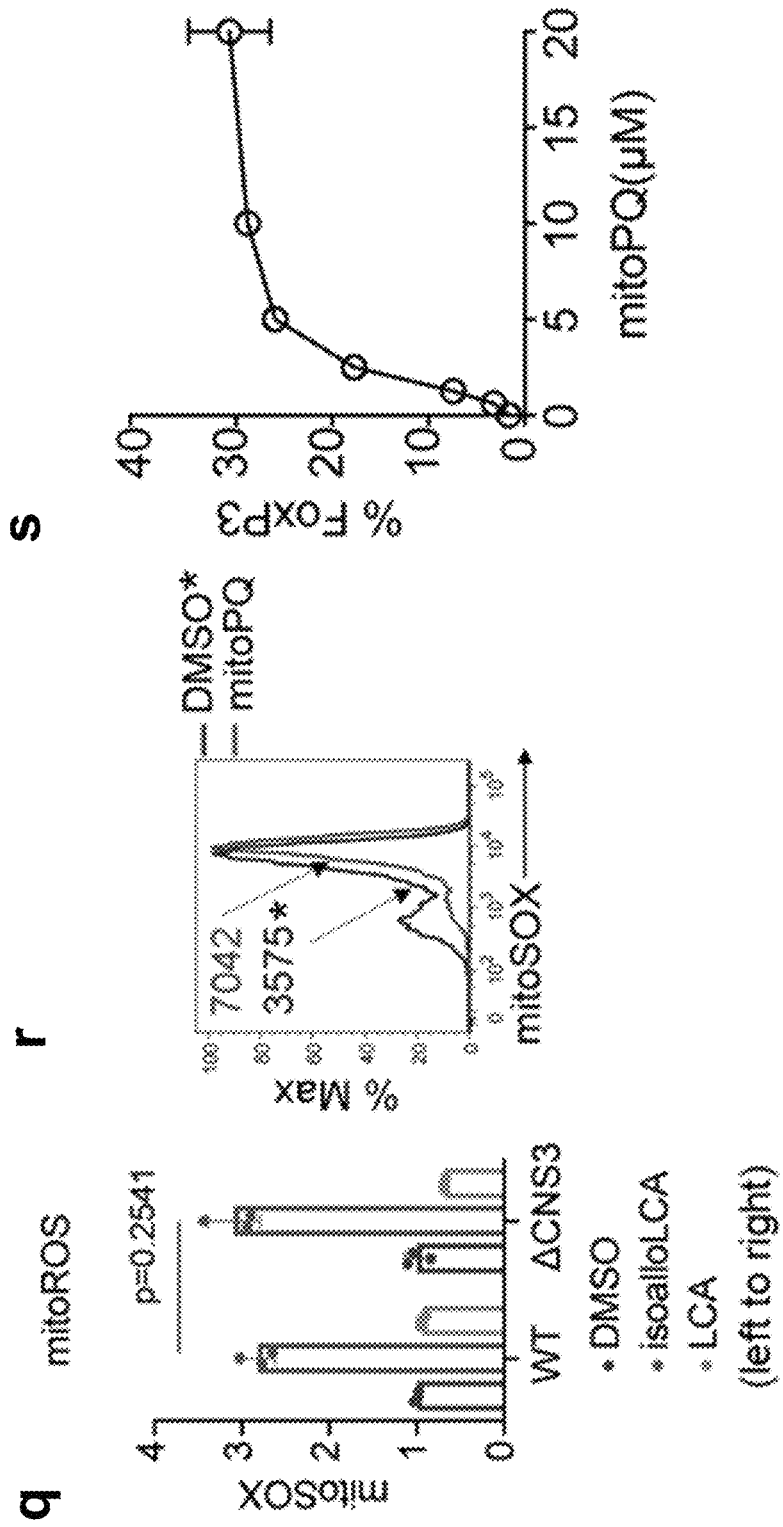
Figure 10:
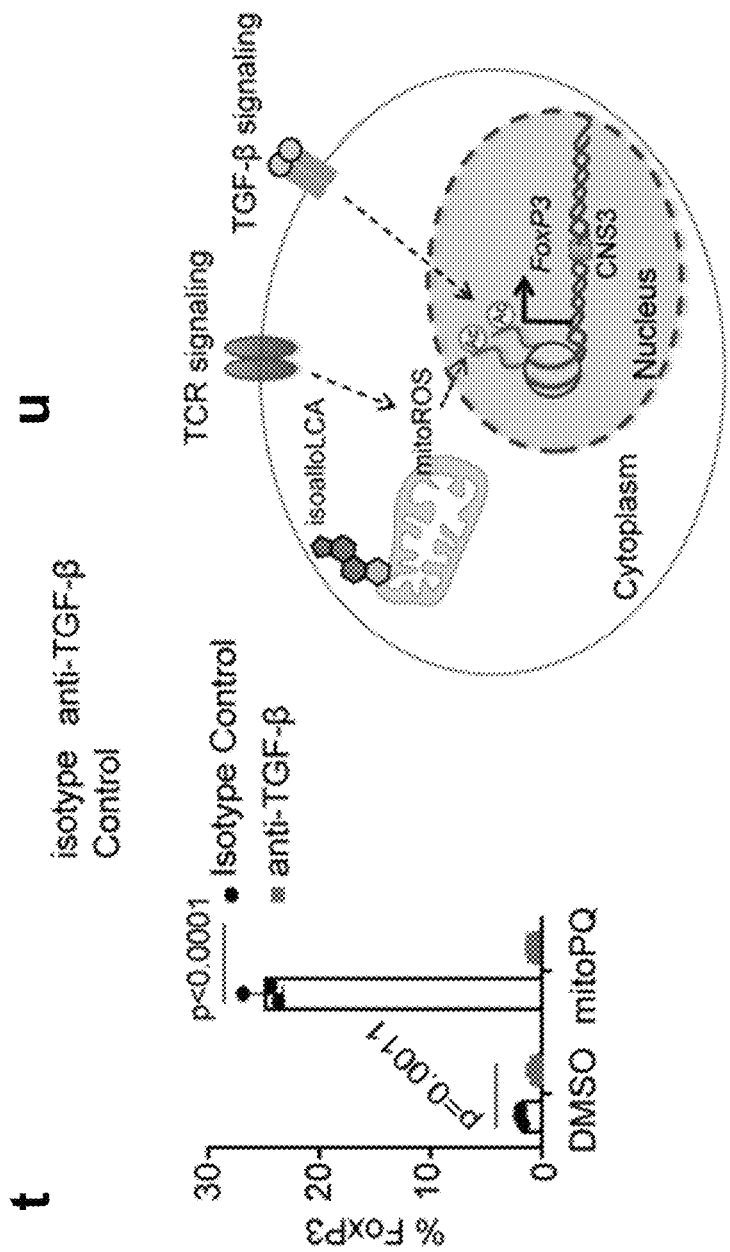

FIG. 10 shows isoalloLCA-dependent FoxP3 transcription requires mitochondrial ROS and H3K27Ac. a-c, ChIP analysis of H3K27Ac, P300 and H3K4me1 on FoxP3 gene locus. Chromatin obtained from DMSO- and isoalloLCA-treated WT cells was immunoprecipitated with IgG, anti-H3K27Ac, anti-P300, or anti-H3K4me1 antibodies, followed by real-time PCR analysis (n=3/group). Primers targeting FoxP3 promoter (Pro), CNS1, CNS2 and CNS3 region and hsp90 promoter were used for qPCR quantification. Relative enrichment was calculated as fold change relative to the ChIP signal at the FoxP3 promoter of the DMSO-treated control. d and e, Flow cytometry and quantification of CD4+ T cells stained intracellularly for FoxP3. Naïve CD4+ T cells isolated from WT mice (n=2/group) were cultured with anti-CD3/28, IL-2 and TGF-β (0.05 ng/mL) in the presence of DMSO or isoalloLCA (20 μM) in the presence or absence of iBET. f, ChTP analysis of H3K27Ac on the FoxP3 promoter region. Naïve CD4+ T cells isolated from WT or CNS3 knockout mice (n=3/group) were treated with DMSO or isoalloLCA (20 μM). g, Seahorse analysis of OCR with naïve CD4+ T cells isolated from WT or CNS3 knockout mice cultured with anti-CD3/28 and IL-2 for 48 h, in the presence of DMSO or isoalloLCA (20 μM). Measurements from six wells from two mice for each genotype. h-k, T cells were cultured with DMSO, LCA, isoLCA, alloLCA, isoalloLCA or 3-oxoLCA at 20 μM for 48 h. Their mitochondrial and cytoplasmic ROS were measured by mitoSOX (h) and 2',7'-dichlorofluorescein diacetate (DCFDA) (i), respectively. Total mitochondria mass was measured by MitoTracker (j) and the mitochondrial membrane potential measured by JC-1 dye (k). MFIs of different treatments were normalized as fold changes to those of DMSO control (n=3/group). 1, Mitochondria ROS production measured by mitoSOX with T cells cultured with DMSO, isoalloLCA (20 μM), retinoic acid (RA, 1 nM), or isoalloLCA (20 μM)+mitoQ (0.5 μM) for 48 h. m, ChIP analysis (n=3/group) of H3K27Ac on the FoxP3 promoter of T cells, treated with DMSO, isoalloLCA, isoalloLCA+mitoQ, or isoalloLCA+anti-TGF-β for 72 h. n-q, Mitochondrial ROS production measured by mitoSOX with T cells cultured with different concentrations of anti-CD3 and treated with DMSO, isoalloLCA (20 μM), TGF-β (0.05 ng/ml), or isoalloLCA plus TGF-β (n=2/group) (n); or with T cells treated with DMSO or isoalloLCA (20 μM) plus an isotype control or anti-TGF-β antibody (n=4/group) (o); or with T cells cultured under Th1, Th2, Th17 or Treg conditions (n=3/group) (p); or with naïve CD4⁺ T cells isolated from WT or CNS3 knockout mice and cultured with anti-CD3/28 and IL-2 (n=3/group) (q). r, Mitochondria ROS production measured by mitoSOX with T cells cultured with DMSO or mitoPQ (5 μM) for 48 h. s, Dose-dependent effects of mitoPQ on Treg differentiation (n=3). t, Quantification of Treg differentiation in vitro on naïve CD4⁺ T cells cultured in the presence of DMSO or mitoPQ (5 μM) and treated with isotype control or anti-TGF-β antibody (n=3/group). u, A model showing the mechanism of isoalloLCA enhancement of Treg differentiation. n, number of biologically independent samples. Data are representative of two independent experiments (1, r) and shown as the mean±standard deviation by unpaired t-test with 2-tailed p-value.

Figure 11:
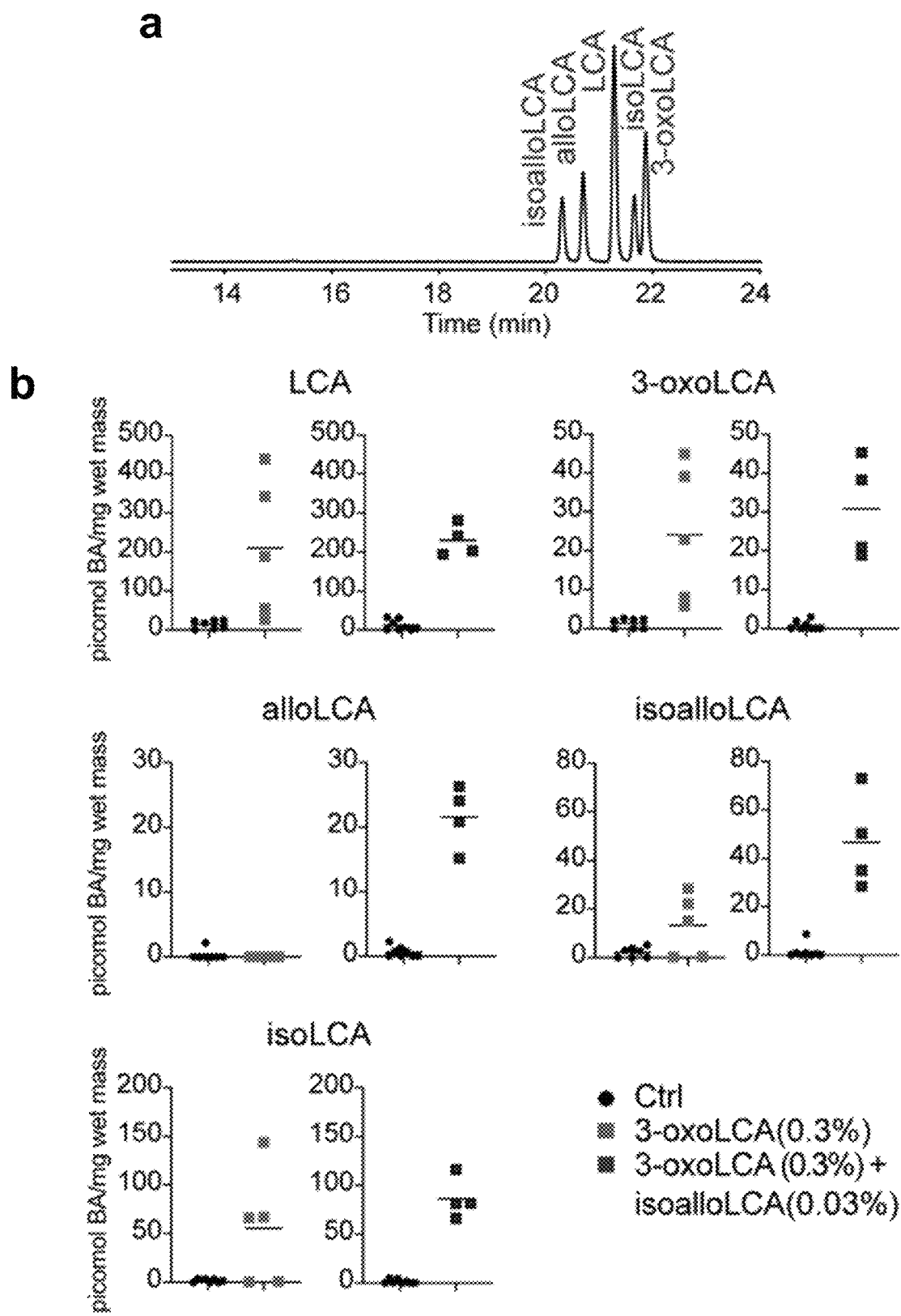
Figure 11:
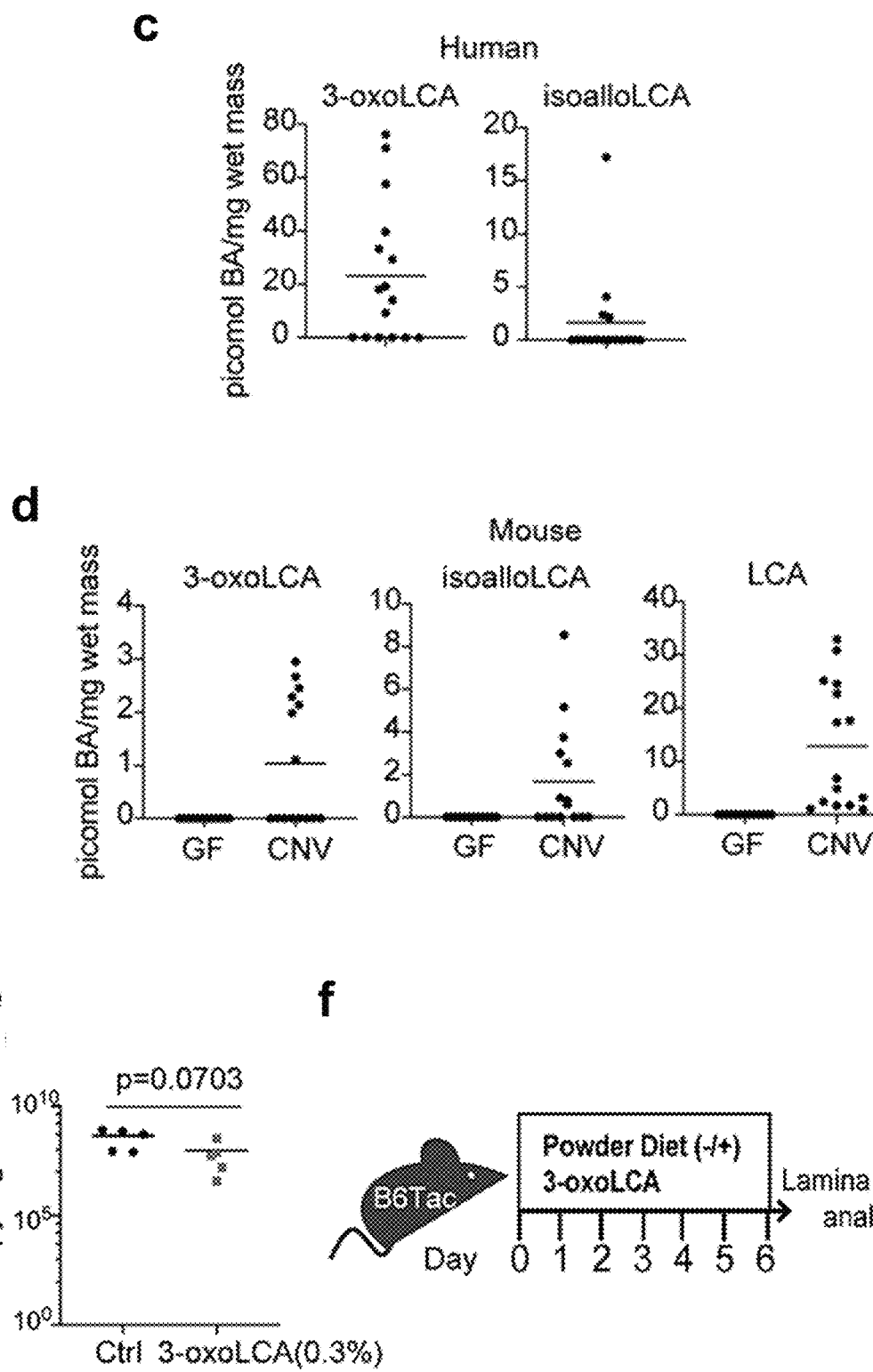
Figure 11:
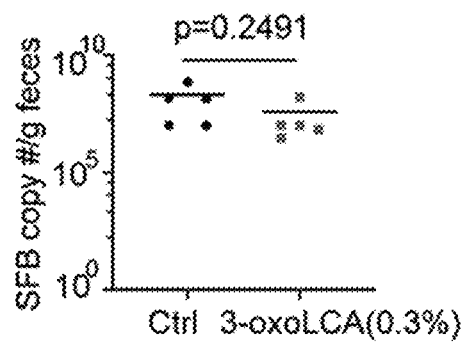
Figure 11:
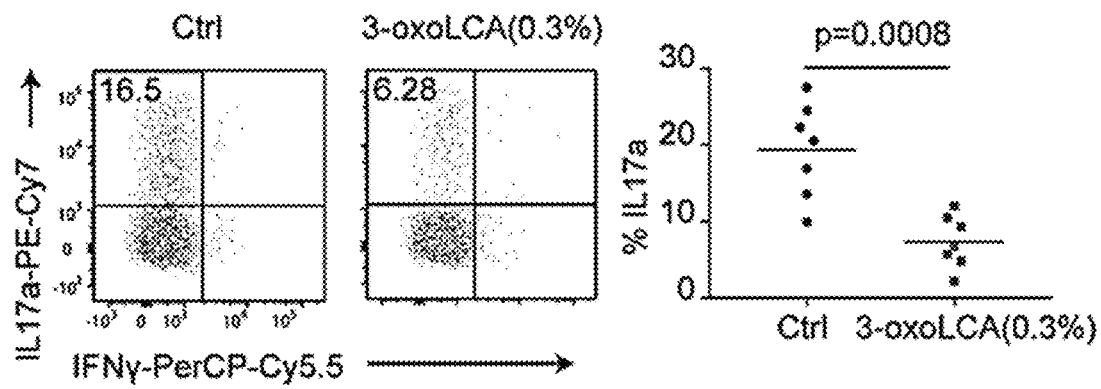
Figure 11:
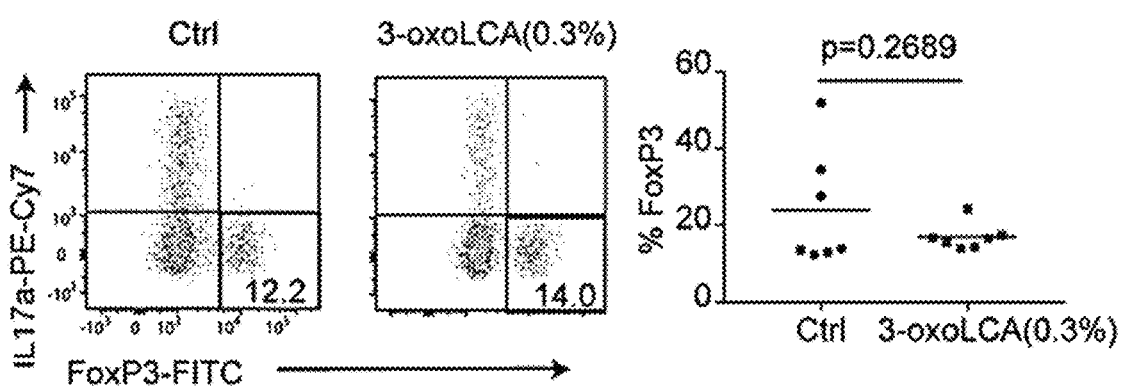
Figure 11:
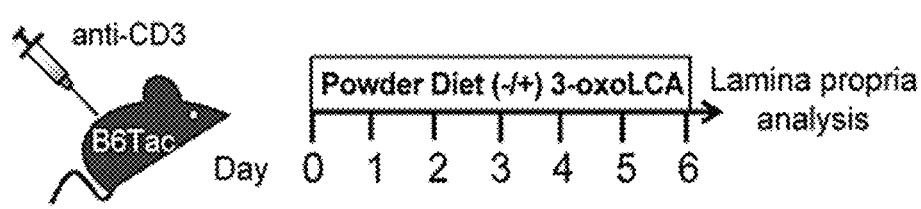
Figure 11:
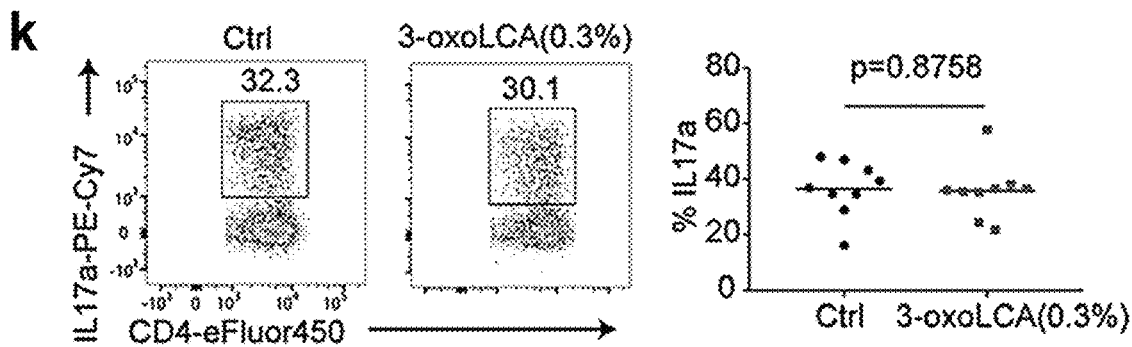
Figure 11:
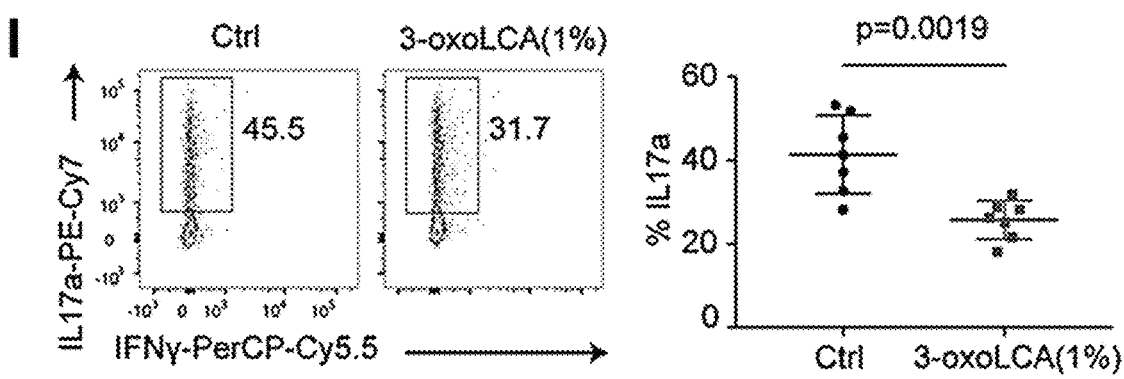
Figure 11:
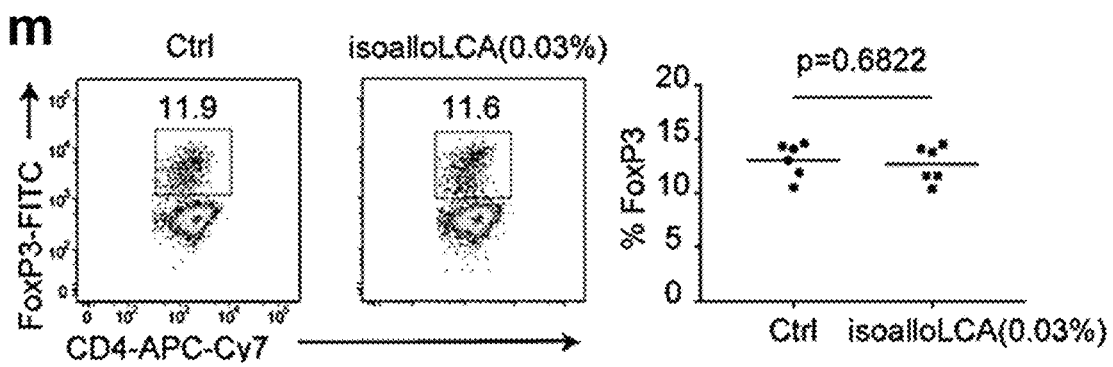
Figure 11:
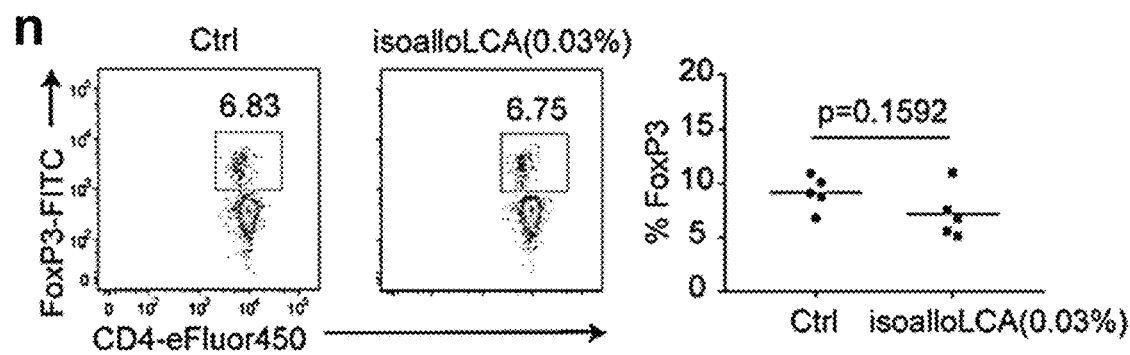
Figure 11:
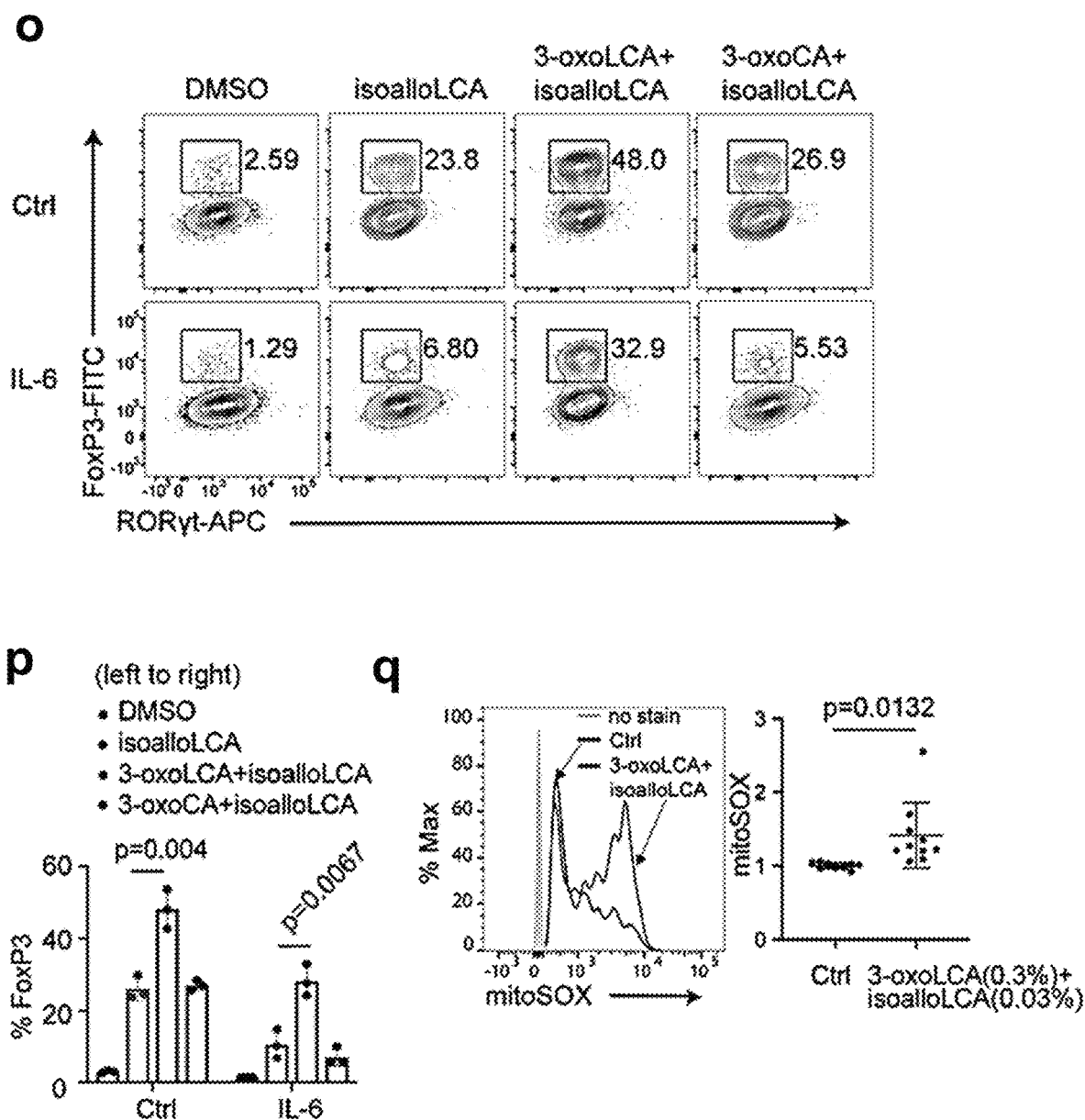

FIG. 11 shows 3-oxoLCA inhibits the differentiation of Th17 cells but not Tregs, and isoalloLCA alone does not enhance Treg differentiation in vivo. a, UPLC/MS spectra of LCA and its isomers isoalloLCA, alloLCA, and isoLCA as well as 3-oxoLCA. b, Quantification of unconjugated LCA and its derivatives in the cecal contents of B6 mice fed on a control or bile acid-containing diet (n=7/5/4 mice for Ctrl/3-oxoLCA/3-oxoLCA+isoalloLCA). c, Quantification of unconjugated 3-oxoLCA and isoalloLCA in human stool samples from patients with ulcerative colitis (n=16 donors). d, Quantification of unconjugated 3-oxoLCA, isoalloLCA and LCA in mouse cecal contents from germ-free (GF) or conventionally housed (CNV) mice (n=15 mice/group). e, B6 Jax mice gavaged with SFB. SFB colonization measured by qPCR analysis calculated as copy number (n=5 mice/group). f, Diagram showing experimental design. B6 Taconic mice were fed a 3-oxoLCA (0.3%) containing diet for 7 days. g, SFB colonization measured by qPCR analysis calculated as SFB copy number (n=5 mice/group). h and i, Flow cytometric analysis and quantification of Th17 (h) and Treg (i) cells of the ileal lamina propria (n=7 mice/group). j-l, Experimental scheme of anti-CD3 experiment with 3-oxoLCA (j). Flow cytometric analysis and quantification of CD4⁺ cells of the lamina propria following an anti-CD3 injection from B6 mice fed with control or 3-oxoLCA (0.3%) diet (n=9 mice/group) (k), or 3-oxoLCA (1%) diet (n=7 mice/group) (l). m and n, Flow cytometric analysis and quantification of CD4⁺ cells of the ileal lamina propria in steady-state (m) (n=6 mice/group) or following an anti-CD3 injection (n) (n=5 mice/group). B6 mice were fed with control or isoalloLCA (0.03%) diet. o and p, Flow cytometry (o) and quantification (p) of CD4⁺ T cells stained intracellularly for FoxP3 showing that the combination of 3-oxoLCA and isoalloLCA further increases Treg cell differentiation. Naïve CD4⁺ T cells isolated from WT B6 mice (n=3 biologically independent samples) treated with DMSO, isoalloLCA (20 μM), a mixture of 3-oxoLCA (20 μM) and isoalloLCA (20 μM), or a mixture of 3-oxoCA (20 μM) and isoalloLCA (20 μM) and cultured with anti-CD3/28 and IL-2, with or without addition of IL-6 (62.5 μg/ml). q, mitoROS production in total CD4⁺ T cells isolated from the ileal lamina propria. Mice were fed a control diet or diet containing a mixture of 3-oxoLCA (0.3%)+isoalloLCA (0.03%) (n=9, 10 mice) and injected with 10 μg of anti-CD3 to induce inflammation. Data are shown as the mean±standard deviation by unpaired t-test with 2-tailed p-value.

Figure 12:
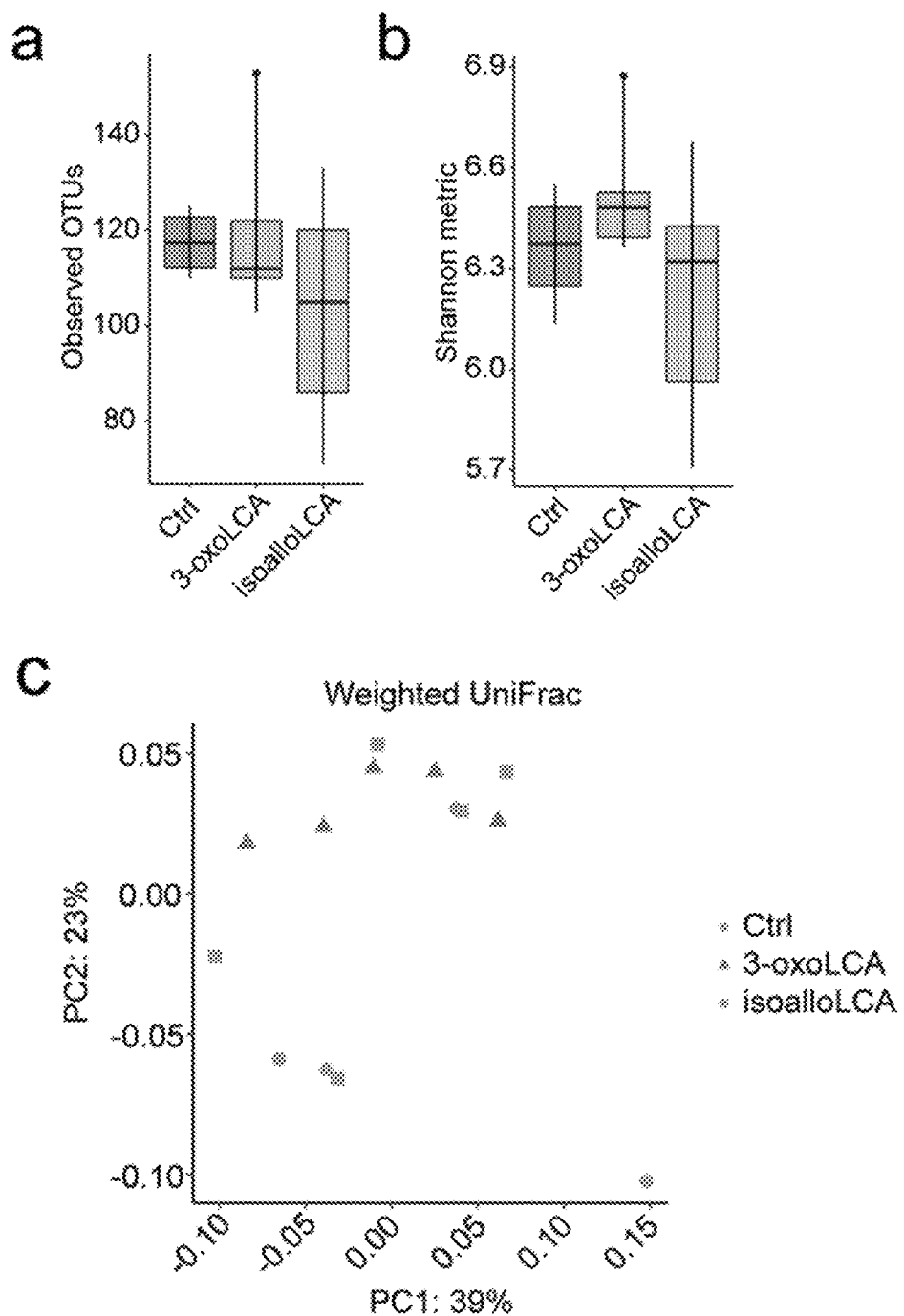
Figure 12:
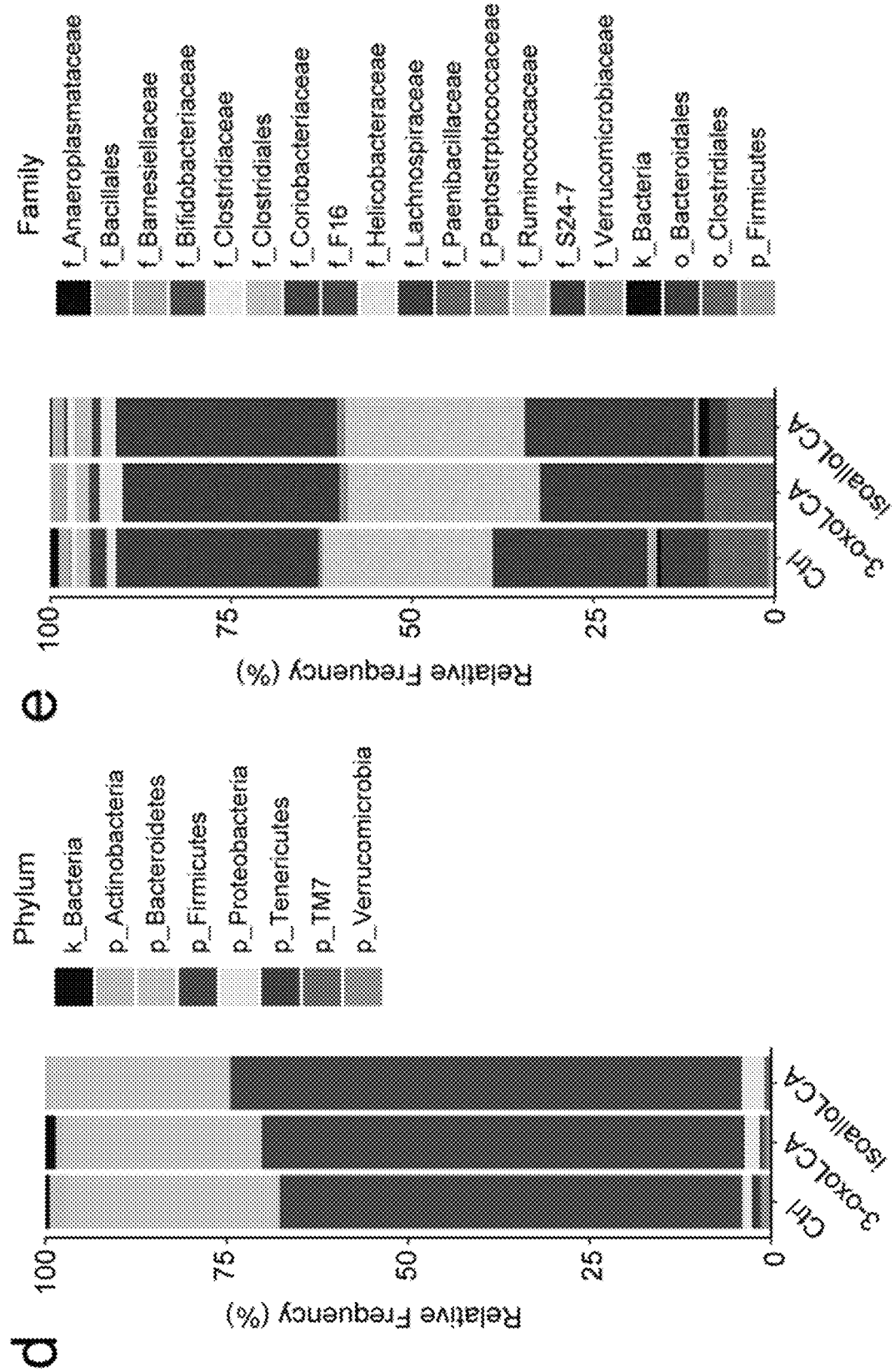
Figure 12:
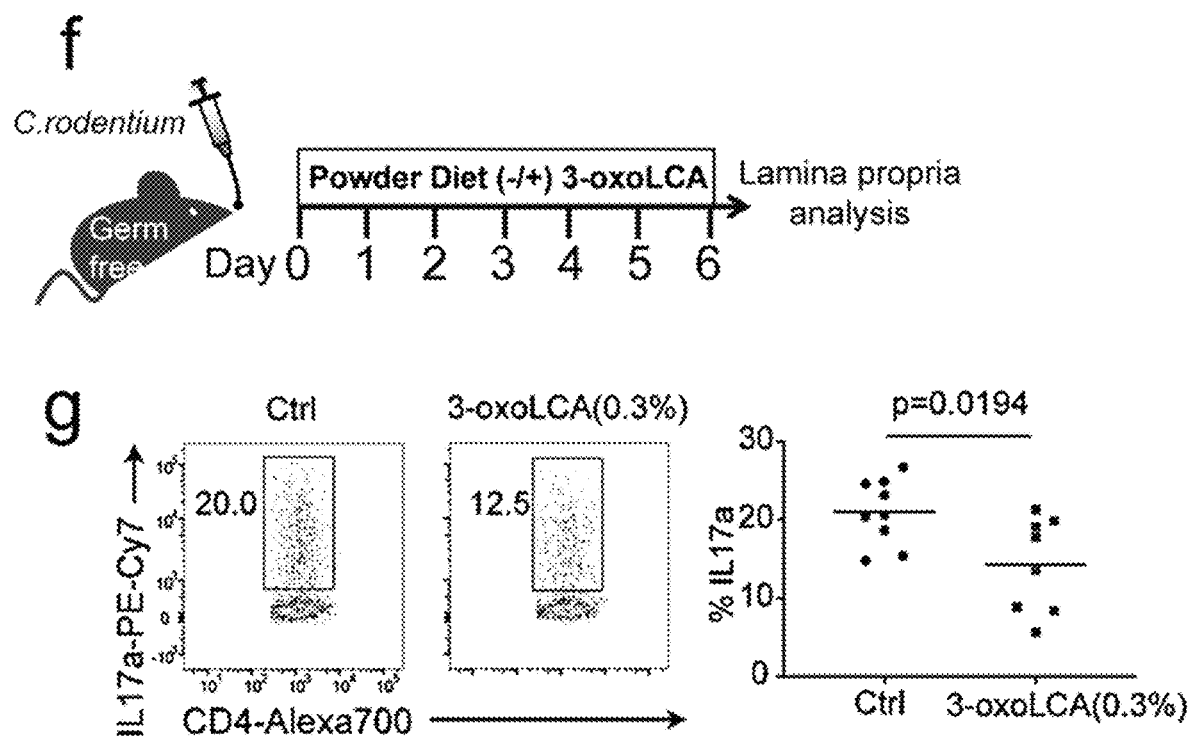

FIG. 12 shows 3-oxoLCA or isoalloLCA does not significantly alter gut microbiota. a, Box plot showing operational taxonomic unit (OTU) numbers. b, Shannon diversity of fecal microbiota based on 16S rRNA gene amplicon sequencing. For the box plots (a, b), the three horizontal lines of the box represent the third quartile, median and first quartile, respectively from top to bottom. The whiskers above and below the box show the maximum and minimum. c, Principal coordinates analysis (PCoA) based on weighted UniFrac distances of 16S rRNA amplicon sequencing of fecal microbiota. d and e, Average relative abundance of microbiota at the phylum (d) and the family (e) levels by taxon-based analyses (n=4, 5, 5 mice for Ctrl, 3-oxoLCA, isoalloLCA group). f and g, Experimental scheme (f) and flow cytometric analysis and quantification (g) of CD4⁺ cells of the colon lamina propria in germ-free B6 mice, infected with *Citrobacter rodentium*. Mice were fed an autoclaved diet with or without 3-oxoLCA (0.3%) (n=9 mice/group). Data are shown as the mean±standard deviation by unpaired t-test with 2-tailed p-value.

Figure 13:
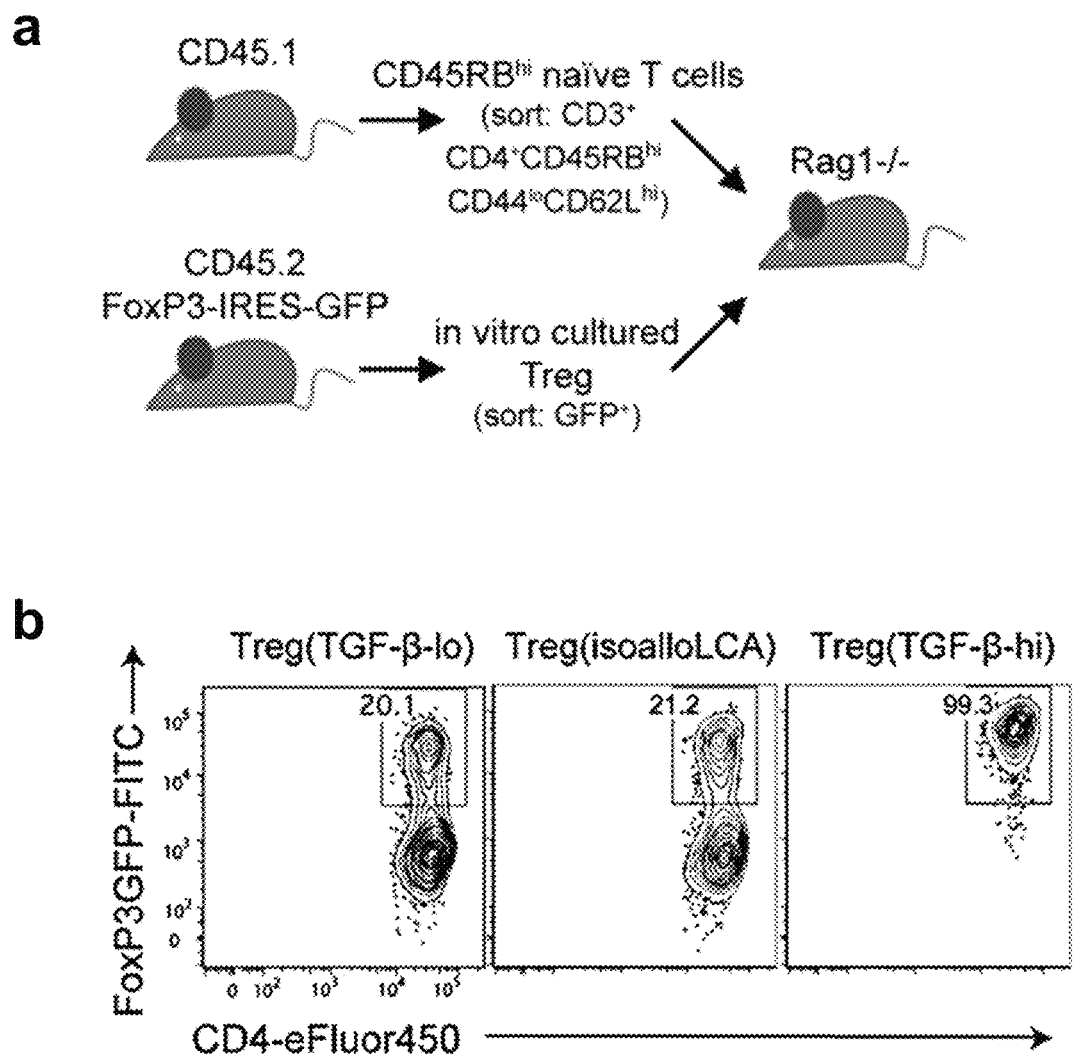
Figure 13:
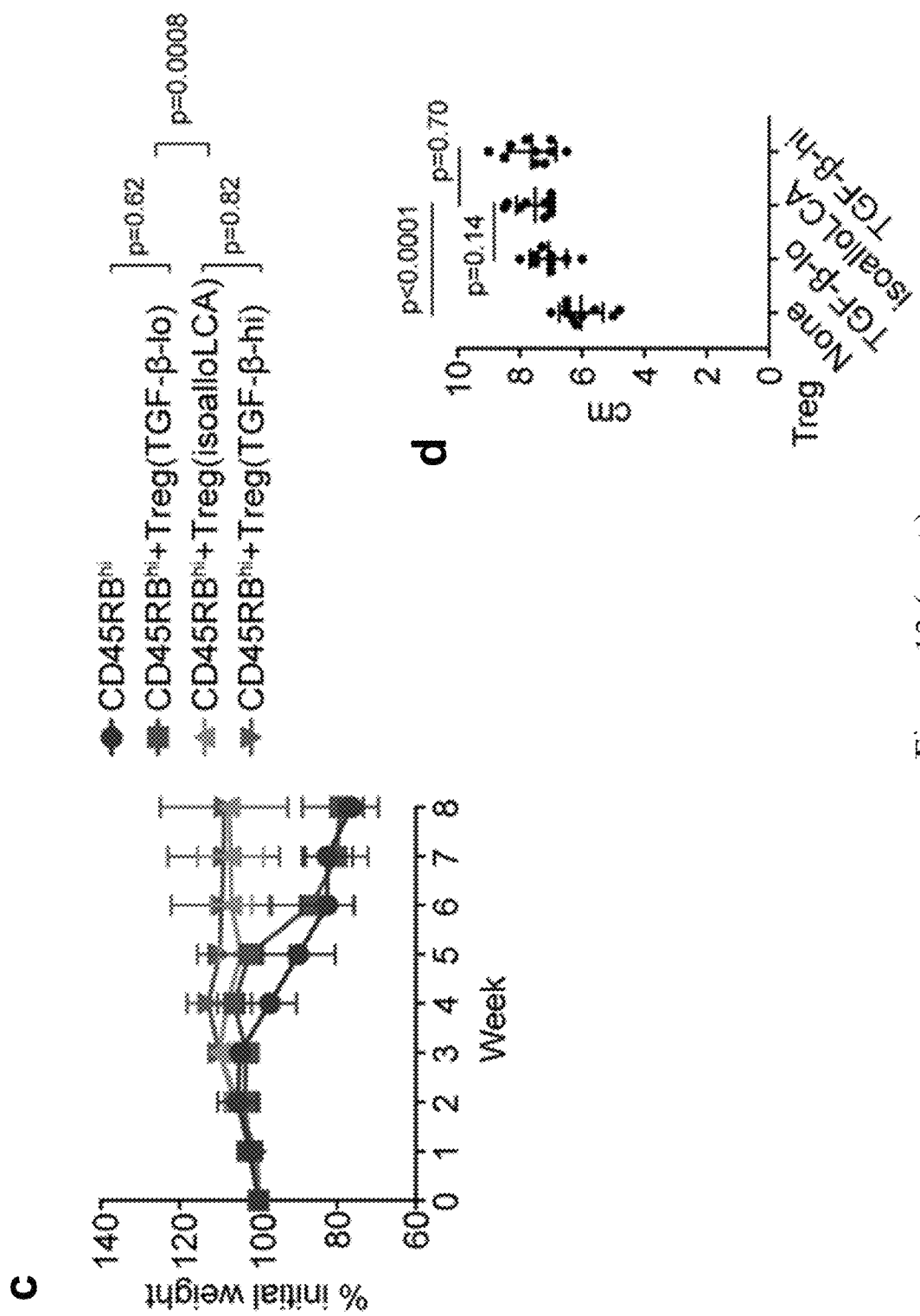
Figure 13:
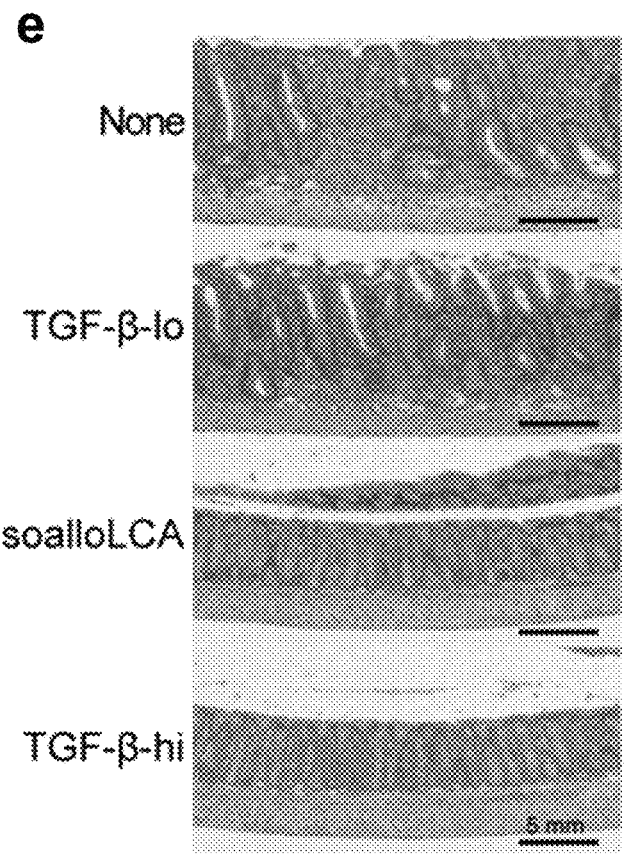
Figure 13:
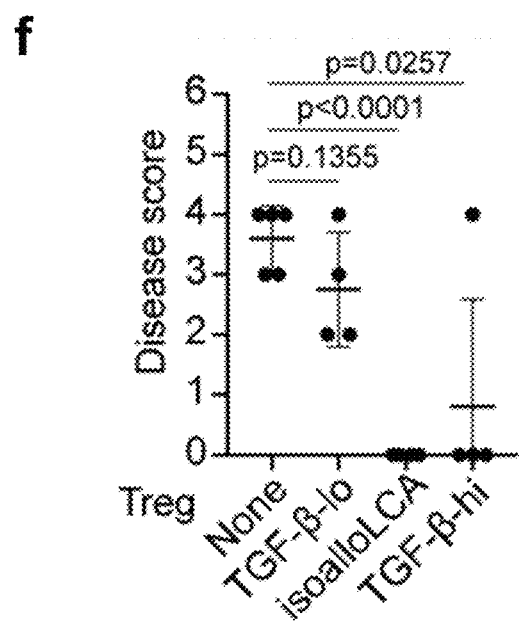
Figure 13:
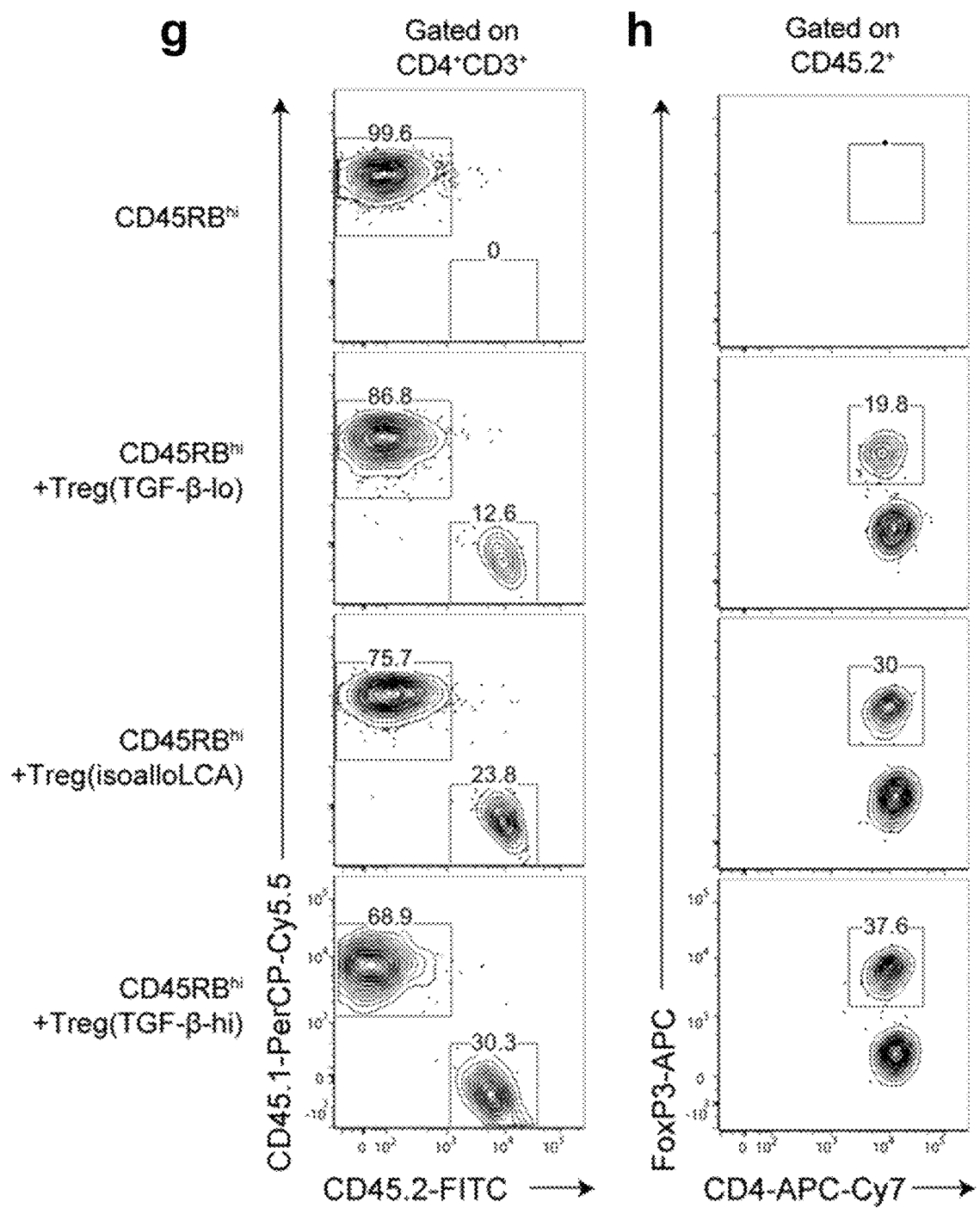
Figure 13:
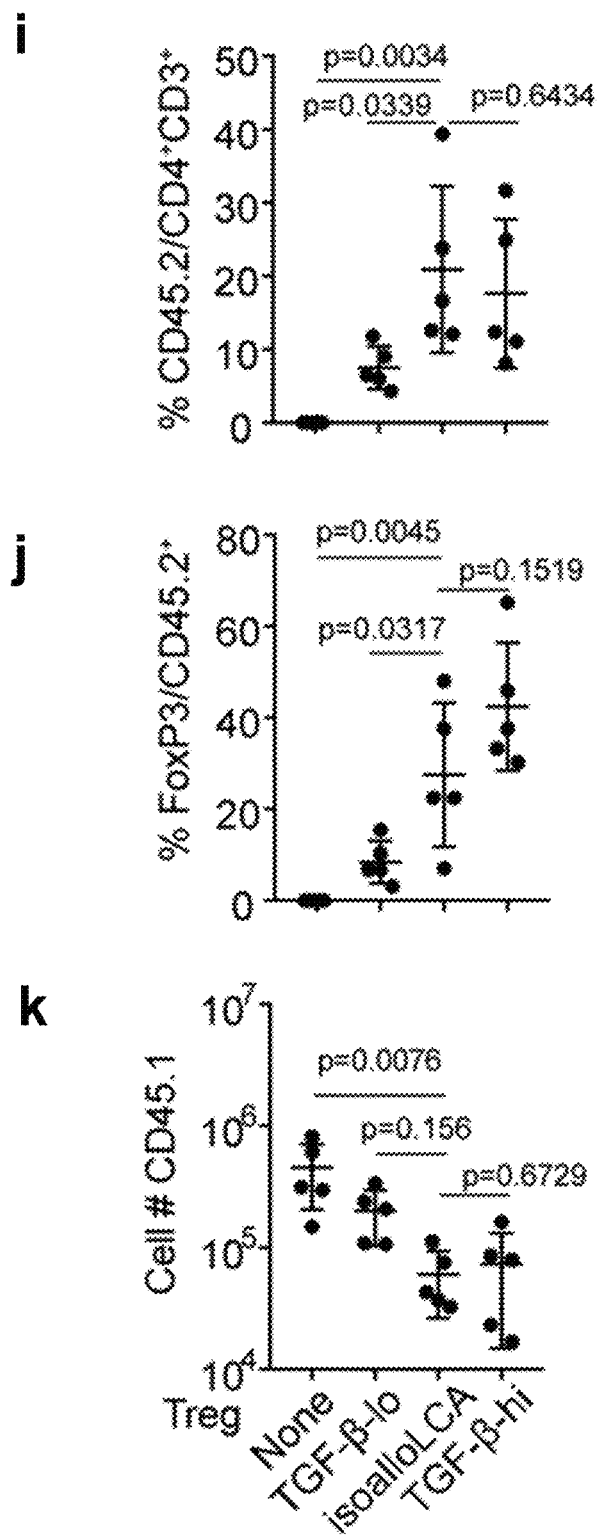

FIG. 13 shows isoalloLCA-induced Treg cells suppress transfer colitis. a, Experimental scheme. Rag1⁻/⁻ recipient mice were transferred intraperitoneally with 0.5 million CD45RB$^{hi}$ naïve CD4⁺ T cells (CD45.1) and with or without co-transfer of 0.5 million FoxP3-GFP⁺ Treg cells (CD45.2). FoxP3-GFP⁺ cells were cultured under TGF-β-lo (0.05 ng/ml), isoalloLCA (20 μM, 0.01 ng/ml TGF-β) and TGF-β-hi (1 ng/ml) conditions with GFP⁻ naïve CD4 T cells, isolated from CD45.2 FoxP3-IRES-GFP mice. b, Flow cytometric analysis of the FoxP3-GFP⁺ cells following in vitro culture. The gated cells were sorted and used for co-transfer. c-f, Weight change monitored for eight weeks, week 7 values are used for unpaired t-test with two-tailed p-value (c) (n=5 mice/group). At the end of the experiment, colon length (d) (n=10 mice/group), H&E staining (e) and the quantification of disease score (f) (n=5 mice for None, 4 mice for other groups). g-j, Flow cytometric analysis and quantification of the frequency of CD45.1 and CD45.2 (g, i) and the frequency of FoxP3⁺ cells in the CD45.2 population (h, j) in each condition (n=5 mice/group). k, Quantification of total CD45.1 cell number in the colon lamina propria (n=5 mice/group). Data are shown as the mean±standard deviation by unpaired t-test with 2-tailed p-value.

Figure 14:
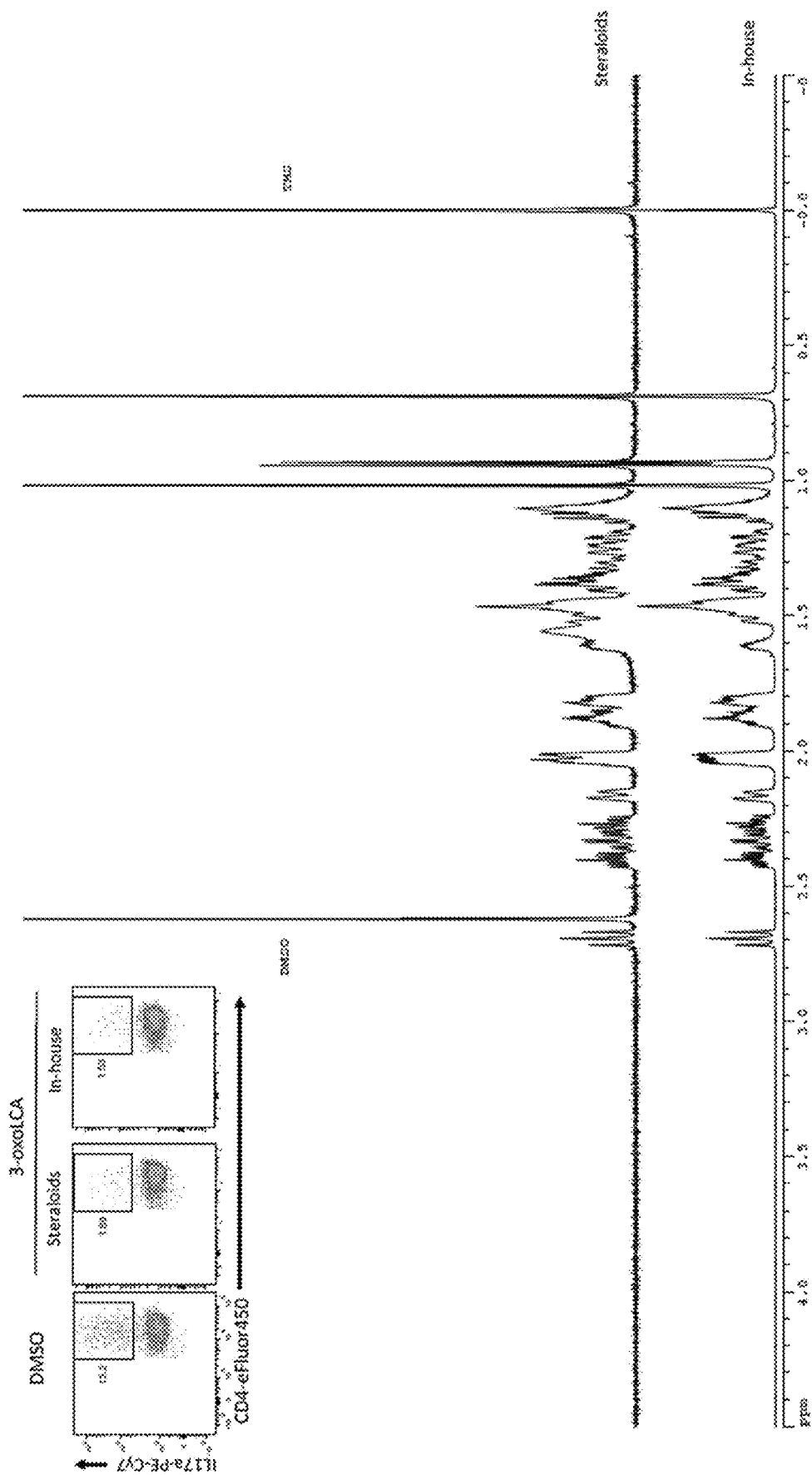

FIG. 14 shows ¹H NMR spectrum (600 MHz, CDCl₃) of 3-oxoLCA and verification by in vitro assay. The compound data and spectrum of 3-oxoLCA are representative of four independent synthesis experiments.

Figure 15:
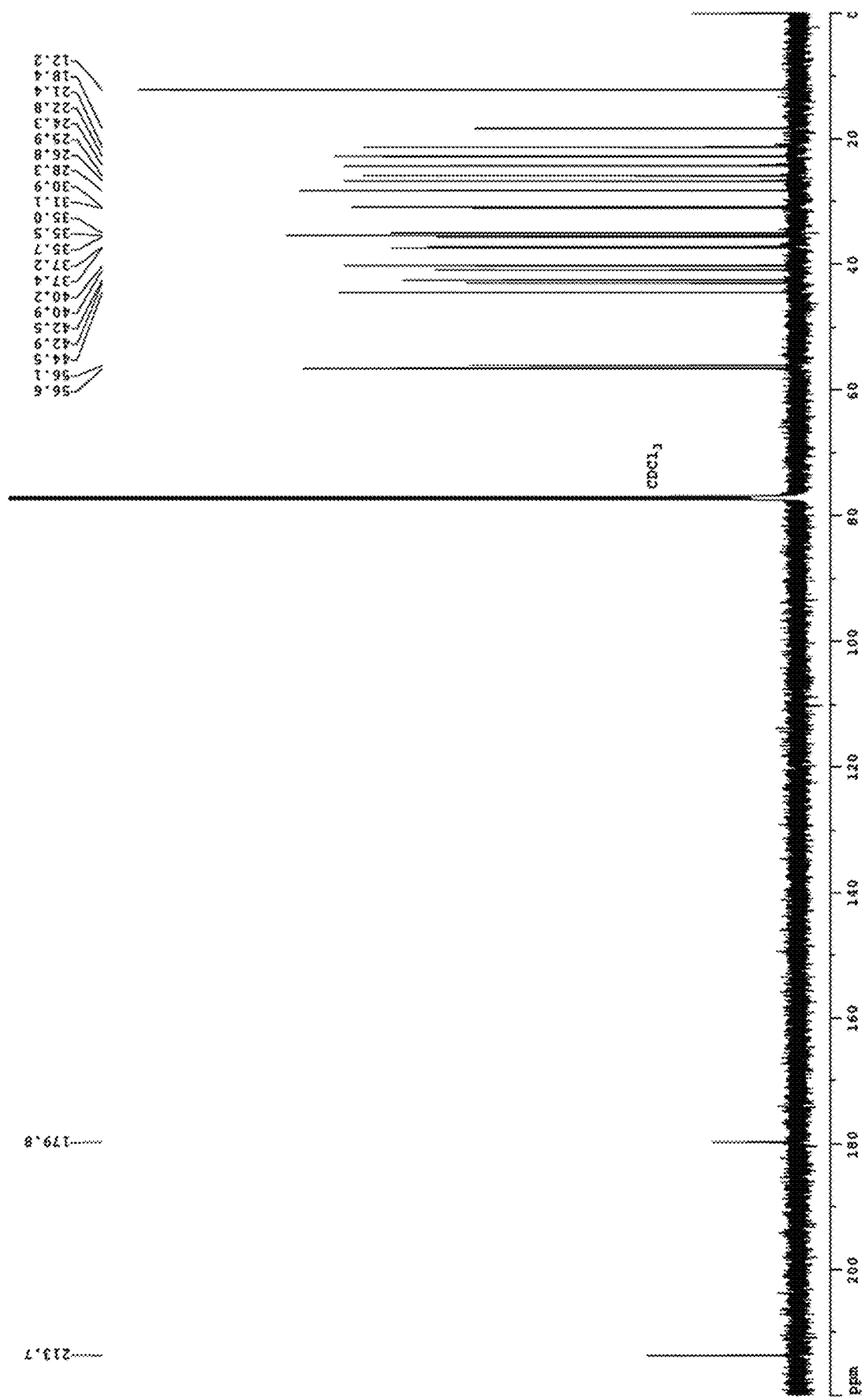

FIG. 15 shows ¹³C{¹H} NMR spectrum (151 MHz, CDCl₃) of 3-oxoLCA. The compound data and spectrum of 3-oxoLCA are representative of four independent synthesis experiments.

Figure 16:
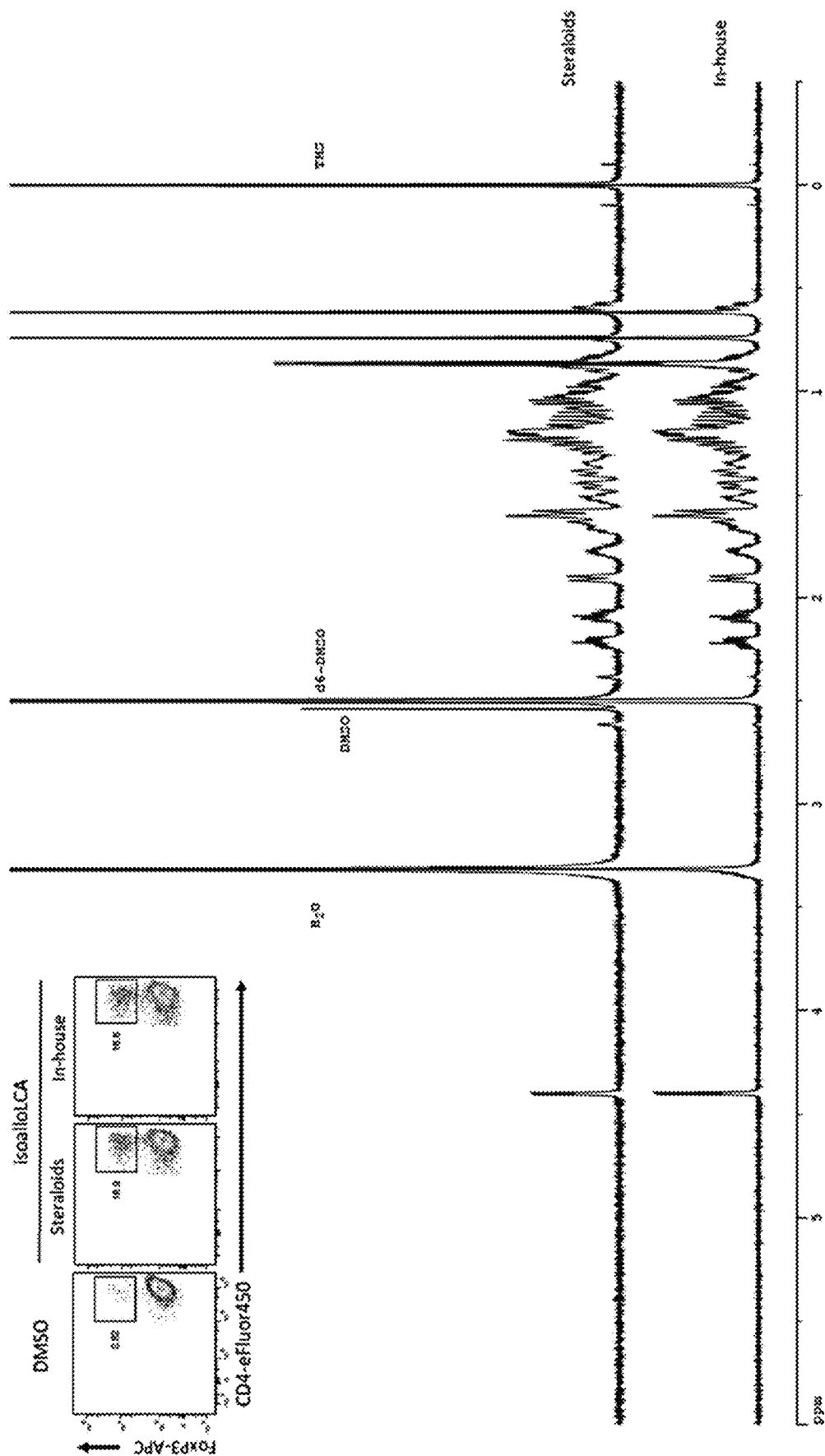

FIG. 16 shows ¹H NMR spectrum (600 MHz, DMSO-d6) of isoalloLCA and verification by in vitro assay. The compound data and spectrum of isoalloLCA are representative of five independent synthesis experiments.

Figure 17:
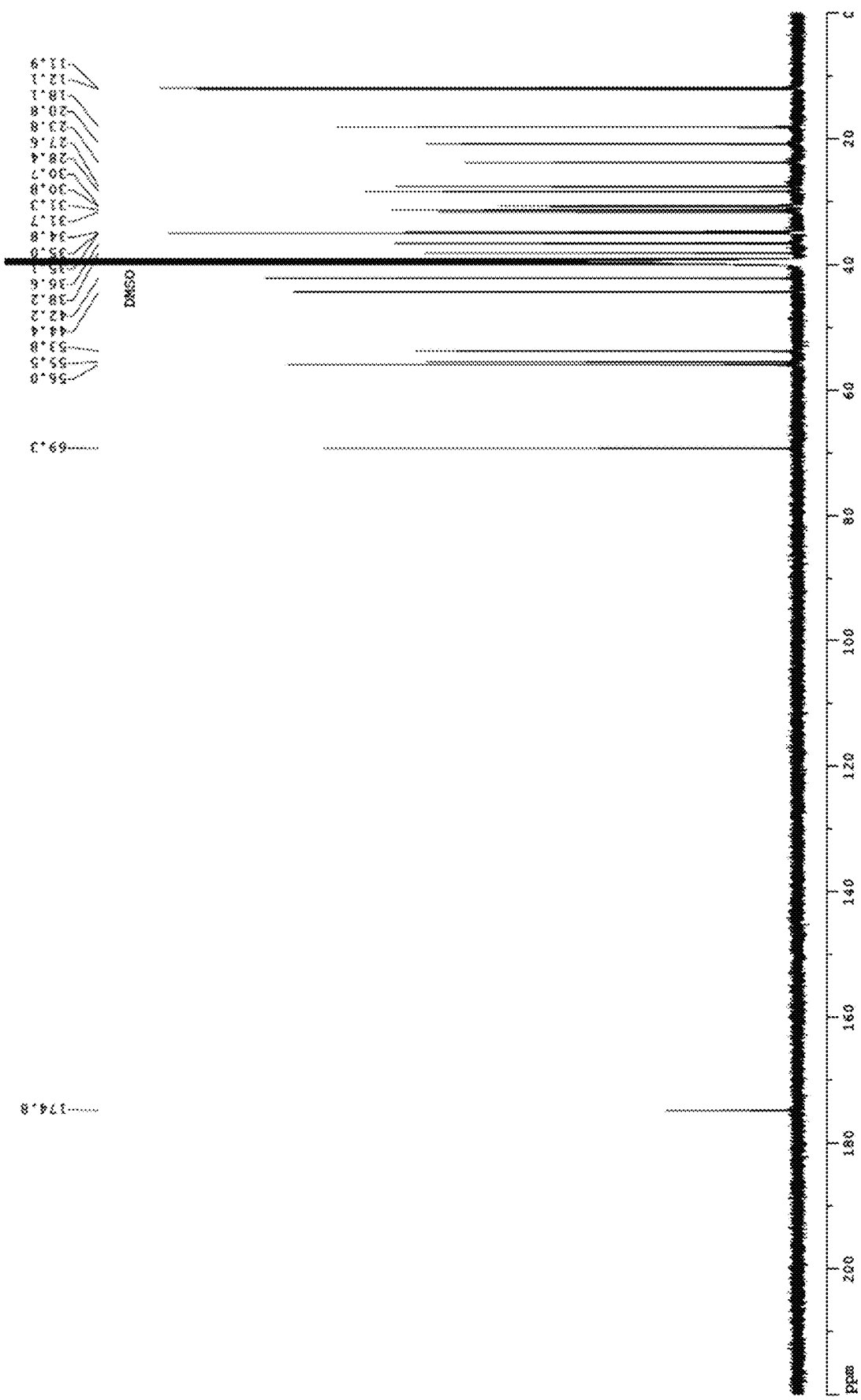

FIG. 17 shows ¹³C{¹H} NMR spectrum (151 MHz, DMSO-d6) of isoalloLCA. The compound data and spectrum of isoalloLCA are representative of five independent synthesis experiments.

Figure 18:
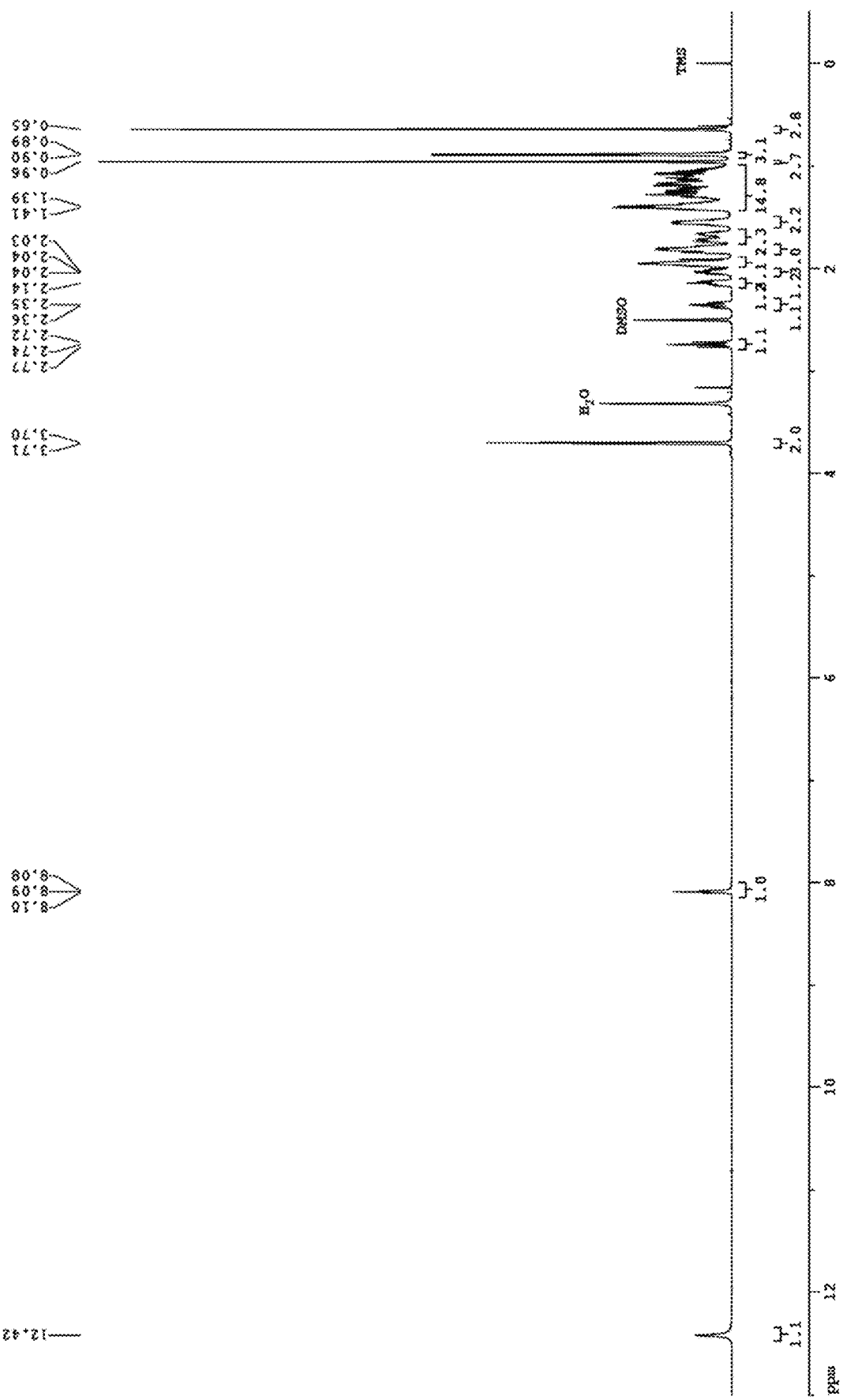

FIG. 18 shows ¹H NMR spectrum (600 MHz, DMSO-d6) of glyco-3-oxoLCA. The compound data and spectrum of glyco-3-oxoLCA are representative of one synthesis experiment.

Figure 19:
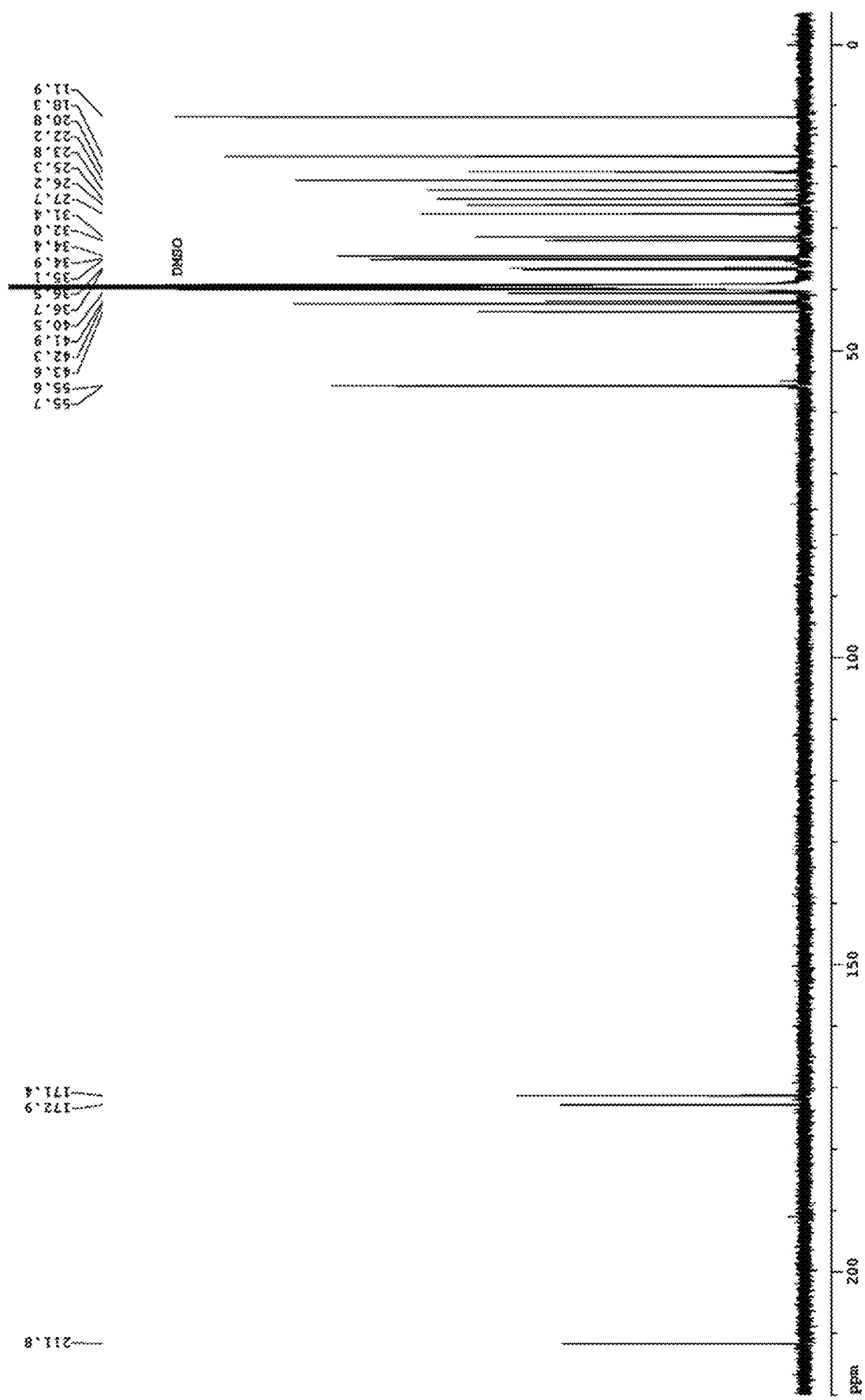

FIG. 19 shows $^{13}C\{^1H\}$ NMR spectrum (151 MHz, DMSO-d6) of glyco-3-oxoLCA. The compound data and spectrum of glyco-3-oxoLCA are representative of one synthesis experiment.

Figure 20:
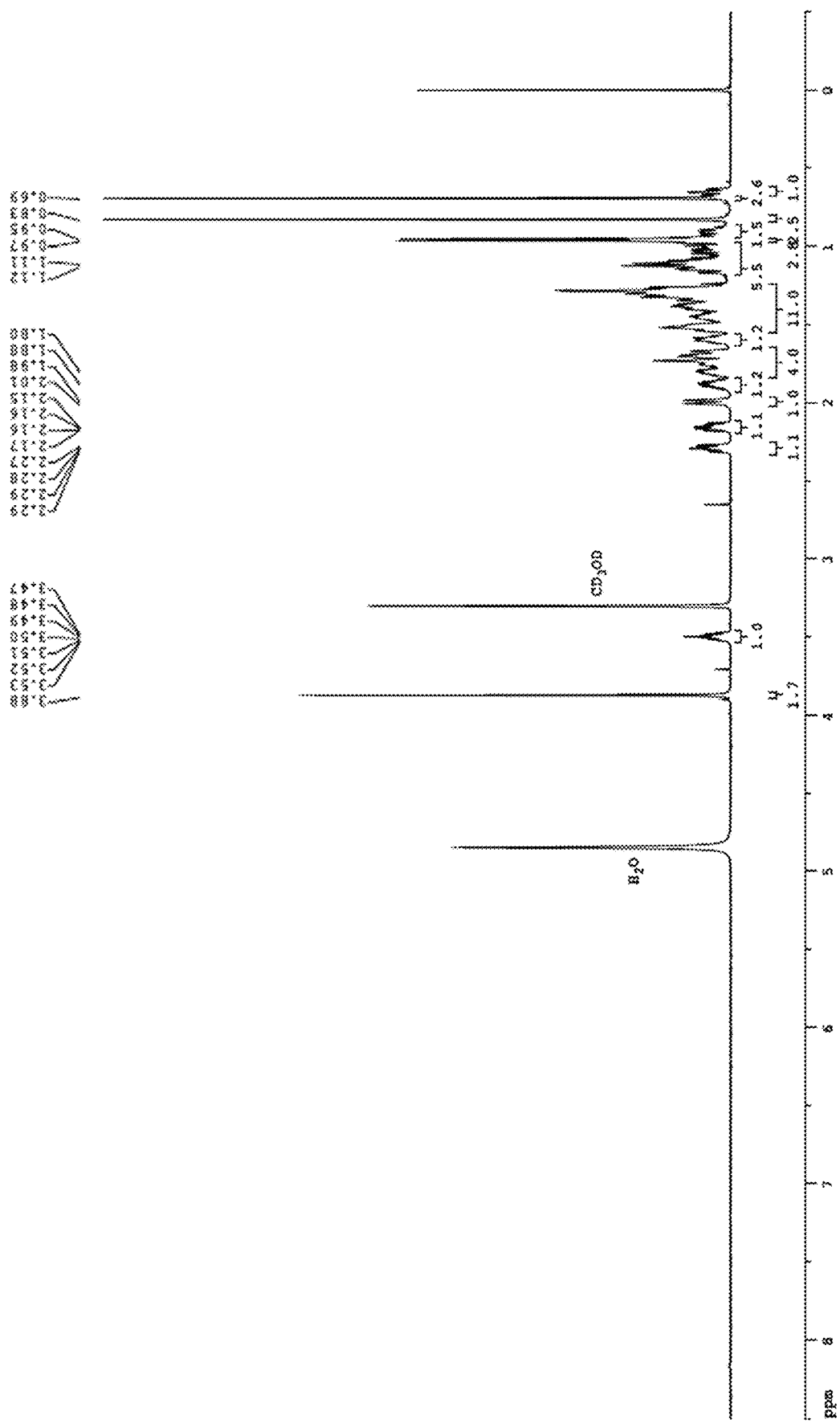

FIG. 20 shows $^1H$ NMR spectrum (600 MHz, $CD_3OD$) of glyco-isoalloLCA. The compound data and spectrum of glycoisoalloLCA are representative of one synthesis experiment.

Figure 21:
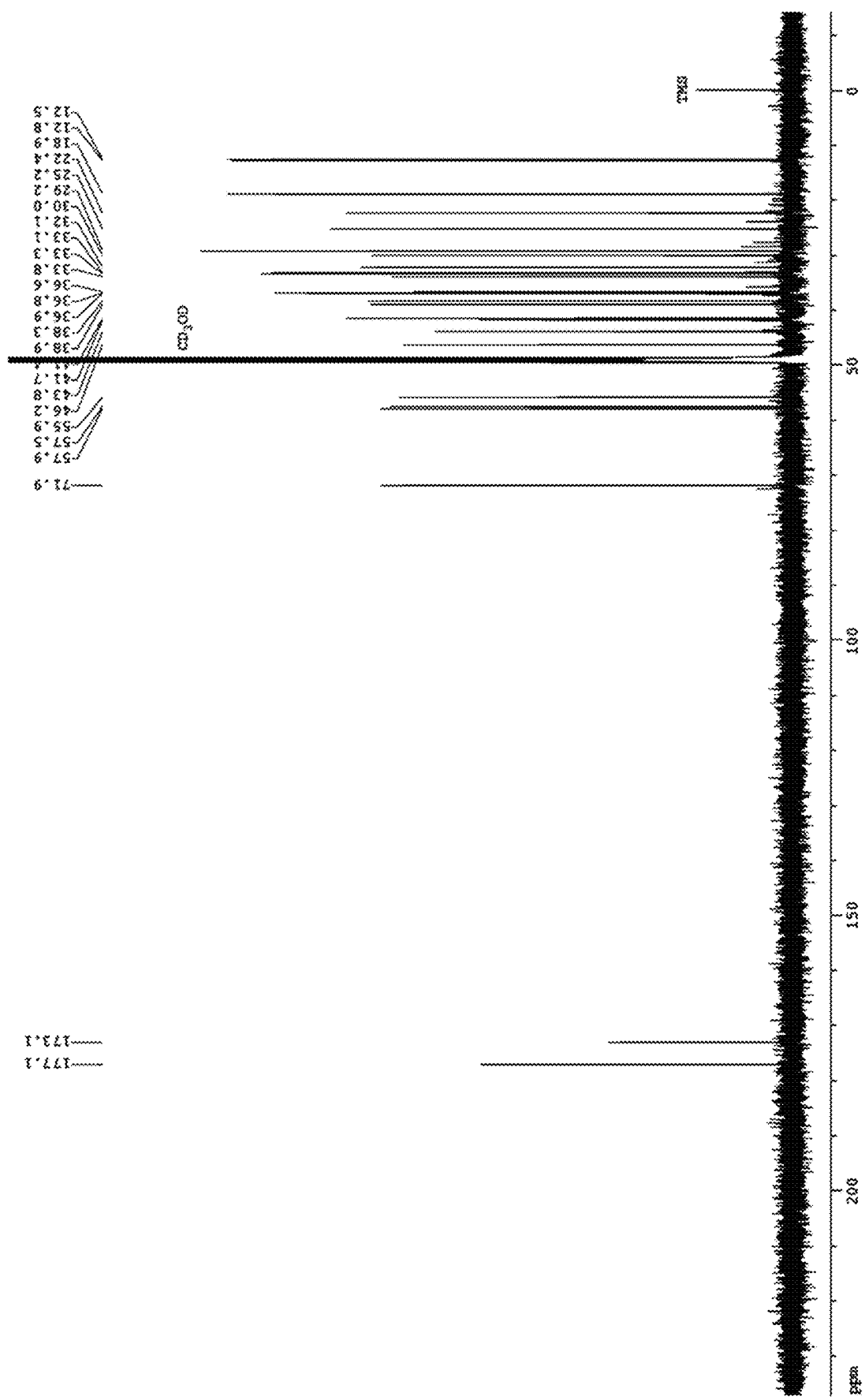

FIG. 21 shows $^{13}C\{^1H\}$ NMR spectrum (151 MHz, $CD_3OD$) of glyco-isoalloLCA. The compound data and spectrum of glycoisoalloLCA are representative of one synthesis experiment.

DETAILED DESCRIPTION OF THE INVENTION

Tregs exist in various mammalian tissues, and are most abundant in the small and large intestines, where a large number of commensal bacteria co-exist with host immune cells, separated by a monolayer of epithelial cells. Several groups have reported that particular types of gut-residing bacteria increase Treg cell numbers in the large intestine. The present inventors reasoned that microbial metabolites in the large intestine might directly act on T cells and increase Treg differentiation. After synthesis mediated by host enzymes in the liver, milligrams of bile acids are secreted into the gut lumen and contribute to the solubilization of lipid nutrients. These host-derived bile acids, primary bile acids, are re-circulated to the liver via the portal vein accessed from the terminal ileum. Those transferred to the large intestine are further modified by gut-residing bacteria and become more hydrophobic secondary bile acids.

To determine if bile acids influence T cell functions, the present inventors performed a small-scale screening assay with a small molecule library comprising secondary bile acids with in vitro Treg differentiation as a read-out. Naïve CD4$^+$ T lymphocytes were sorted from wild-type B6 mice and cultured in the presence of a TCR stimulus, interleukin 2 (IL-2), and different amounts of TGFβ (optimized for Treg differentiation). Treg differentiation was quantified at the single cell level by staining with an antibody specific for FoxP3, followed by flow cytometry analysis. Retinoic acid, a known enhancer of Treg differentiation, was used as a positive control. After testing approximately thirty bile acids at various concentrations, the present inventors found that iso-allo-lithocholic acid (iso-allo-LCA) potentiated Treg differentiation at low (0.01 or 0.1 ng/ml), but not at high (1 ng/ml) TGFβ concentration. For example, a five-fold (at 0.1 ng/ml) or twenty-fold (at 0.01 ng/ml) increase in the number of FoxP3$^+$ CD4 T cells was detected in the presence of iso-allo-LCA, compared to DMSO control.

In sum, the compounds identified herein as having Treg promoting properties may be used to increase Treg cell numbers both in vitro and in vivo and could have clinical implications in treating various autoimmune diseases and, for example, GVHD by promoting Treg responses in vivo and by improving the efficacy of Treg cell therapy. Iso-allo-LCA also serves as a chemical template on which basis to design other compounds having improved potency by performing structure-activity relationship (SAR) analyses. Identification of in vivo active metabolites of iso-allo-LCA may also be instructive with regard to the identification, development, and design of compounds having improved properties with regard to promoting Treg differentiation and/or activity.

Definitions

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. It should be further understood that the terms "groups" and "radicals" can be considered interchangeable when used herein.

"Acyl" refers to a radical —C(O)R$^{20}$, where R$^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —NR$^{21}$C(O)R$^{22}$, where R$^{21}$ is hydrogen, alkyl, cycloalkyl, cycloheteroalkyl, aryl, arylalkyl, heteroalkyl, heteroaryl, heteroarylalkyl and R$^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)R$^{23}$ where R$^{23}$ is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S (O)—, aryl-S(O)—, alkyl-S(O)$_2$— and aryl-S(O)$_2$—.

"Alkoxy" refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NR$^{25}$C(O)OR$^{26}$, where R$^{25}$ is hydrogen, alkyl, aryl or cycloalkyl, and R$^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group $R^{27}$—C(O)—, where $R^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR$^{28}$R$^{29}$, wherein each of R$^{28}$ and R$^{29}$ are independently selected from hydrogen and alkyl.

"Arylamino" refers to the group aryl-NR$^{30}$R$^{31}$, wherein each of R$^3$ and R$^{31}$ are independently selected from hydrogen, aryl and heteroaryl.

"Alkoxyamino" refers to a radical —N(H)OR$^{32}$ where R$^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —NR$^{33}$R$^{34}$ where R$^{33}$ represents an alkyl or cycloalkyl group and R$^{34}$ is an aryl as defined herein.

"Alkylsulfonyl" refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R$^{35}$ where R$^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —$SR^{35}$ where $R^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —$NH_2$.

"Substituted amino" includes those groups recited in the definition of "substituted" herein, and particularly refers to the group —$N(R^{36})_2$ where each $R^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —$N(R^{36})_2$ is an amino group.

"Aminocarbonyl" refers to the group —$C(O)NR^{37}R^{37}$ where each $R^{37}$ is independently hydrogen, alkyl, aryl and cycloalkyl, or where the $R^{37}$ groups are joined to form an alkylene group.

"Aminocarbonylamino" refers to the group —$NR^{38}C(O)NR^{38}R^{38}$ where each $R^{38}$ is independently hydrogen, alkyl, aryl or cycloalkyl, or where two R groups are joined to form an alkylene group.

"Aminocarbonyloxy" refers to the group —$OC(O)NR^{39}R^{39}$ where each $R^{39}$ is independently hydrogen, alkyl, aryl or cycloalky, or where the R groups are joined to form an alkylene group.

"Arylalkyloxy" refers to an —O-arylalkyl radical where arylalkyl is as defined herein.

"Arylamino" means a radical —$NHR^{40}$ where $R^{40}$ represents an aryl group as defined herein.

"Aryloxycarbonyl" refers to a radical —C(O)—O-aryl where aryl is as defined herein.

"Arylsulfonyl" refers to a radical —$S(O)_2R^{41}$ where $R^{41}$ is an aryl or heteroaryl group as defined herein.

"Azido" refers to the radical —$N_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —$C(O)N(R^{42})_2$ where each $R^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Cycloalkoxy" refers to the group —$OR^{43}$ where $R^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-$S(O)_2$— and aryl-$S(O)_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —$NR^{44}R^{45}$ where $R^{44}$ and $R^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C=C)—.

"Ethylene" refers to substituted or unsubstituted —(C=C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{46}$, —O, =O, —OR$^{46}$, —SR$^{46}$, —S—, =S, —NR$^{46}$R$^{47}$, =NR$^{46}$, —CX$_3$—CF$_3$, —CN, —OCN, —SCN, —NO, —NO$_2$, =N$_2$, —N$_3$, —S(O)$_2$O—, —S(O)$_2$OH, —S(O)$_2$R$^{46}$, —OS(O$_2$)O—, —OS(O)$_2$R$^{46}$, —P(O)(O$^-$)$_2$, —P(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O—, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

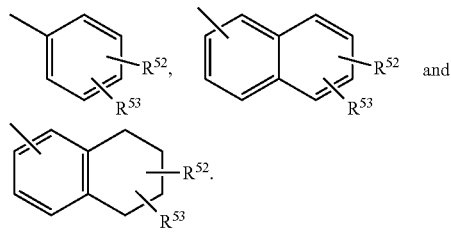

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^5$, NR$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

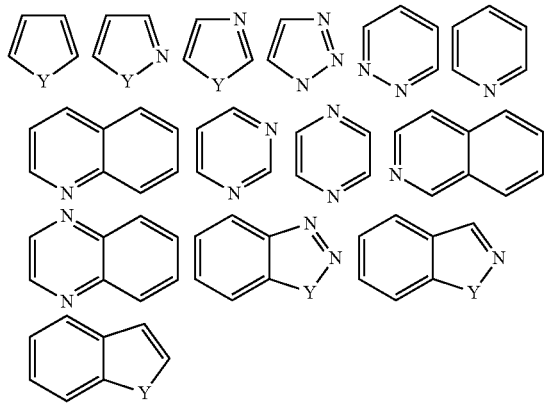

wherein each Y is selected from carbonyl, N, NR$^{58}$, O, and S; and R$^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

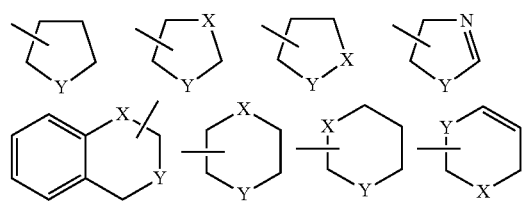

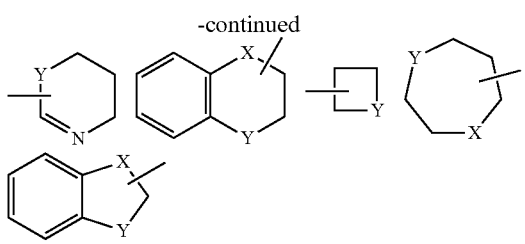

wherein each X is selected from CR$^{58}_2$, NR$^{58}$, O and S; and each Y is selected from NR$^{58}$, O and S; and R$^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

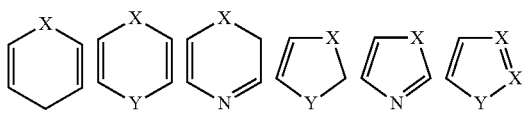

wherein each X is selected from CR$^{58}_2$, NR$^{58}$, O and S; and each Y is selected from carbonyl, N, NR$^{58}$, O and S; and R$^{58}$ is independently hydrogen, alkyl, cycloalkyl, cycloheteroalkyl, aryl, heteroaryl, heteroalkyl or the like.

Examples of representative aryl having hetero atoms containing substitution include the following:

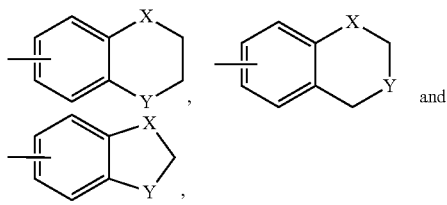

wherein each X is selected from C—R$^{58}_2$NR$^{58}$, O and S; and each Y is selected from carbonyl, NR$^{58}$, O and S; and R$^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an R$^4$ in a R$^4$C group present as substituents directly on A, B, W, Y or Z of the compounds of this invention or may be present as a substituent in the "substituted" aryl and aliphatic groups present in the compounds.

Examples of hetero substituents include:
halo,
—NO$_2$, —NH$_2$, —NHR$^{59}$, —N(R$^{59}$)$_2$,
—NRCOR, —NR$^{59}$SOR$^{59}$, —NR$^{59}$SO$_2$R$^{59}$, OH, CN,
—CO$_2$H,
—R$^{59}$—OH, —O—R$^{59}$, —COOR$^{59}$,
—CON(R$^{59}$)$_2$, —CONROR$^{59}$,
—SO$_3$H, —R$^{59}$—S, —SO$_2$N(R$^{59}$)$_2$,
—S(O)R$^{59}$, —S(O)$_2$R$^{59}$ wherein each R$^{59}$ is independently an aryl or aliphatic, optionally with substitution. Among hetero substituents containing R$^{59}$ groups, preference is given to those materials having aryl and alkyl R$^{59}$ groups as defined herein. Preferred hetero substituents are those listed above.

"Hydrogen bond donor" group refers to a group containing O—H, or N—H functionality. Examples of "hydrogen bond donor" groups include —OH, —NH$_2$, and —NH—R$^{59a}$ and wherein R$^{59a}$ is alkyl, cycloalkyl, aryl, or heteroaryl.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —SR$^{60}$ where R$^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as R$^{61}$—(O$_2$)S— wherein R$^{61}$ is any substituent described herein. "Aminosulfonyl" or "Sulfonamide" refers to the radical H$_2$N(O$_2$)S—, and "substituted aminosulfonyl" "substituted sulfonamide" refers to a radical such as R$^{62}_2$N(O$_2$)S— wherein each R$^{62}$ is independently any substituent described herein.

"Sulfone" refers to the group —SO$_2$R$^{63}$. In particular embodiments, R$^{63}$ is selected from H, lower alkyl, alkyl, aryl and heteroaryl.

"Thioaryloxy" refers to the group —SR$^{64}$ where R$^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes mammals (including, e.g., mice, rats, pigs, cattle, dogs, cats, horses, and primates), and more particularly humans. The terms "human," "patient" and "subject" may be used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

As used herein, the term "operably linked" refers to a regulatory sequence capable of mediating the expression of a coding sequence and which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "transform", "transfect", or "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, which are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Methods and the Compounds

The present invention provides methods for promoting differentiation of T regulatory (Treg) lymphocytes and/or suppressing Th17 cells, which comprises contacting naïve CD4+ T lymphocytes with an effective amount of a compound according to formula I.

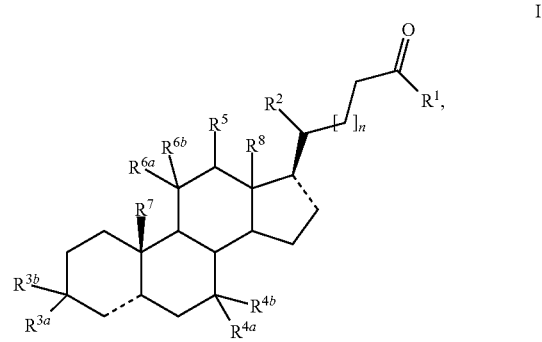

I

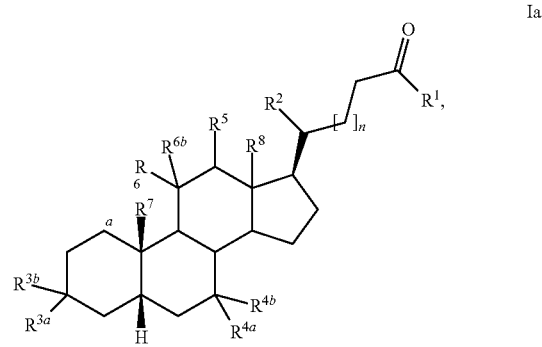

Ia

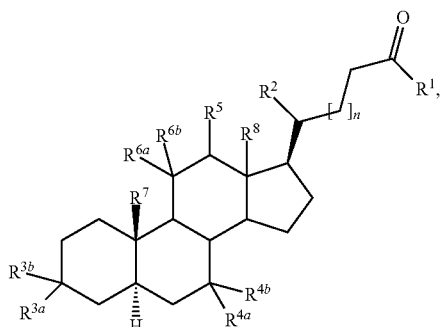
Ib

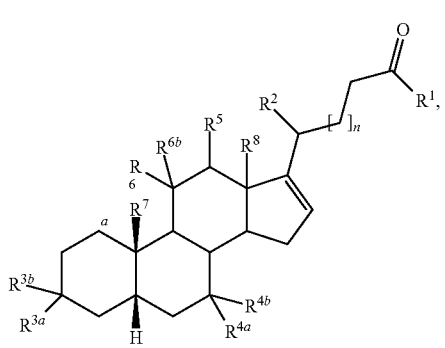
Ic

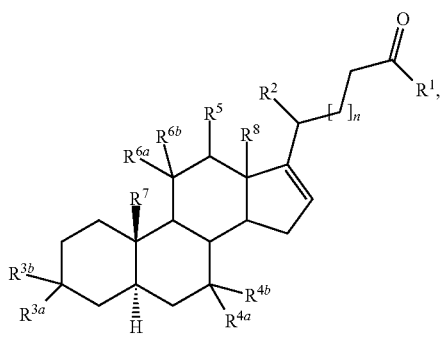
Id

Ie

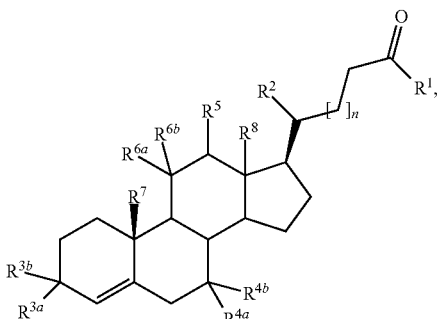
If

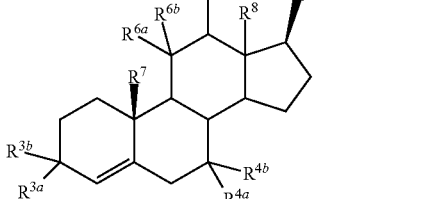
Ig

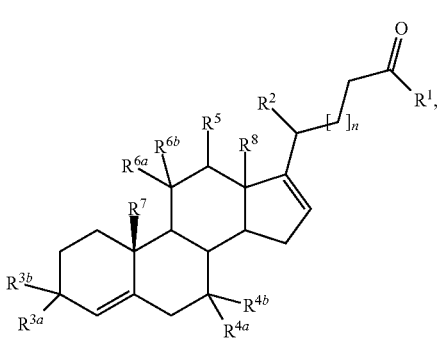
Ih wherein:
$R^1$ is substituted or unsubstituted alkyl, substituted or unsubstituted hydroxyl, or substituted or unsubstituted amino;
$R^2$ is H, alkyl, or substituted or unsubstituted cycloalkyl;
$R^{3a}$ is —OH, —OC(O)$R^{3c}$, or —O—S(O)$_2$OH; $R^{3c}$, is substituted or unsubstituted alkyl;
$R^{3b}$ is selected from H, substituted or unsubstituted alkyl, substituted or unsubstituted alkenyl, or substituted or unsubstituted alkynyl;
or $R^{3a}$ and $R^{3b}$ are joined to form an oxo (=O) group;
each $R^{4a}$, $R^{4b}$, $R^5$, $R^{6a}$ and $R^{6b}$ is independently H, OH, substituted or unsubstituted amino, or substituted or unsubstituted alkyl;
or each $R^{4a}$ and $R^{4b}$ or $R^{6a}$ and $R^{6b}$ are joined to form an oxo (=O) group;
$R^7$ is H or substituted or unsubstituted alkyl;
$R^8$ is H or substituted or unsubstituted alkyl;
and n is independently 0, 1, 2, 3, 4, 5, or 6;
and each dotted bond is independently a single or a double bond;
or a pharmaceutically acceptable salt, solvate, hydrate, prodrug, or stereoisomer, thereof, or a combination thereof. Such methods may be performed in vitro or in vivo. In one embodiment, at least one compound of formula I is administered to a subject in need thereof to promote Treg differentiation in the subject. In another embodiment, naive CD4+ T lymphocytes are contacted in vitro to generate a population of Treg cells, which population is subsequently administered to a subject in need thereof. In vitro culturing of cells may also be referred to as having been performed ex vivo. Also encompassed herein are embodiments wherein Treg cells are isolated from a subject and contacted ex vivo with a compound of formula I.

In one embodiment, with respect to the compounds of formula I, the compound is other than ursodeoxycholic acid.

In certain aspects, the present invention provides a method for preventing, treating or ameliorating in a mammal a disease or condition that is causally related to excessive or uncontrolled immune responses (e.g., autoimmune or inflammatory diseases/conditions) and/or insufficient Treg responses in vivo, which comprises administering to the mammal an effective disease-treating or condition-treating amount of a compound according to formula I; or a pharmaceutically acceptable salt, solvate or prodrug thereof, or stereoisomers, isotopic variants and tautomers thereof. Such methods are directed to promoting Treg differentiation and/or activity in the mammal.

In an embodiment, this disclosure provides compositions and methods for increasing the level/activity of Tregs. In an embodiment, this disclosure provides compositions and methods for reducing the level/activity of Th17 cells.

In an embodiment, this disclosure provides compositions and methods for increasing the ratio of the level of activity of regulatory T cells (such as Treg) to the level of activity of pro-inflammatory T cells (such as Th17). The ratio may be increased by increasing Treg activity levels, decreasing Th17 cell activity levels or both. The activity of cells may be increased or decreased by increasing or decreasing their numbers or enhancing or reducing their function.

In one embodiment, the compound is according to formula IIa, IIb, IIc, or IId:

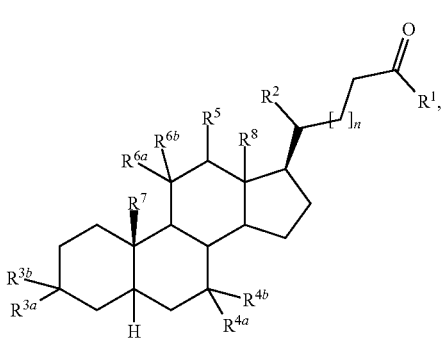

IIa

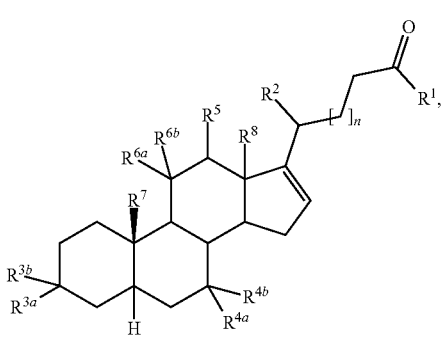

IIb

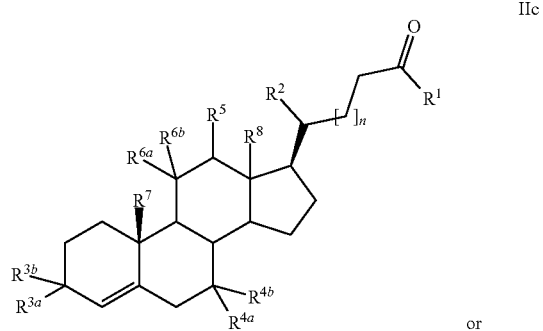

IIc or

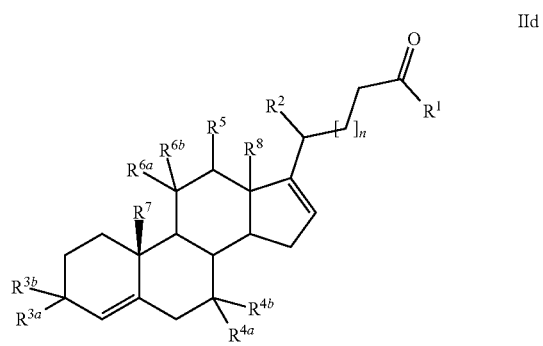

IId and wherein $R^1$, $R^2$, $R^{3a}$, $R^{3b}$, $R^{4a}$, $R^{4b}$, $R^5$, $R^{6a}$, $R^{6b}$, $R^7$, $R^8$, and n are as described for formula I; or a pharmaceutically acceptable salt, solvate, hydrate, prodrug, or stereoisomer, thereof, or a combination thereof.

In one embodiment, each of $R^{4a}$, and $R^{4b}$ is independently H, or OH.

In another embodiment, one of $R^{4a}$, and $R^{4b}$ is H, and the other is OH.

In another embodiment, $R^{4a}$ and $R^{4b}$ are joined to form an oxo (=O) group.

In another embodiment, each of $R^{4a}$, and $R^{4b}$ is H.

In one embodiment, $R^5$ is OH.

In another embodiment, $R^5$ is H.

In another embodiment, $R^8$ is methyl.

In one embodiment, the compound is according to formula IIIa, IIIb, IIIc, or IIId.

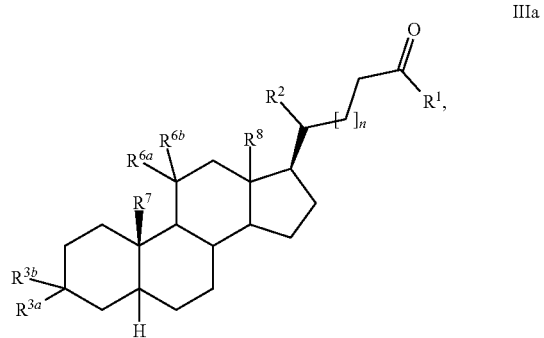

IIIa

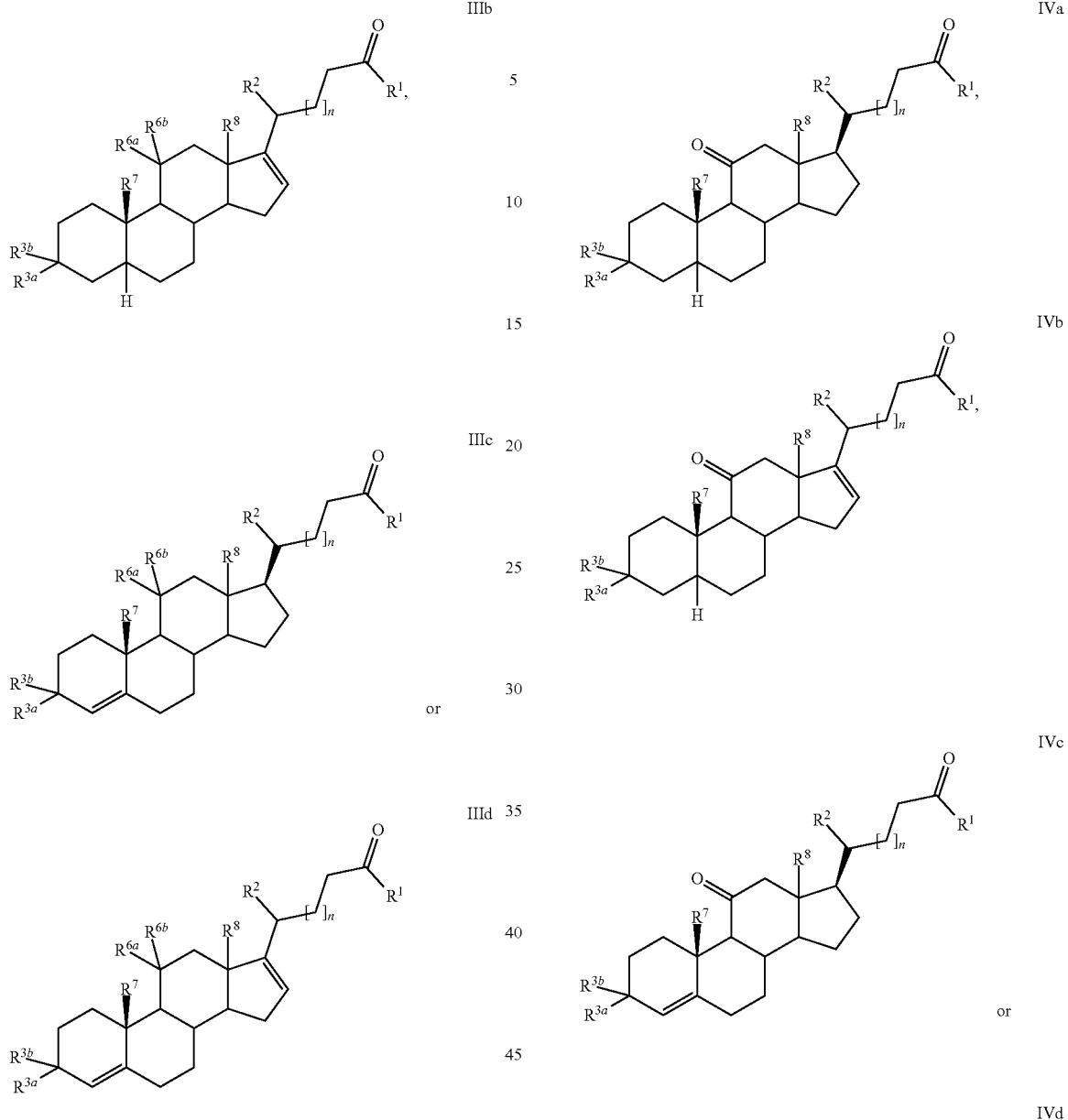

and wherein $R^1$, $R^2$, $R^{3a}$, $R^{3b}$, $R^{6a}$, $R^{6b}$, $R^7$, $R^8$, and n are as described for formula I; or a pharmaceutically acceptable salt, solvate, hydrate, prodrug, or stereoisomer, thereof, or a combination thereof.

In one embodiment, each of $R^{6a}$, and $R^{6b}$ is independently H, OH, amino, or dialkylamino.

In another embodiment, one of $R^{6a}$, and $R^{6b}$ is H; and the other is OH, amino, or dialkylamino.

In another embodiment, one of $R^{6a}$, and $R^{6b}$ is H; and the other is OH, amino, or dimethylamino.

In another embodiment, $R^{6a}$ and $R^{6b}$ are joined to form an oxo (=O) group.

In another embodiment, each of $R^{6a}$, and $R^{6b}$ is H.

In another embodiment, $R^8$ is methyl.

In one embodiment, the compound is according to formula IVa, IVb, IVc, or IVd.

and wherein $R^1$, $R^2$, $R^{3a}$, $R^{3b}$, $R^7$, $R^8$, and n are as described for formula I; or a pharmaceutically acceptable salt, solvate, hydrate, prodrug, or stereoisomer, thereof, or a combination thereof.

In one embodiment, the compound is according to formula Va, Vb, Vc, or Vd:

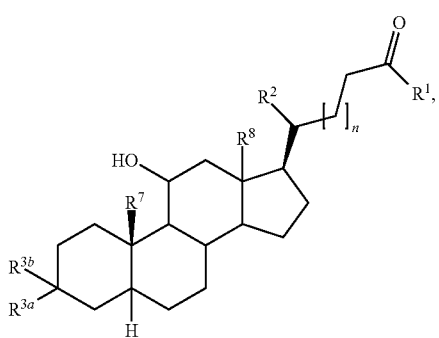 Va

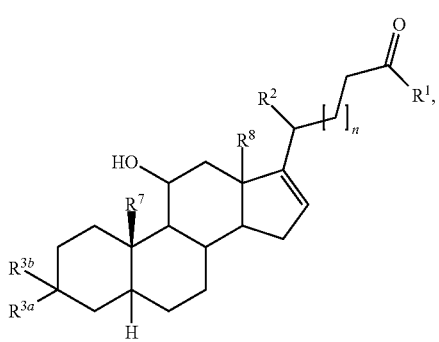 Vb

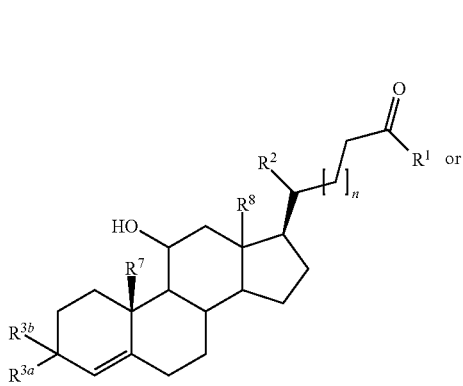 Vc

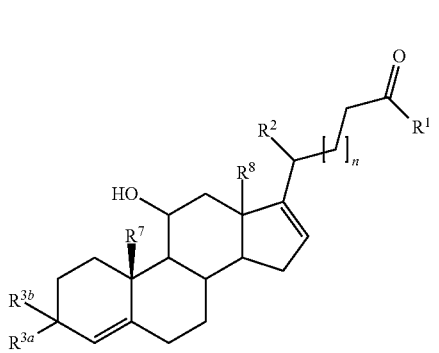 Vd and wherein R¹, R², R³ᵃ, R³ᵇ, R⁷, R⁸, and n are as described for formula I; or a pharmaceutically acceptable salt, solvate, hydrate, prodrug, or stereoisomer, thereof, or a combination thereof.

In one embodiment, the compound is according to formula VIa, VIb, VIc, or VId:

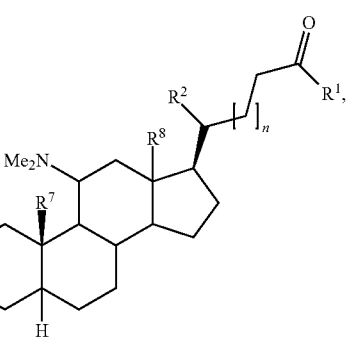 VIa

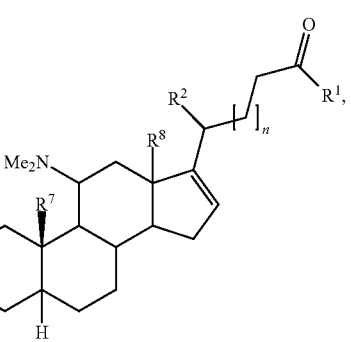 VIb

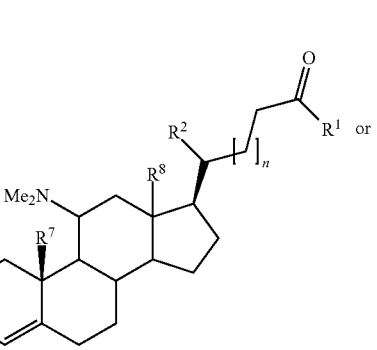 VIc

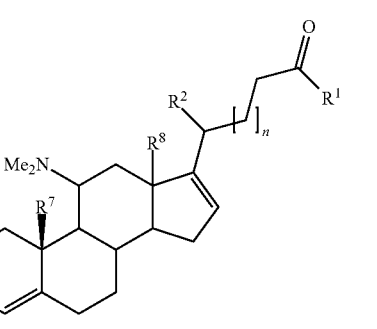 VId and wherein R¹, R², R³ᵃ, R³ᵇ, R⁷, R⁸, and n are as described for formula I; or a pharmaceutically acceptable salt, solvate, hydrate, prodrug, or stereoisomer, thereof, or a combination thereof.

In one embodiment, the compound is according to formula VIIa, VIIb, VIIc, or VIId:

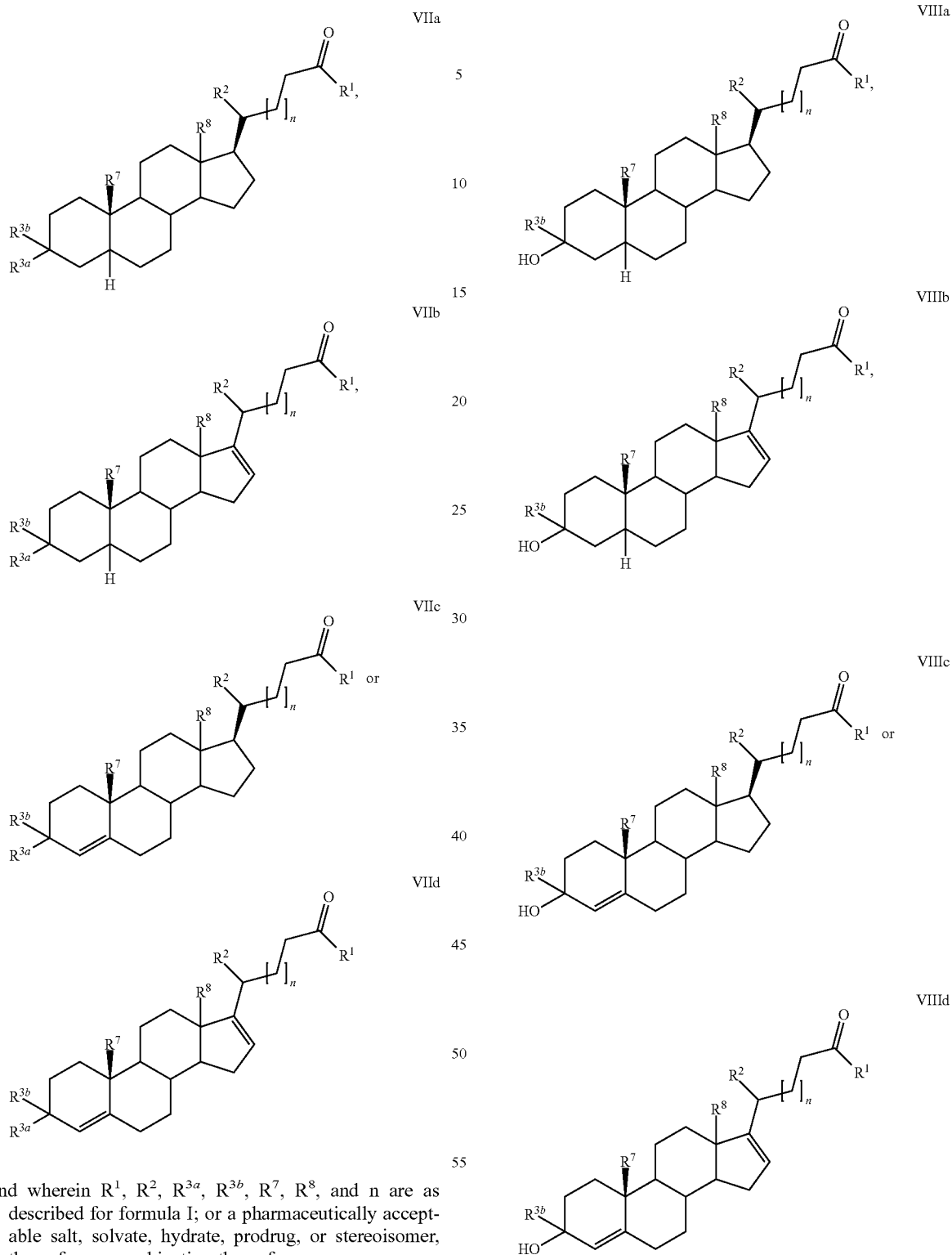

and wherein $R^1$, $R^2$, $R^{3a}$, $R^{3b}$, $R^7$, $R^8$, and n are as described for formula I; or a pharmaceutically acceptable salt, solvate, hydrate, prodrug, or stereoisomer, thereof, or a combination thereof.

In one embodiment, $R^{3a}$ is OH.

In another embodiment, $R^{3a}$ and $R^{3b}$ are joined to form an oxo (=O) group.

In another embodiment, $R^8$ is methyl.

In one embodiment, the compound is according to formula VIIIa, VIIIb, VIIIc, or VIIId:

and wherein $R^1$, $R^2$, $R^{3b}$, $R^7$, $R^8$, and n are as described for formula I; or a pharmaceutically acceptable salt, solvate, hydrate, prodrug, or stereoisomer, thereof, or a combination thereof.

In another embodiment, the compound is according to formula IXa, IXb, IXc, or IXd:

IXa

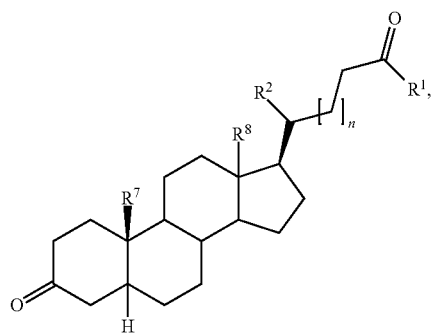

IXb

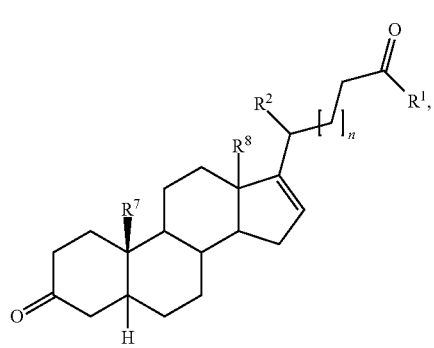

IXc

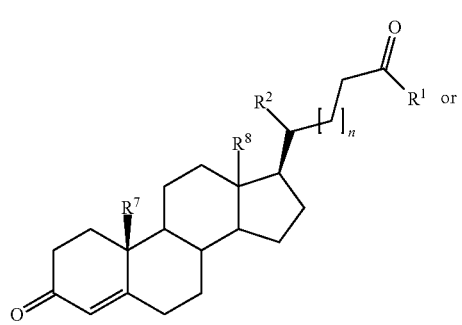

IXd

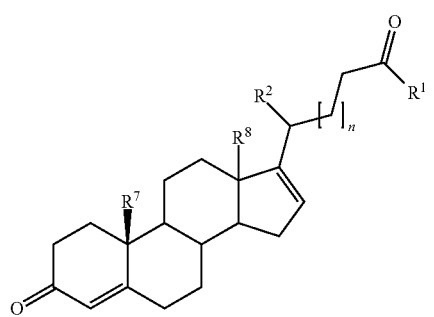

and wherein $R^1$, $R^2$, $R^7$, $R^8$, and n are as described for formula I; or a pharmaceutically acceptable salt, solvate, hydrate, prodrug, or stereoisomer, thereof, or a combination thereof.

In one embodiment, when the bond between $C_4$ and $C_5$ is a single bond; then the compound is a 5α-isomer.

In another embodiment, when the bond between $C_4$ and $C_5$ is a single bond; then the compound is a 5β-isomer.

In another embodiment, the compound is according to formula Xa, Xb, Xc, or Xd:

Xa

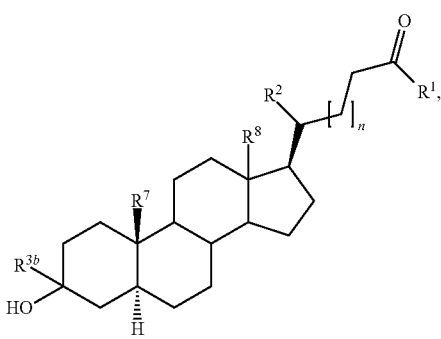

Xb

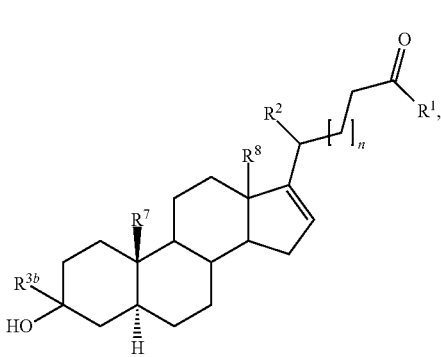

Xc

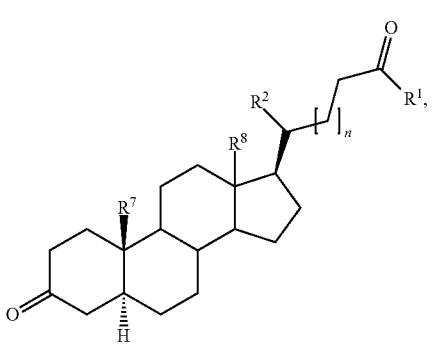

Xd

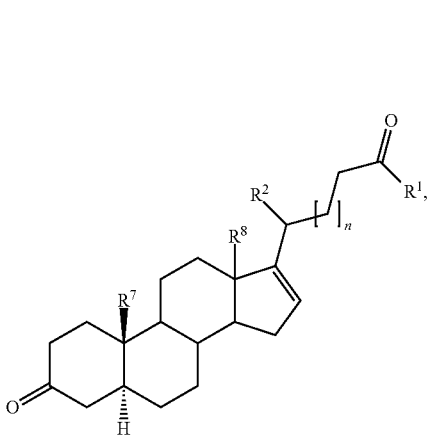

and wherein $R^1$, $R^2$, $R^{3b}$, $R^7$, $R^8$, and n are as described for formula I; or a pharmaceutically acceptable salt, solvate, hydrate, prodrug, or stereoisomer, thereof, or a combination thereof.

In a particular embodiment, the compound is iso-alloLCA
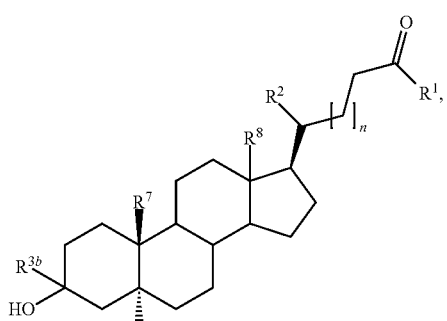
Xa
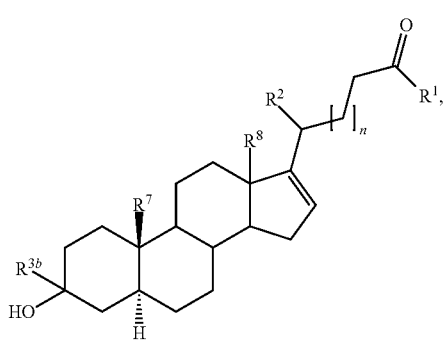
Xb
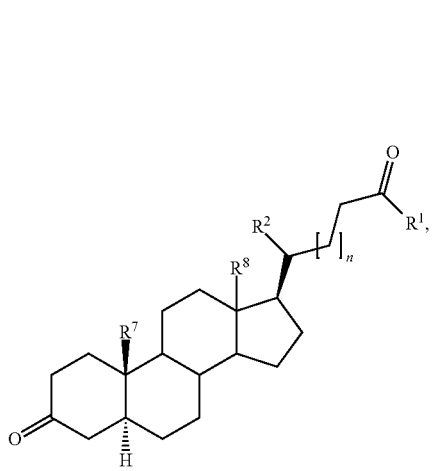
Xc
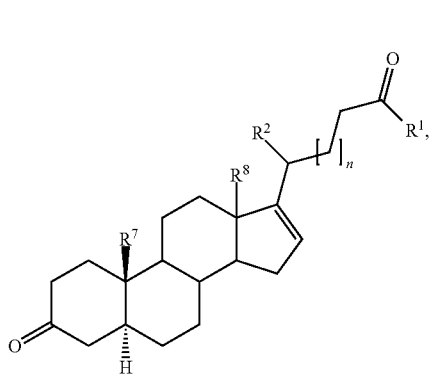
Xd
In another embodiment, the compound is according to formula XIa, XIb, XIc, or XId:
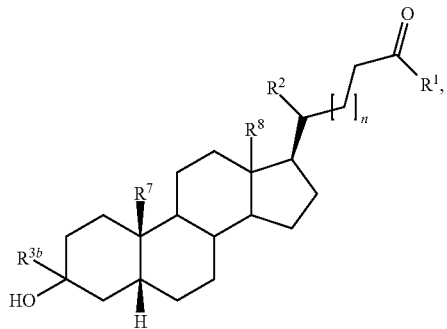
XIa
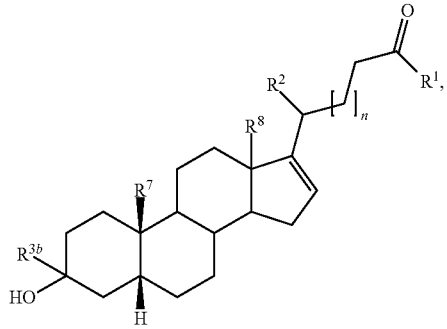
XIb
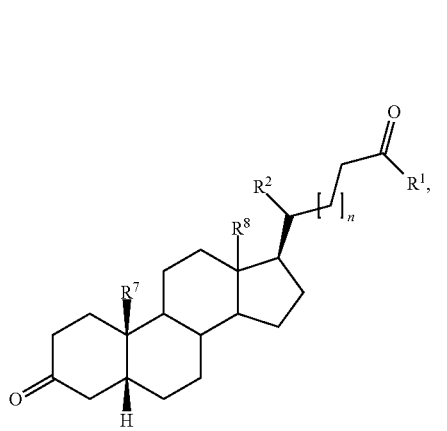
XIc
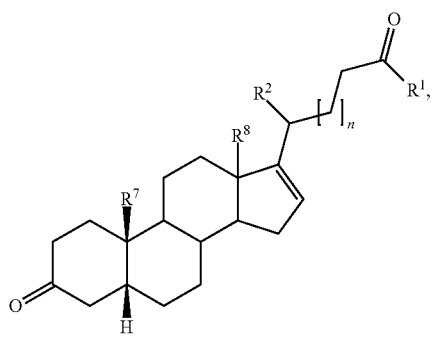
XId
and wherein $R^1$, $R^2$, $R^{3b}$, $R^7$, $R^8$, and n are as described for formula I; or a pharmaceutically acceptable salt, solvate, hydrate, prodrug, or stereoisomer, thereof, or a combination thereof.

In a particular embodiment, the compound is 3-oxoLCA

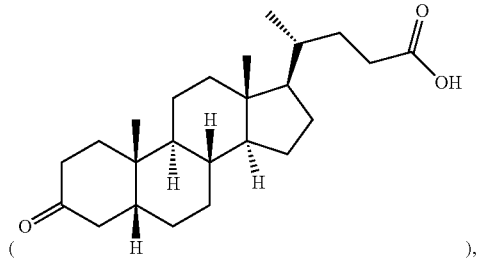

which inhibits Th17.

In one embodiment, $R^{3a}$ is at 3β-position.

In another embodiment, $R^{3a}$ is at 3α-position.

In another embodiment, the compound is according to formula XIIa, XIIb, XIIc, or XIId:

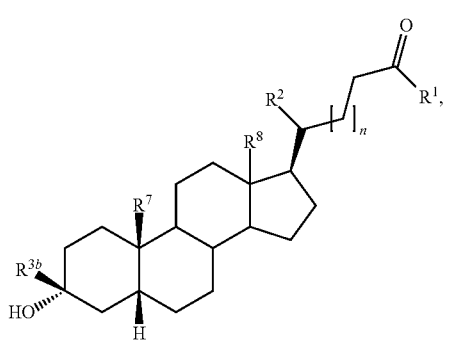

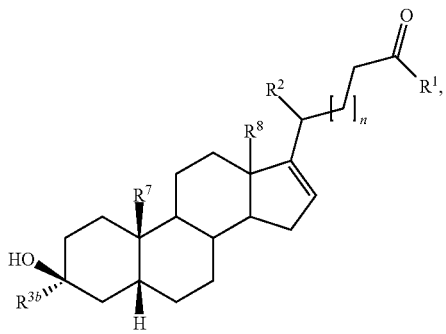

and wherein $R^1$, $R^2$, $R^{3b}$, $R^7$, $R^8$, and n are as described for formula I; or a pharmaceutically acceptable salt, solvate, hydrate, prodrug, or stereoisomer, thereof, or a combination thereof.

In one embodiment, $R^2$ is H.

In another embodiment, $R^2$ is alkyl.

In another embodiment, $R^2$ is substituted alkyl.

In another embodiment, $R^2$ is alkyl substituted with hydroxyl or substituted hydroxyl.

In another embodiment, $R^2$ is Me, Et, n-Pr, i-Pr, n-Bu, i-Bu, sec-Bu, or t-Bu.

In another embodiment, $R^2$ is cycloalkyl.

In another embodiment, $R^2$ is cyclopropyl.

In another embodiment, $R^2$ is Me.

In another embodiment, $R^8$ is methyl.

In another embodiment, the compound is according to formula XIIIa, XIIIb, XIIIc, or XIIId:

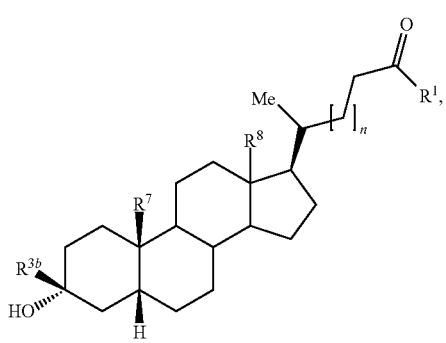

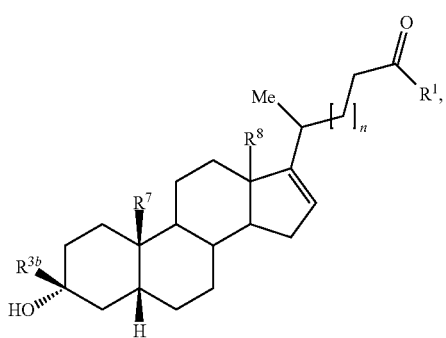

-continued

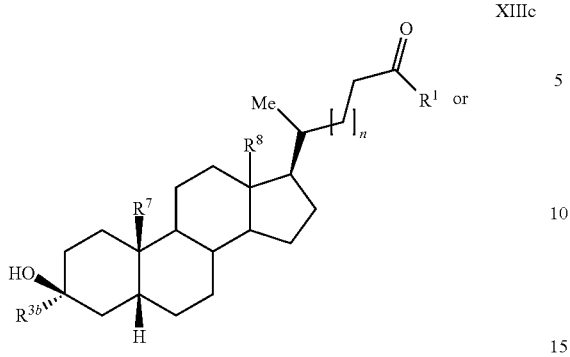

XIIIc

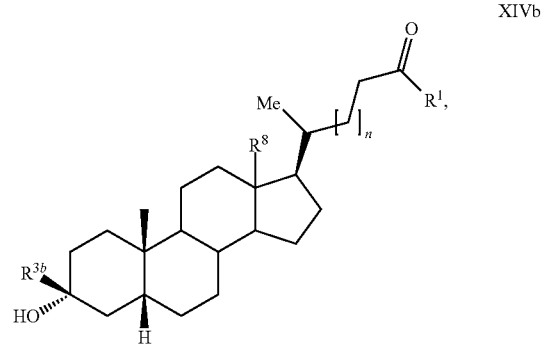

XIVb

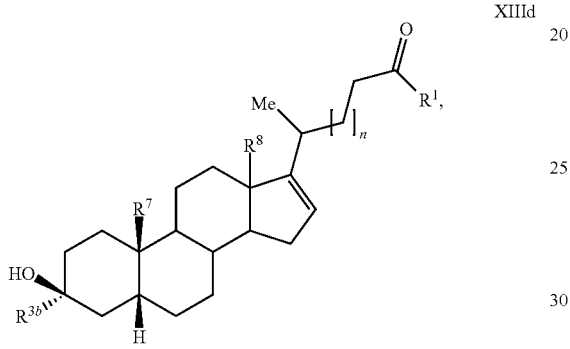

XIIId

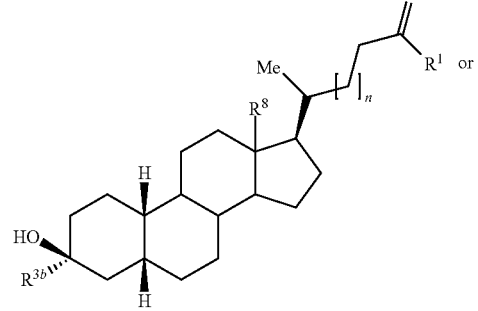

XIVc and wherein $R^1$, $R^{3b}$, $R^7$, $R^8$, and n are as described for formula I; or a pharmaceutically acceptable salt, solvate, hydrate, prodrug, or stereoisomer, thereof, or a combination thereof.

In one embodiment, $R^7$ is H.

In another embodiment, $R^7$ is alkyl.

In another embodiment, $R^7$ is substituted alkyl.

In another embodiment, $R^7$ is alkyl substituted with hydroxyl or substituted hydroxyl.

In another embodiment, $R^7$ is Me, or Et.

In another embodiment, $R^8$ is methyl.

In another embodiment, the compound is according to formula XIVa, XIVb, XIVc, or XIVd.

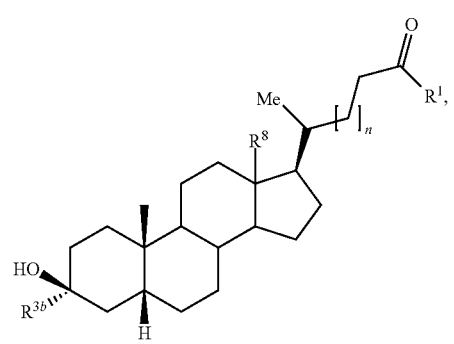

XIVd

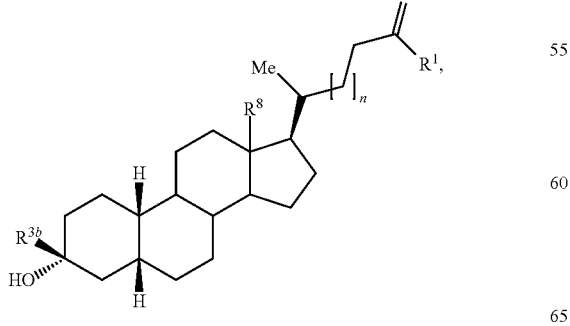

XIVa and wherein $R^1$, $R^{3b}$, $R^8$, and n are as described for formula I; or a pharmaceutically acceptable salt, solvate, hydrate, prodrug, or stereoisomer, thereof, or a combination thereof.

In one embodiment, n is 0.

In another embodiment, n is 1, 2, or 3.

In another embodiment, n is 1.

In another embodiment, $R^8$ is methyl.

In another embodiment, the compound is according to formula XVa, XVb, XVc, or XVd:

XVa
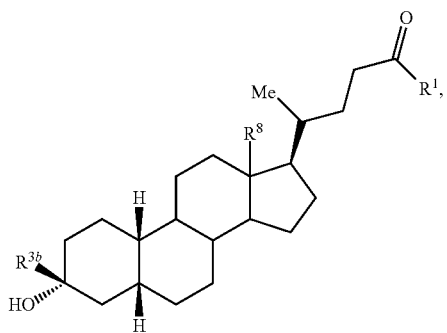

XVb
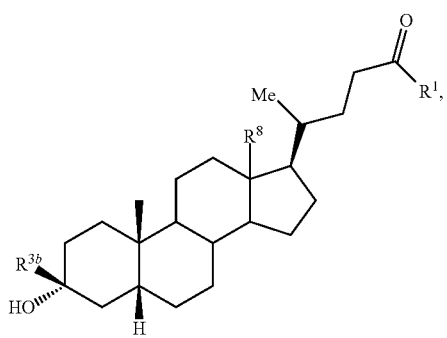

XVc
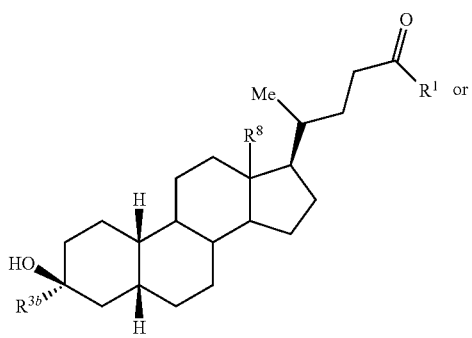

XVd
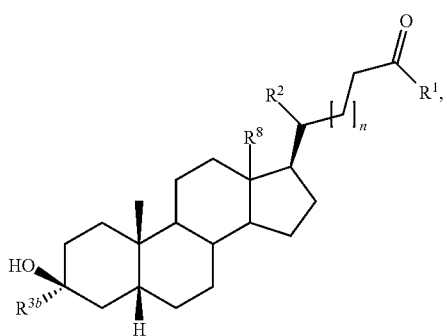

and wherein $R^1$, $R^{3b}$, and $R^8$ are as described for formula I; or a pharmaceutically acceptable salt, solvate, hydrate, prodrug, or stereoisomer, thereof, or a combination thereof.

In one embodiment, $R^1$ is substituted or unsubstituted alkyl.

In another embodiment, $R^1$ is alkyl.

In another embodiment, $R^1$ is Me, Et, n-Pr, i-Pr, n-Bu, i-Bu, sec-Bu, or t-Bu.

In another embodiment, $R^1$ is substituted or unsubstituted amino.

In another embodiment, $R^1$ is amino or dialkylamino.

In another embodiment, $R^1$ is dimethylamino or diethylamino.

In another embodiment, $R^1$ is substituted or unsubstituted hydroxyl.

In another embodiment, $R^1$ is hydroxyl or alkoxy.

In another embodiment, $R^1$ is OH, OMe, or OEt.

In another embodiment, $R^1$ is OH.

In another embodiment, the compound is according to formula XVIa, XVIb, XVIc, or XVId:

XVIa
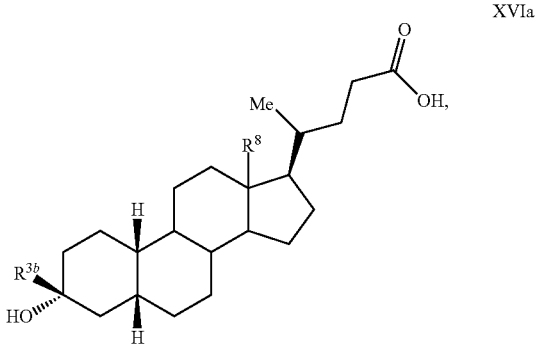

XVIb
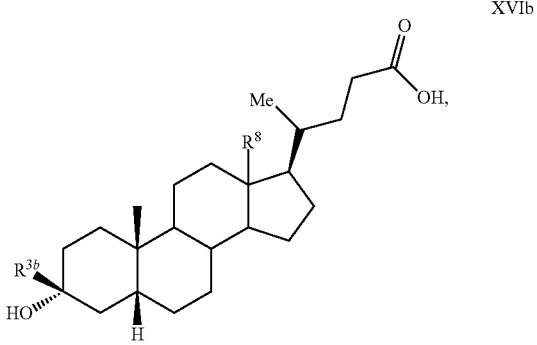

XVIc
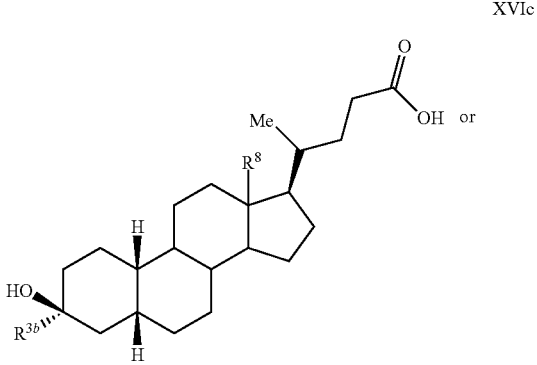

XVId
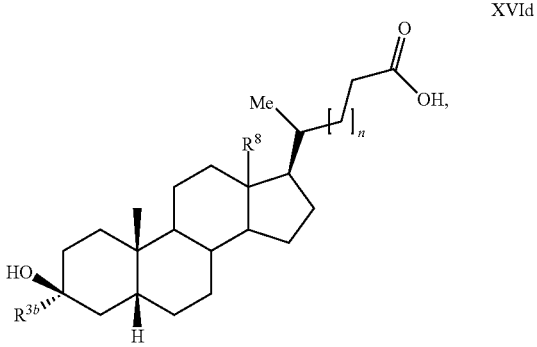

and wherein $R^{3b}$ and $R^8$ is as described for formula I; or a pharmaceutically acceptable salt, solvate, hydrate, prodrug, or stereoisomer, thereof, or a combination thereof.

In one embodiment, $R^{3b}$ is substituted or unsubstituted alkyl.

In another embodiment, $R^{3b}$ is alkyl substituted with hydroxyl or halo.

In another embodiment, $R^{3b}$ is Me, Et, n-Pr, i-Pr, n-Bu, i-Bu, sec-Bu, or t-Bu.

In another embodiment, $R^{3b}$ is chloromethyl or hydroxymethyl.

In another embodiment, $R^{3b}$ is Me.

In another embodiment, $R^{3b}$ is substituted or unsubstituted alkenyl.

In another embodiment, $R^{3b}$ is substituted or unsubstituted ethenyl or propenyl.

In another embodiment, $R^{3b}$ is substituted or unsubstituted alkynyl.

In another embodiment, $R^{3b}$ is substituted or unsubstituted ethynyl or propynyl.

In another embodiment, $R^{3b}$ is substituted or unsubstituted chloro propynyl.

In another embodiment, $R^{3b}$ is H.

In another embodiment, $R^8$ is methyl.

In another embodiment, the compound is according to formula XVIIa, XVIIb, XVIIc, or XVIId:

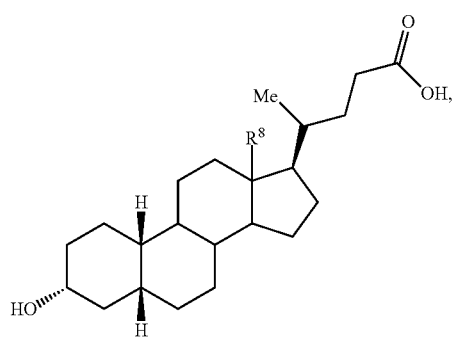

XVIIa

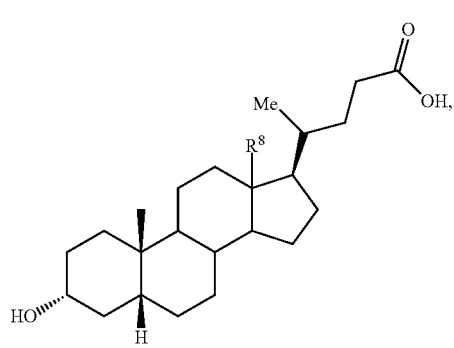

XVIIb

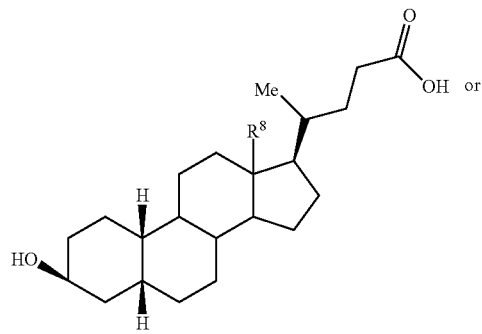

XVIIc

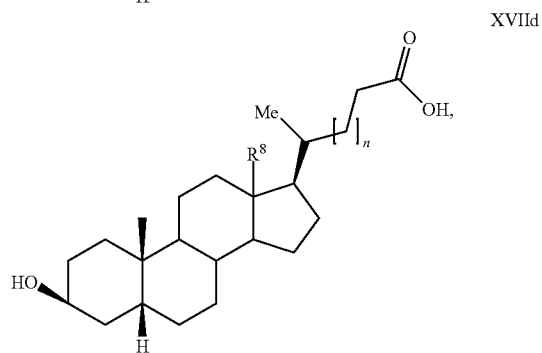

XVIId and wherein $R^{3b}$ and $R^8$ is as described for formula I; or a pharmaceutically acceptable salt, solvate, hydrate, prodrug, or stereoisomer, thereof, or a combination thereof.

In a particular embodiment, the compound according to formula I is allo-lithocholic acid (alloLCA) or iso-allo-lithocholic acid (iso-alloLCA).

In certain embodiments, the invention provides pharmaceutical compositions of compounds described herein. In certain embodiments, the invention provides pharmaceutical compositions of compounds according to formula I-XVIId.

In one embodiment, the pharmaceutical composition comprises a carrier and the carrier is a parenteral carrier, oral carrier, or topical carrier.

In another aspect, the present invention provides composition of a compound according to formulae I-XVIId.

In one particular aspect, the present invention provides composition of matter and pharmaceutical composition of the compounds according to formula I, or IIa-XVIId, wherein $R^7$ is H.

In another particular aspect, the present invention provides composition of matter and pharmaceutical composition of the compounds according to formula I, or IIa-VIId, wherein $R^{3a}$ is OH and $R^{3b}$ is other than H.

In another particular aspect, the present invention provides composition of matter and pharmaceutical composition of the compounds according to formula Xa-Xb, XIa-XIb, XIIa-XVId, wherein $R^{3b}$ is other than H.

In another particular aspect, the present invention provides methods for preventing, treating or ameliorating a disease or condition using or providing the compounds of formula I-XVIId. The compounds of formula I-XVIId are also envisioned for use in preventing, treating or ameliorating an autoimmune disease or an inflammatory disease in a subject in need thereof. Also encompassed herein is the use of a compound of formula I-XVIId in the preparation of a medicament for preventing, treating or ameliorating an autoimmune disease or an inflammatory disease in a subject in need thereof. In a particular embodiment, the inflammatory disease manifests following allogeneic tissue transplantation and the inflammatory condition is GVHD or host immune response-mediated rejection of the transplant.

In an embodiment, this disclosure provides a method of preventing, treating or ameliorating an autoimmune or inflammatory disease or condition in a mammal comprising administering to the mammal or providing to the mammal an effective disease-treating or condition-treating amount of a compound that enhances the activity of Tregs and/or a compound that suppresses the activity of Th17 cells. Non-limiting examples of autoimmune disease or condition include type 1 diabetes or MS (and the animal model thereof, EAE), psoriasis, inflammatory bowel diseases, arthritis and uveitis, and non-limiting examples of other inflammatory conditions include GVHD. In an embodiment, the same compound may enhance the activity of Tregs and inhibit the activity of Th17 cells.

In an embodiment, this disclosure provides a method of preventing, treating or ameliorating an autoimmune or inflammatory disease or condition in a mammal comprising administering to the mammal a composition comprising, consisting essentially of, or consisting of an effective disease-treating or condition-treating amount of 3-oxoLCA and/or isoalloLCA. In an embodiment, this disclosure provides a method of preventing, treating or ameliorating an autoimmune or inflammatory disease or condition in a mammal comprising, consisting essentially of, or consisting of providing to the mammal an effective disease-treating or condition-treating amount of 3-oxoLCA and/or isoalloLCA.

In one embodiment, with respect to the method of treatment, the disease or condition is an autoimmune disease.

In one embodiment, with respect to the method of treatment, the disease or condition is an inflammatory disease.

In one embodiment, with respect to the method of treatment, the disease or condition is selected from type 1 diabetes, MS (and the animal model thereof, EAE), GVHD, inflammatory bowel disease, systemic lupus erythematosus, rheumatoid arthritis (and the animal model thereof, CIA), and auto-immune gastritis.

In one embodiment, with respect to the method of treatment, the disease or condition is selected from type 1 diabetes, MS (and the animal model thereof, EAE), and GVHD.

In another embodiment, with respect to the method of treatment, the disease or condition is selected from Crohn's disease, ulcerative colitis, sprue and food allergies.

In another particular aspect, the present invention provides methods for preventing, treating or ameliorating an autoimmune or inflammatory disease or condition in a mammal, which comprise administering or providing to the mammal an effective disease-treating or condition-treating amount of a compound according to formula I-XVIId.

In one embodiment, with respect to the method of treatment, the autoimmune disease or condition is type 1 diabetes or MS (and the animal model thereof, EAE), psoriasis, inflammatory bowel diseases, arthritis, and uveitis.

In one embodiment, with respect to the method of treatment, the inflammatory condition manifests following allogeneic tissue transplantation and the inflammatory condition is GVHD. In another embodiment thereof, the inflammatory condition that manifests following allogeneic tissue transplantation is host immune response-mediated rejection of the transplant. Accordingly, the compounds and compositions, and methods and uses thereof, as described herein may be implemented to promote Treg differentiation and/or Treg activity in subjects who have received transplants and thus, may subsequently present with or who are presenting with symptoms indicative of host immune response-mediated transplant rejection or GVHD.

Symptoms of acute GVHD include: a pruritic or painful rash; diarrhea, intestinal bleeding, cramping abdominal pain, ileus; and/or pruritus from initially asymptomatic liver involvement. Symptoms of chronic GVHD include: ocular burning, irritation, or photophobia; oral dryness; sensitivity to acidic or spicy foods; dysphagia; odynophagia; insidious weight loss; obstructive lung disease, with symptoms of wheezing, dyspnea, and chronic cough; and/or muscular weakness, neuropathic pain, and muscle cramps.

Host immune response-mediated transplant rejection may involve hyperacute, acute and/or chronic rejection of the transplant or graft. Chronic rejection of transplanted organs is the leading cause of organ transplant failure. Symptoms of transplant rejection are known to those skilled in the art and depend on the type of organ or tissue transplanted. Generally, such symptoms include a decrease in organ function; general discomfort or lack of ease; flu-like symptoms such as chills, body aches, nausea, cough and/or shortness of breath; pain or swelling in the area of the transplant; and/or fever. Tissue biopsy of the transplant may also be performed to determine if infiltrating T cells are present and, if so, at what ratio with respect to esoinophils, plasma cells and neutrophils also present in the transplant; to evaluate the structural integrity of the transplant tissue; and to assess damage to vascularization therein. Non-invasive methods such as those involving cellular magnetic resonance imaging (MRI) to visualize immune cells radiolabeled in vivo may also offer options for assessing the status of a transplant and may inform an attending physician as to whether a transplant recipient would benefit from the compounds, compositions, and/or methods described herein.

In another particular aspect, the present invention provides methods for increasing the number of Treg cells in a mammal comprising administering to the mammal a compound according to formula I-XVIId or a composition thereof.

In another particular aspect, the present invention provides methods for promoting differentiation and proliferation of T regulatory (Treg) lymphocytes in vitro, the method comprising the steps of: isolating a population of naive CD4+ T cells from a subject; and incubating the population of naive CD4+ T cells in serum-free culture medium comprising a T cell receptor stimulus, IL-2, TGF-β, and the compound according to formula I, wherein the incubating promotes differentiation of Treg lymphocytes and/or suppress Th17 cell function.

In one embodiment, the T cell receptor stimulus comprises anti-CD3 antibodies and/or anti-CD28 antibodies.

In another embodiment, the anti-CD3 antibodies are at a concentration of 0.25 µg/ml and the anti-CD28 antibodies are at a concentration of 1 ng/ml.

In another embodiment, the IL-2 is at a concentration of 100 U/mL.

In another embodiment, the TGF-β is at a concentration between 0-1 ng/ml.

In another embodiment, the TGF-β is at a concentration between 0-0.1 ng/ml.

In another embodiment, the TGF-β is at a concentration of between 0.01-0.1 ng/ml.

In another embodiment, the TGF-β is at a concentration of 0.01 or 0.1 ng/ml.

In another embodiment, the population of CD4+ T cells is isolated based on positive cell surface staining for cell surface antigens or receptors.

In another embodiment, the population of naive CD4+ cells is CD62Lhigh, CD44low-int, and CD25−. The naive cell marker for human T cells are CD45RA+ and CD45RO−.

In another embodiment, the incubating lasts for a duration of three or four days.

In another embodiment, the cell surface marker or cell surface antigen expressed on Treg lymphocytes is CD4+, CD25+, or CD127−.

In another embodiment, Treg differentiation is assayed by fluorescence activated cell sorting to determine FoxP3 expression in cells following the incubating.

In another embodiment, the method further comprises administering the Treg lymphocytes to a subject in need thereof.

In particular aspect, the present invention provides methods for preventing, treating or ameliorating an autoimmune disorder. In one embodiment, the autoimmune disorder is MS (and the animal model thereof, EAE). In another embodiment, the disorder is rheumatoid arthritis (and the animal model thereof, CIA). In a further embodiment, the disorder is type I diabetes or an animal model thereof. In yet another embodiment, the disorder is psoriasis, inflammatory bowel disease (IBD), Crohn's disease, ulcerative colitis, eczema, systemic lupus erythematosus, auto-immune gastritis, or thyroiditis.

In another particular aspect, the present invention provides methods for preventing or ameliorating an inflammatory condition that manifests following allogeneic tissue transplantation of an organ, tissue, or cell into a mammal, wherein the method comprises administering or providing to the mammal a compound according to formula I-XVIId or a composition thereof prior to transplanting the organ, tissue, or cell. Administration of the compound according to formula I-XVIId or a composition thereof prior to transplantation promotes differentiation of Treg cells and/or suppress Th17 cell function and/or activity thereof in the mammal (i.e., the intended transplant recipient) in advance of the transplantation and thus, establishes an immune response in the mammal that favors Treg activity.

In yet another aspect, the present invention provides methods for treating an inflammatory condition that manifests following allogeneic tissue transplantation of an organ, tissue, or cell into a mammal, wherein the method comprises administering to the mammal a compound according to formula I-XVIId or a composition thereof concurrent with or after transplanting the organ, tissue, or cell. Administration of the compound according to formula I-XVIId or a composition thereof concurrent with or after transplantation promotes differentiation of Treg cells and/or suppress Th17 cell function and/or activity thereof in the mammal (i.e., the transplant recipient) in the presence of the transplant and thus, establishes an immune response in the mammal that favors Treg activity.

In another particular aspect, the present invention provides methods for preventing or ameliorating an inflammatory condition that manifests following allogeneic tissue transplantation of an organ, tissue, or cell into a mammal, wherein the method comprises administering to the mammal a Treg population generated in accordance with methods presented herein or a composition thereof prior to transplanting the organ, tissue, or cell. Administration of the Treg population or a composition thereof prior to transplantation establishes an immune response that favors Treg activity in the mammal (i.e., the intended transplant recipient) in advance of the transplantation and thus, establishes an in vivo environment that promotes transplant retention.

In yet another aspect, the present invention provides methods for treating an inflammatory condition that manifests following allogeneic tissue transplantation of an organ, tissue, or cell into a mammal, wherein the method comprises administering to the mammal a Treg population generated in accordance with methods presented herein or a composition thereof concurrent with or after transplanting the organ, tissue, or cell. Administration of the Treg population or a composition thereof concurrent with or after transplantation establishes an immune response that favors Treg activity in the mammal (i.e., the transplant recipient) in the presence of the transplant and thus, establishes an in vivo environment that promotes transplant retention.

In one embodiment, the transplant is an organ or tissue derived from one of the following: heart, kidney, liver, lung, pancreas, bone marrow, cartilage, cornea, or neuronal tissue. It is understood that such transplants may comprise cells derived from the aforementioned organs or tissue. Inflammatory conditions that manifest following allogeneic tissue transplantation include GVHD and host immune response-mediated rejection of the transplant. Irrespective of the inflammatory condition to be prevented or treated in accordance with methods presented herein, promoting differentiation of Treg cells or Treg activity and/or suppress Th17 cell function or increasing the number of Tregs establishes a balance in the immune response of the mammal that favors preservation of the transplant and the health of the mammal.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds described herein have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

In an aspect, this disclosure provides a pharmaceutical composition comprising the compounds of according to formula I-XVIId, which may be the only bile acids present in the composition. In an embodiment, this disclosure provides a pharmaceutical composition consisting essentially of, or consisting of compounds according to formula I-XVIId.

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pennsylvania, which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Regulatory T Cell Assays and Methods of Treatment

The suppressive activity of regulatory T cells (Tregs) can be evaluated using in vitro and/or in vivo Treg assays.

In Vitro Assays

Natural Tregs cells can be isolated from mice and humans based on their expression of CD25. The first in vitro assays to measure Treg function were developed based on the finding that CD4+CD25+ T cells can potently suppress the proliferation of activated CD4+CD25− and CD8+ T cells when the populations were cocultured in vitro. See, for example, Takahashi et al. (Int Immunol 1998; 10:1969-1980) and Thornton et al. (J Exp Med 1998; 188:287-296), the entire content of each of which is incorporated herein by reference. Since that time, researchers have routinely used in vitro suppression assays to determine the suppressive capacity of Tregs. These assays benefit from the relative ease with which they can be set up, the limited number of reagents required, and their reliability. The versatility of such assays is expanded by the fact that conventional T cells (Tconv) and Tregs can be purified from genetically deficient mice, thereby facilitating investigations into the role/s that individual molecules play in suppression. Ex vivo suppressive capacity of Tregs obtained from normal or diseased subjects can, moreover, provide information regarding immunocompetence. Numerous variables, including type of activation, cell number, and degree of proliferation can be manipulated readily, even within a single experiment.

In vitro suppression assays can be performed with either antigen-specific Tregs, which are generally purified following immunologic response to a specific pathogen or disease state, or polyclonal Tregs, which are typically assayed for their ability to suppress Tconv cell proliferation. Variants of the standard in vitro Treg suppression assay have been developed that demonstrate the importance of soluble factors in Treg-mediated suppression. See, for example, Collison et al. (J Immunol 2009; 182:6121-6128), the entire content of which is incorporated herein by reference. A review of in vitro Treg suppression assays and protocols therefor are presented in Collison et al. (Methods Mol Biol 707:21-37, 2011; the entire content of which is incorporated herein by reference).

In Vivo Assays

A number of in vivo models have been developed to assess Treg function/activity. Workman et al. (Methods Mol Biol 707:119-156, 2011; the entire content of which is incorporated herein by reference), for example, describe five different in vivo models that assess Treg function: (1) a homeostasis model, (2) an inflammatory bowel disease (IBD) recovery model, (3) an experimental autoimmune encephalomyelitis (EAE) model, (4) a B16 melanoma model, and (5) a Foxp3-rescue model. As noted by Workman et al., these models are effective at elucidating Treg function but require minimal numbers of Tregs (only between 0.5 and $1\times10^6$ per Tregs per mouse).

Additional in vivo models have been used to assess Treg activity/function and are described in, for example, Belkaid et al. (Nature Reviews 7:875-888, 2007); Tang et al. (Nature Immunology 9:239-244, 2008); and Bettini et al. (Current Opinion in Immunology 21:612-618, 2009); the entire content of each of which is incorporated herein by reference.

As a further aspect, the present compounds are envisioned for use as a pharmaceutical especially in the treatment or prevention of the aforementioned conditions and diseases.

Also provided herein is the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as, e.g., arthritis, diabetes, multiple sclerosis (and the animal model thereof, experimental autoimmune encephalomyelitis (EAE)), rheumatoid arthritis (and the animal model thereof, collagen-induced arthritis (CIA)), psoriasis, or asthma, the regimen for treatment usually stretches over many months or years, so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses. Modes of administration suitable for mucosal sites are also envisioned herein and include without limitation: intra-anal swabs, enemas, intranasal sprays, and aerosolized or vaporized compounds and/or compositions for delivery to the lung mucosa. One of skill in the art would choose an appropriate delivery mode/s based on a variety of parameters, including the organ or tissue site in a patient with a disease or condition that is most severely affected by the disease or condition. A skilled practitioner could, for example, treat a patient afflicted with an inflammatory bowel disease (IBD) with a therapeutic regimen that included delivery of the compounds or compositions of the invention using an enema for direct delivery to the bowel.

When used to prevent the onset of an inflammatory condition or autoimmune disorder, the compounds of this invention will be administered to a patient at risk for developing the condition or disorder, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity and are determined to safe and efficacious for such combined administration.

General Synthetic Procedures

The steroid compounds of this invention may be purchased from various commercial sources or can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds of the invention may be prepared from known or commercially available starting materials and reagents by one skilled in the art of organic synthesis.

General Materials and Methods:

All commercially available reagents and solvents were purchased and used without further purification. All microwave reactions were carried out in a sealed microwave vial equipped with a magnetic stir bar and heated in a Biotage Initiator Microwave Synthesizer. HPLC purification was performed using a Waters semi-preparative HPLC equipped with a Phenomenex Luna© C18 reverse phase (5 micron, 30×75 mm) column (unless state otherwise) having a flow rate of 45 mL/min. The mobile phase was a mixture of acetonitrile and $H_2O$ each containing 0.1% trifluoroacetic acid. $^1H$ spectra were recorded using either an Inova 400 MHz spectrometer (Varian) or an Inova 300 MHz spectrometer (Varian). Two LCMS methods were used to analyze samples' purity. Method 1: Agilent 1200 series LC/MS equipped with a Zorbax™ Eclipse XDB-C18 reverse phase (5 micron, 4.6×150 mm) column having a flow rate of 1.1 mL/min. The mobile phase was a mixture of acetonitrile and $H_2O$ each containing 0.05% trifluoroacetic acid. A gradient of 5% to 100% acetonitrile over 8 minutes was used during analytical analysis. Method 2: Acquity HPLC equipped with a Waters BEH C18, 1.7 micron, 2.1×50 mm column; Column Temperature: 45 degrees C.; Flow: 0.5 mL/min; Solvent A: 0.05% TFA in Water; Solvent B: 0.025% TFA in Acetonitrile; Gradient: 2% to 100% Solvent B over 1.3 minutes; Run Time-3 min. High-resolution mass spectroscopy measurements were performed on a Agilent 6210 Electrospray TOF mass spectrometer.

The following general procedures were used to synthesize compounds having different but analogous structures. One skilled in the art of synthesis will recognize how to modify these general procedures if necessary to accomplish the desired transformations.

Representative Synthetic Methods

Chemical Synthesis of 3-oxoLCA and Iso-alloLCA

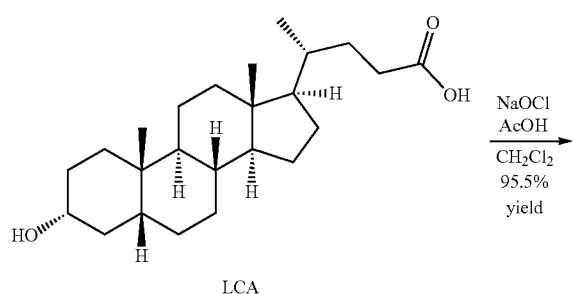

LCA

NaOCl
AcOH
$CH_2Cl_2$
95.5%
yield

-continued

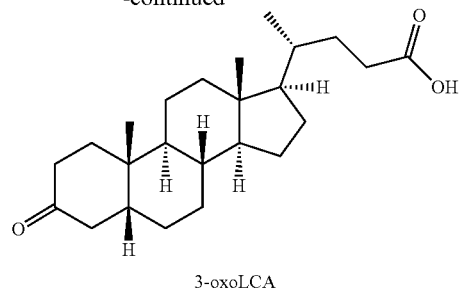

3-oxoLCA 3-oxoLCA was prepared on a large scale by the oxidation of LCA according to the following procedure. Glacial AcOH (160 mL) and $CH_2Cl_2$ (160 mL; total concentration 0.2 M) were added to a 1 L round-bottom flask charged with a stir bar and LCA (24.08 g, 63.95 mmol, 1.0 equivalent). The suspension was stirred until complete dissolution and then immersed in a room temperature water bath. An addition funnel was affixed to the flask and charged with NaOCl (77.6 mL, 95.95 mmol, 1.5 equivalents; 8.25 wt % Chlorox© solution). The bleach solution was added dropwise over a period of ~30 minutes with vigorous stirring. A slight yellowing of the reaction occurred; too rapid of an addition leads to a bright yellow solution and should be avoided. Upon consumption by TLC analysis (~16 h; 19:1 $CH_2Cl_2$/ethyl acetate+2% AcOH; p-Anisaldehyde stain), the excess oxidant was quenched by the addition of i-PrOH (24.5 mL, 320 mmol, 5 equivalents). After an additional hour, the reaction was concentrated in vacuo to a slurry. The white slurry was partially dissolved in $CH_2Cl_2$ (400 mL), transferred to a separatory funnel containing a 5% aqueous solution of $NaHSO_3$ (150 mL) and acidified to pH<3 with 1 M HCl. The layers were vigorously mixed, separated, and the aqueous layer was extracted with $CH_2Cl_2$ (3×25 mL). The combined organic layers were washed with saturated aqueous NaCl (50 mL), dried over $Na_2SO_4$ for >30 minutes, filtered and concentrated in vacuo. The resulting colorless to pale yellow oil forms a white solid over time as the AcOH is removed. The crude $^1H$ NMR ($CDCl_3$) shows only the desired product with AcOH; however, storage over about a day leads to a noticeable yellowing of the material that increases over time (presumably due to residual oxidant). The crude solid is purified by trituration with $Et_2O$/hexanes. To break up any large chunks, $Et_2O$ (100 mL) and a stir bar are added to the crude solid and stirred. Hexane (100 mL) is then added while stirring, and then the contents were placed in an ice bath and mixing ceased. Vacuum filtration with washing and vacuum drying afforded 3-oxoLCA as a white, crystalline solid (19.488 g, 52.028 mmol, 81.4% yield). The filtrate was concentrated and triturated in a similar manner (30 mL total of 1:1 $Et_2O$/hexanes) to generate an additional portion of white crystalline solid (3.3836 g, 9.033 mmol, 14.1% yield). The combined mass of 3-oxoLCA was 22.872 g (61.061 mmol, 95.5% yield). Characterization data: $R_f$=0.31 (19:1 hexanes/ethyl acetate+2% AcOH; p-Anisaldehyde); mp 138-141° C.; $^1H$ NMR (600 MHz, $CDCl_3$): δ 2.69 (app t, J=14.3 Hz, 1H), 2.40 (ddd, J=15.6, 10.3, 5.2 Hz, 1H), 2.33 (td, J=14.7, 5.3 Hz, 1H), 2.26 (ddd, J=15.8, 9.6, 6.4 Hz, 1H), 2.17 (app d, J=14.2 Hz, 1H), 2.03 (dt, J=8.8, 4.5 Hz, 3H), 1.88 (ddt, J=13.6, 9.2, 4.6 Hz, 2H), 1.83-1.80 (m, 2H), 1.62-1.59 (m, 1H), 1.52-1.06 (m, 15H), 1.02 (s, 3H), 0.94 (d, J=6.5 Hz, 3H), 0.69 (s, 3H); $^{13}C\{^1H\}$ NMR (151 MHz, $CDCl_3$): δ 213.7, 179.8, 56.6, 56.1, 44.5, 42.9, 42.5, 40.9, 40.2, 37.4, 37.2, 35.7, 35.5, 35.0, 31.1, 30.9, 28.3, 26.8, 25.9, 24.3, 22.8, 21.4, 18.4, 12.2; IR (ATR): 2925, 2878, 2858, 1698, 1376, 1307, 1264, 945, 735 cm$^{-1}$; HRMS (DART−) m/z: [M−H]$^-$ calculated for $C_{24}H_{37}O_3$ 373.27427, found 373.27524; $[\alpha]_D^{21.5}$+31.5 (c 1.205, $CH_2Cl_2$). NMR spectral images for 3-oxoLCA are shown in FIGS. 14 and 15.

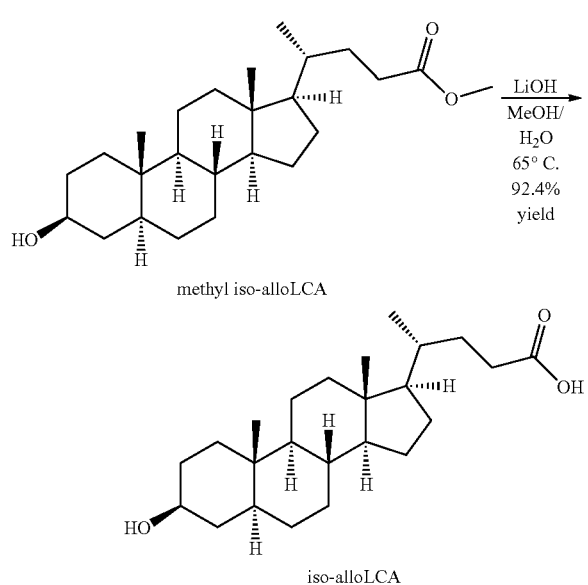

methyl iso-alloLCA iso-alloLCA

IsoalloLCA was prepared on a large scale by the saponification of methyl isoalloLCA according to the following procedure. Methanol (271 mL) was added to a 1 L round-bottom flask charged with a stir bar and methyl iso-alloLCA (6.616 g, 18.894 mmol, 1.0 equivalent). A reflux condenser was affixed to the flask, and the contents were placed under argon and warmed to 65° C. to yield a clear solution. To this solution, a mixture of MeOH:$H_2O$ (67 mL; 5:1 MeOH:$H_2O$, 0.05 M) was added followed by LiOH (2.023 g, 84.47 mmol, 5.0 equivalents) at 65° C. Upon completion by TLC analysis (2:1 hexanes/ethyl acetate; p-Anisaldehyde), the reaction was cooled to room temperature and concentrated in vacuo to a white slurry. $H_2O$ (200 mL) was added to this slurry, followed by acidification to pH<3 with 1 M HCl. The congealed mass was sonicated at >50° C. for at least 3 h to yield a free-flowing, fluffy white solid. The contents were cooled to room temperature, then in an ice bath and isolated via vacuum filtration. Washing and further drying of the filter cake (high vacuum) yielded isoalloLCA as a powdery white solid (5.8797 g, 15.613 mmol, 92.4% yield). Characterization data: $R_f$=0.23 (1:1 hexanes/ethyl acetate; p-Anisaldehyde); mp 206-210° C.; $^1$H NMR (600 MHz, DMSO-d6): δ 11.96 (br s, 1H), 4.40 (br s, 1H), 2.22 (ddd, J=15.3, 9.7, 5.4 Hz, 1H), 2.11-2.06 (m, 1H), 1.91 (app d, J=12.3 Hz, 1H), 1.81-1.74 (m, 1H), 1.68-0.80 (m, 24H), 0.86 (d, J=6.6 Hz, 3H), 0.74 (s, 3H), 0.61 (s, 3H), 0.61-0.57 (m, 1H); $^{13}$C{$^1$H} NMR (151 MHz, DMSO-d6): δ 174.8, 69.3, 56.0, 55.5, 53.8, 44.4, 42.2, 38.2, 36.6, 35.07, 35.04, 34.8, 31.7, 31.3, 30.77, 30.68, 28.4, 27.6, 23.8, 20.8, 18.1, 12.1, 11.9; IR (ATR): 3381, 2922, 2869, 2853, 1700, 1443, 1269, 1191, 1030, 905, 611 cm$^{-1}$; HRMS (DART−) m/z: [M− H]$^-$ calculated for $C_{24}H_{39}O_3$ 375.28992, found 375.29077; $[\alpha]_D^{22.5}$+28.04 (c 0.573, $CH_3OH$). NMR spectral images for isoalloLCA are shown in FIGS. 16 and 17.

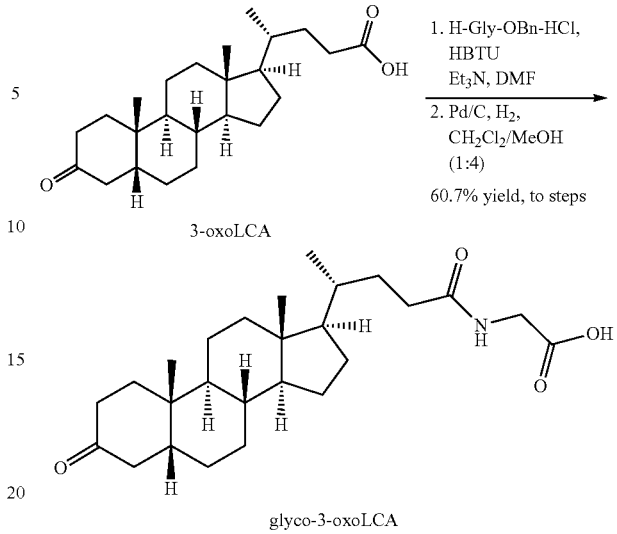

3-oxoLCA glyco-3-oxoLCA

Synthesis of Glyco-3-oxoLCA. The glycine conjugate of 3-oxoLCA was prepared by amidation with a glycine ester, followed by ester cleavage. Dimethylformamide (DMF, 2.0 mL, 0.2 M) was added to a flame-dried 25 mL Schlenk flask charged with a stir bar, 3-oxoLCA (150.0 mg, 0.4004 mmol, 1.0 equivalent), and glycine benzyl ester-HCl (89.9 mg, 0.446 mmol, 1.1 equivalent) under argon to produce a slightly cloudy suspension. $Et_3N$ (167 µL, 1.20 mmol, 3.0 equivalent) and hexafluorophosphate benzotriazole tetramethyl uranium (HBTU, 154.9 mg, 0.4824 mmol, 1.2 equivalent) were added to this solution while stirring at room temperature. Upon completion by TLC analysis (1:1 hexanes/EtOAc; p-Anisaldehyde; ca. 24 h), the reaction was transferred to a 125 mL separatory funnel with EtOAc (25 mL) and $H_2O$ (15 mL). The funnel was mixed and the layers were separated. The organic layer was washed with 1 M HCl (10 mL), the aqueous layers were combined and further extracted with EtOAc (10 mL). The combined organic extracts were washed with brine (5 mL), dried over $MgSO_4$, filtered, and concentrated in vacuo to a pale yellow oil. This crude oil was purified by Biotage automated flash chromatography on $SiO_2$ (20 g, 13® 50% EtOAc in hexanes) to afford the desired amide product as a colorless foam (184.4 mg, 0.3534 mmol, 88.3% yield). $R_f$=0.28 (1:1 hexanes/EtOAc; p-Anisaldehyde); $^1$H NMR (600 MHz, CDCl$_3$): δ 7.39-7.33 (m, 5H), 5.96 (br s, 1H), 5.19 (s, 2H), 4.09 (d, J=5.1 Hz, 2H), 2.69 (app t, J=14.3 Hz, 1H), 2.32 (dtd, J=20.7, 11.1, 5.0 Hz, 2H), 2.14 (ddd, J=15.1, 9.9, 5.7 Hz, 2H), 2.05-2.00 (m, 3H), 1.91-1.80 (m, 4H), 1.60 (td, J=8.6, 4.6 Hz, 1H), 1.52-1.18 (m, 11H), 1.14-1.06 (m, 4H), 1.02 (s, 3H), 0.93 (d, J=6.5 Hz, 3H), 0.68 (s, 3H); $^{13}$C{$^1$H} NMR (151 MHz, CDCl$_3$): δ 213.5, 173.7, 170.2, 135.3, 128.8, 128.7, 128.5, 67.3, 56.6, 56.2, 44.5, 42.9, 42.5, 41.5, 40.9, 40.2, 37.4, 37.2, 35.7, 35.6, 35.0, 33.4, 31.7, 28.3, 26.8, 25.9, 24.3, 22.8, 21.3, 18.5, 12.2; IR (ATR): 3317, 2935, 2865, 1750, 1711, 1654, 1540, 1455, 1187, 733 cm−1; HRMS (DART+) m/z: [M+NH$_4$]$^+$ calculated for $C_{33}H_{51}O_4N_2$ 539.3843, found 539.3848; $[\alpha]_D^{23.9}$+23.6 (c 0.75, $CH_2Cl_2$). $CH_2Cl_2$ (0.70 mL) and methanol (2.8 mL; 1:4, 0.1 M) were added to benzyl glyco-3-oxoLCA (184.4 mg, 0.3534 mmol, 1.0 equivalent) in a 1 dram vial containing a stir bar, followed by Pd/C (74.6 mg, 5 wt % on carbon, 0.0350 mmol, 0.10 equivalent). The vial was equipped with a septum and affixed to a H2-filled balloon. The vial headspace was purged with H2 for ca. 2 min, and then mixed vigorously under H2. Upon completion by TLC analysis (1:2 hexanes/ethyl acetate; p-Anisaldehyde; ca. 17 h), the reaction was filtered through a 0.45 m polytetrafluoroethylene (PTFE) syringe filter with 9:1 CH$_2$Cl$_2$:methanol and concentrated in vacuo. H$_2$O (20 mL) was added to the flask, and the white solid was sonicated, followed by acidification to pH<3 with 1 M HCl. The precipitate was cooled in an ice bath and isolated via vacuum filtration. Washing and further drying (high vacuum) of the pellet afforded a mixture containing glyco-3-oxoLCA. Purification by flash chromatography on SiO$_2$ (2.5×22 cm, 19:1 CH$_2$Cl$_2$:MeOH+1% AcOH) afforded a clear film that solidifies over time. To this dried film was added acidic H$_2$O (15 mL, pH<3), the contents were sonicated to disperse the solid, and then cooled and isolated via vacuum filtration. Pellet drying under high vacuum yielded glyco-3-oxoLCA (104.7 mg, 0.2426 mmol, 60.7% yield) as a white solid. Characterization data: R$_f$=0.10 (19:1 CH$_2$Cl$_2$:MeOH+1% AcOH; p-Anisaldehyde); mp 172-176° C.; $^1$H NMR (600 MHz, DMSO-d6): δ 12.42 (br s, 1H), 8.09 (t, J=5.8 Hz, 1H), 3.71 (d, J=5.4 Hz, 2H), 2.74 (app t, J=14.2 Hz, 1H), 2.36 (td, J=14.6, 5.4 Hz, 1H), 2.14 (ddd, J=14.2, 9.7, 4.8 Hz, 1H), 2.03 (ddd, J=14.6, 9.0, 6.3 Hz, 1H), 1.96-1.94 (m, 3H), 1.84-1.78 (m, 3H), 1.74-1.64 (m, 2H), 1.56 (qd, J=11.8, 3.5 Hz, 2H), 1.43-1.02 (m, 14H), 0.96 (s, 3H), 0.89 (d, J=6.5 Hz, 3H), 0.65 (s, 3H); $^{13}$C{$^1$H} NMR (151 MHz, DMSO-d6): δ 211.8, 172.9, 171.4, 55.69, 55.63, 43.6, 42.3, 41.9, 40.5, 36.7, 36.5, 35.1, 34.9, 34.4, 32.0, 31.4, 27.7, 26.2, 25.3, 23.8, 22.2, 20.8, 18.3, 11.9; IR (ATR): 2927, 2862, 1717, 1576, 1432, 1233 cm$^{-1}$; HRMS (DART+) m/z: [M+H]$^+$ calculated for C$_{26}$H$_{42}$O$_4$N 432.3108, found 432.3109; [α]$_D^{23.6}$+32.0 (c 0.575, CH$_3$OH). NMR spectra are shown in FIGS. 18 and 19.

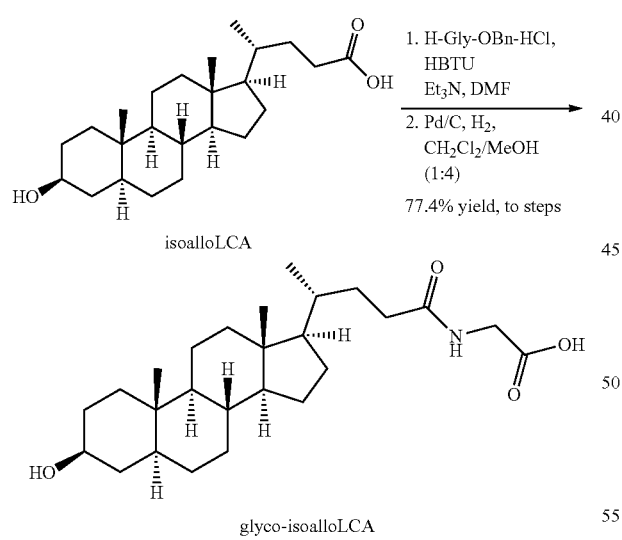

isoalloLCA

1. H-Gly-OBn-HCl, HBTU, Et$_3$N, DMF
2. Pd/C, H$_2$, CH$_2$Cl$_2$/MeOH (1:4)

77.4% yield, to steps glyco-isoalloLCA

Glyco-isoalloLCA. Glyco-isoalloLCA was prepared using the same amidation and ester cleavage procedure used for glyco-3-oxoLCA. Amide coupling of isoalloLCA (71.8 mg, 0.1907 mmol, 1.0 equivalent) with glycine benzyl ester-HCl, followed by automated flash purification on SiO$_2$ (20 g, 16® 80% EtOAc in hexanes) afforded benzyl glyco-isoalloLCA (90.6 mg, 0.1730 mmol, 90.7% yield) as a colorless foam. R$_f$=0.28 (1:1 hexanes/EtOAc; p-Anisaldehyde); $^1$H NMR (600 MHz, CDCl$_3$): δ 7.39-7.33 (m, 5H), 5.90 (br s, 1H), 5.19 (s, 2H), 4.09 (d, J=5.1 Hz, 2H), 3.59 (tt, J=10.6, 5.2 Hz, 1H), 2.29 (ddd, J=14.8, 10.5, 4.7 Hz, 1H), 2.13 (ddd, J=15.0, 9.9, 5.6 Hz, 1H), 1.95-1.93 (m, 1H), 1.86-1.79 (m, 3H), 1.71-1.64 (m, 2H), 1.59-1.54 (m, 2H), 1.50-1.21 (m, 11H), 1.13-0.94 (m, 6H), 0.92 (d, J=6.5 Hz, 3H), 0.86 (dd, J=12.0, 5.6 Hz, 1H), 0.80 (s, 3H), 0.65 (s, 3H), 0.62-0.60 (m, 1H); $^{13}$C{$^1$H} NMR (151 MHz, CDCl$_3$): δ 173.8, 170.2, 135.3, 128.8, 128.7, 128.5, 71.5, 67.4, 56.6, 56.1, 54.5, 45.0, 42.8, 41.5, 40.2, 38.4, 37.2, 35.66, 35.64, 35.62, 33.4, 32.2, 31.74, 31.70, 28.9, 28.3, 24.3, 21.4, 18.5, 12.5, 12.3; IR (ATR): 3301, 2927, 2862, 1751, 1653, 1540, 1188, 1040, 733 cm-1; HRMS (DART+) m/z: [M+H]$^+$ calculated for C$_{33}$H$_{50}$O$_4$N 524.3734, found 524.3739; [α]$_D^{22.4}$+16.9 (c 0.65, CH$_2$Cl$_2$). Hydrogenolysis of benzyl glyco-isoalloLCA (50.7 mg, 0.0968 mmol, 1.0 equivalent) with Pd/C and H$_2$ according to glyco-3-oxoLCA, followed by filtration, concentration, and precipitation with acidic H$_2$O (pH<3) afforded glyco-isoalloLCA (35.8 mg, 0.0826 mmol, 77.4% yield) as a white powdery solid. Characterization data: R$_f$=0.04 (1:2 hexanes:EtOAc; p-Anisaldehyde); mp 225-230° C.; $^1$H NMR (600 MHz, CD$_3$OD): δ 3.88 (s, 2H), 3.50 (tt, J=10.7, 5.1 Hz, 1H), 2.29 (ddd, J=14.3, 9.9, 4.8 Hz, 1H), 2.16 (ddd, J=14.1, 9.8, 6.6 Hz, 1H), 2.01-1.98 (m, 1H), 1.91-1.85 (m, 1H), 1.83-1.67 (m, 4H), 1.62-1.57 (m, 1H), 1.54-1.26 (m, 11H), 1.17-0.88 (m, 8H), 0.96 (d, J=6.6 Hz, 3H), 0.83 (s, 3H), 0.69 (s, 3H), 0.68-0.63 (m, 1H); $^{13}$C{$^1$H} NMR (151 MHz, CD$_3$OD): δ 177.1, 173.1, 71.9, 57.9, 57.5, 55.9, 46.2, 43.8, 41.7, 41.4, 38.9, 38.3, 36.91, 36.78, 36.61, 33.8, 33.3, 33.1, 32.1, 30.0, 29.2, 25.2, 22.4, 18.9, 12.8, 12.5; IR (ATR): 3314, 2925, 2851, 1742, 1625, 1220, 1046, 1031, 841 cm$^{-1}$; HRMS (DART+) m/z: [M+H]+ calculated for C$_{26}$H$_{44}$O$_4$N 434.3265, found 4345.3267; [α]$_D^{23.8}$+22.4 (c 0.41, CH$_3$OH). NMR spectra are shown in FIGS. 20 and 21.

Representative Compounds of the Invention

The following steroid compounds are purchased and tested for their Treg activity.

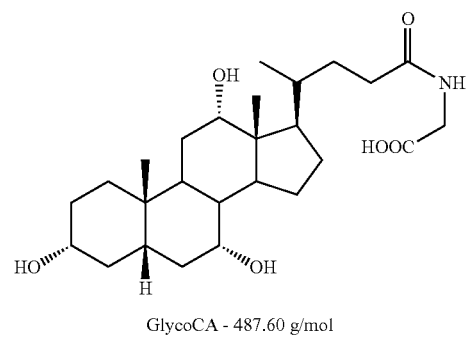

GlycoCA - 487.60 g/mol

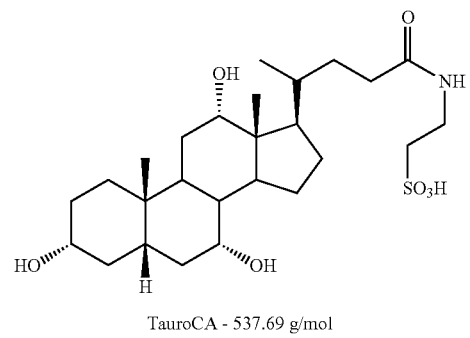

TauroCA - 537.69 g/mol

-continued
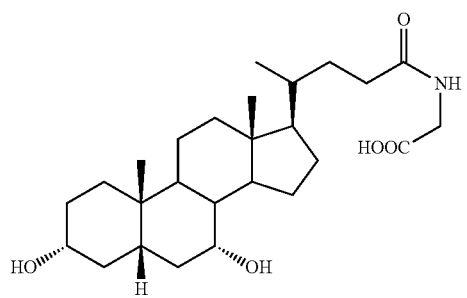
GlycoCDCA - 471.61 g/mol
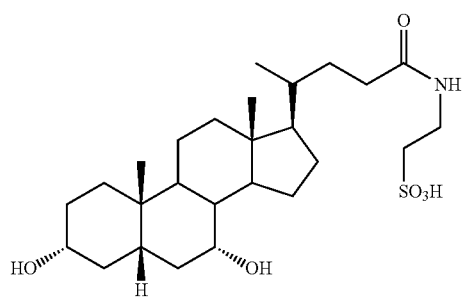
TauroCDCA - 521.69 g/mol
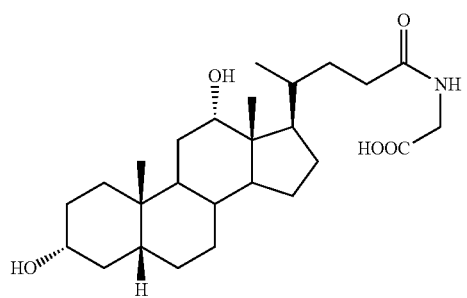
GlycoDCA - 471.61 g/mol
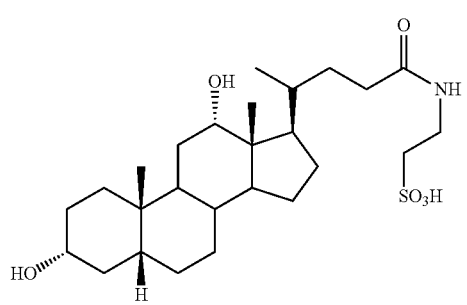
TauroDCA - 521.69 g/mol
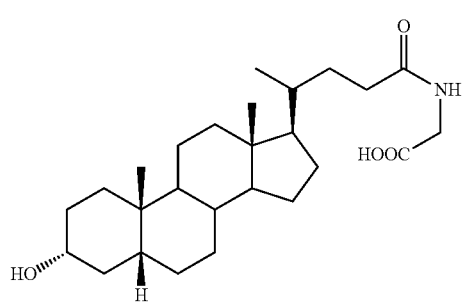
GlycoLCA - 455.60 g/mol
-continued
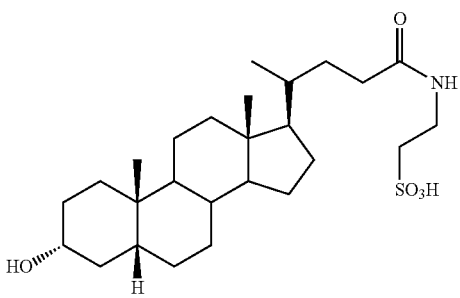
TauroLCA - 505.69 g/mol
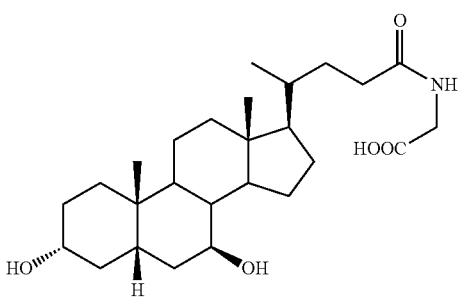
GlycoUDCA - 449.62 g/mol
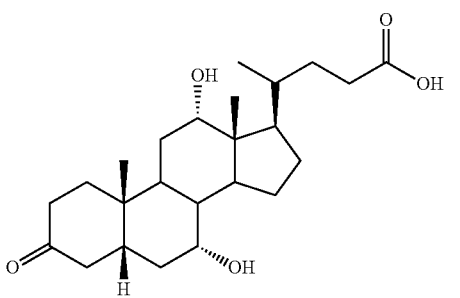
3-oxoCA - 406.56 g/mol
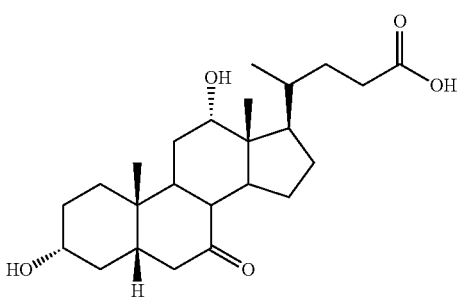
7-oxoCA - 406.56 g/mol
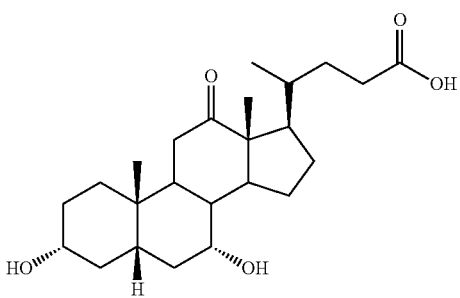
12-oxoCA - 406.56 g/mol

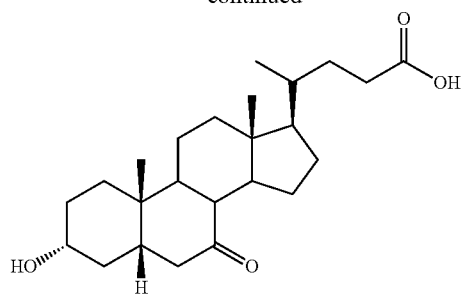
7-oxoCDCA - 390.56 g/mol
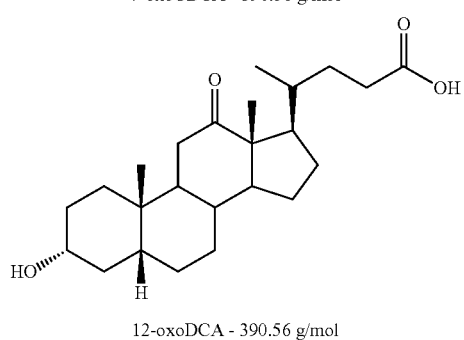
12-oxoDCA - 390.56 g/mol
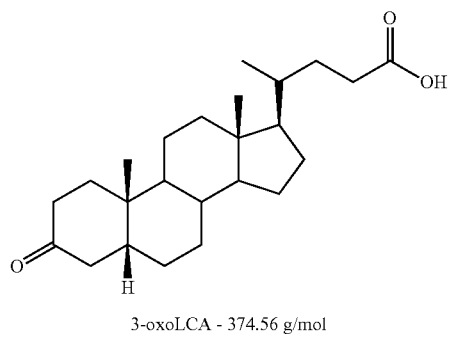
3-oxoLCA - 374.56 g/mol
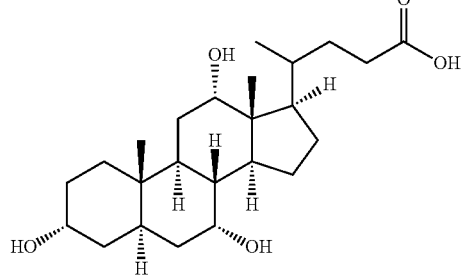
Allocholic acid
(AlloCA) 408.57 g/mol
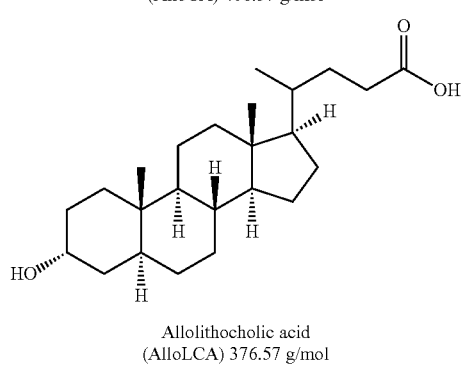
Allolithocholic acid
(AlloLCA) 376.57 g/mol
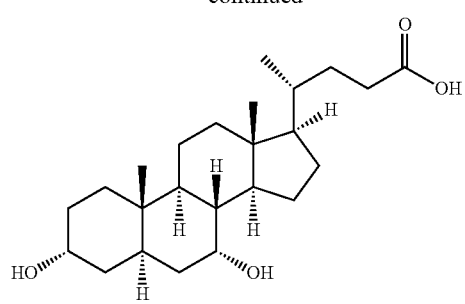
AlloCDCA
MW = 392.57 g/mol
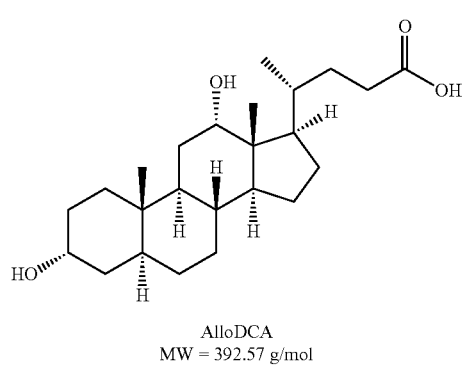
AlloDCA
MW = 392.57 g/mol
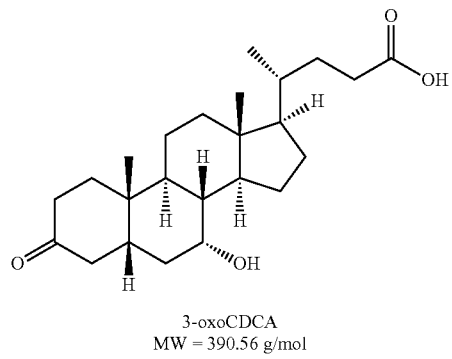
3-oxoCDCA
MW = 390.56 g/mol
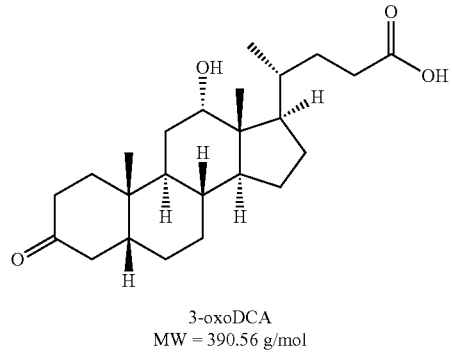
3-oxoDCA
MW = 390.56 g/mol -continued

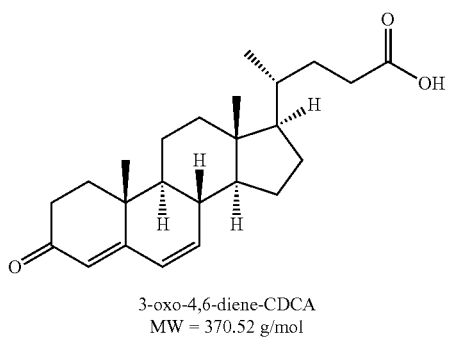

3-oxo-4,6-diene-CDCA
MW = 370.52 g/mol

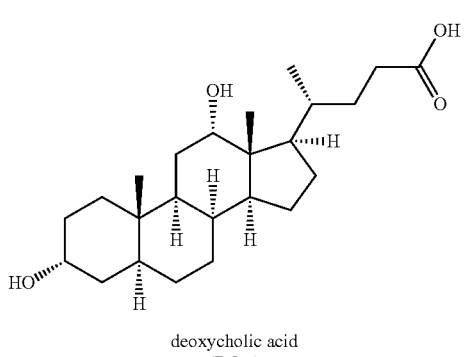

deoxycholic acid
(DCA)

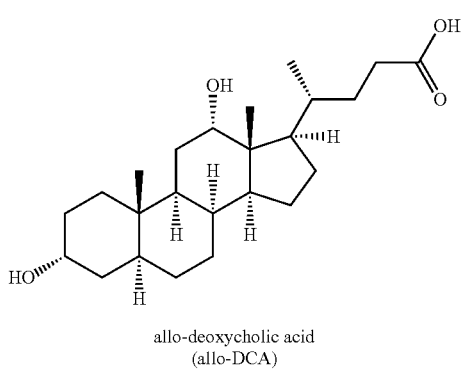

allo-deoxycholic acid
(allo-DCA)

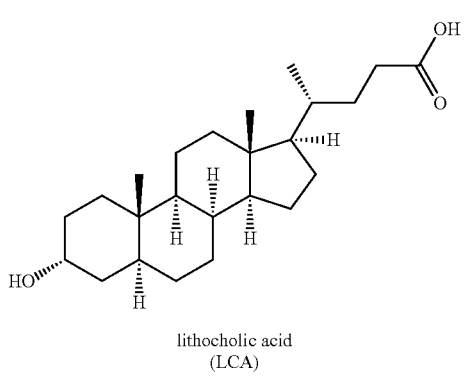

lithocholic acid
(LCA)

-continued

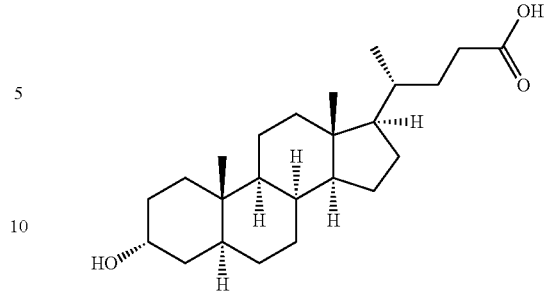

allo-lithocholic acid
(allo-LCA)

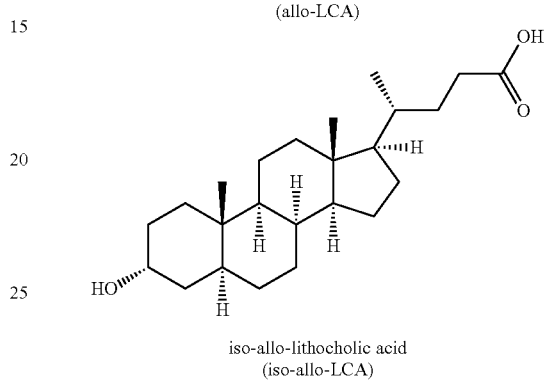

iso-allo-lithocholic acid
(iso-allo-LCA)

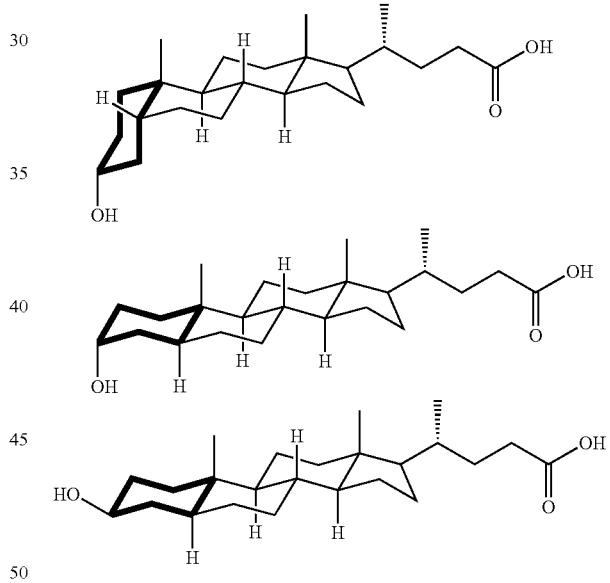

With aspects of the claimed invention now being generally described, these will be more readily understood by reference to the following examples, which are included merely for purposes of illustration of certain features and embodiments of the presently claimed invention and are not intended to be limiting.

Example 1

This example provides a description of methods and compounds of the present disclosure.

Bile acids are abundant in the mammalian gut where they undergo bacteria-mediated transformation, generating a large pool of bioactive molecules. Although bile acids are known to affect host metabolism, cancer progression and innate immunity, it is unknown whether they affect adaptive immune cells such as T helper cells expressing IL-17a (Th17 cells) and regulatory T cells (Tregs). By screening a library of bile acid metabolites, we identified two distinct derivatives of lithocholic acid (LCA), 3-oxoLCA and isoalloLCA, as T cell regulators. 3-oxoLCA inhibited Th17 cell differentiation by directly binding to its key transcription factor RORγt (retinoid-related orphan receptor γt) and isoalloLCA enhanced Treg differentiation through the production of mitochondrial reactive oxygen species (mitoROS), leading to increased FoxP3 expression. IsoalloLCA-mediated Treg enhancement required an intronic FoxP3 enhancer, the conserved noncoding sequence 3 (CNS3), a distinct mode of action from previously-identified Treg enhancing metabolites that require CNS1. Administration of 3-oxoLCA and isoalloLCA to mice reduced Th17 and increased Treg cell differentiation in the intestinal lamina propria. Our data suggest novel mechanisms by which bile acid metabolites control host immune responses by directly modulating the Th17 and Treg balance.

To identify bile acids with T cell modulatory effects, we screened ~30 compounds. Our screen included both primary bile acids, synthesized by the host, and secondary bile acids, produced by bacterial modification of primary bile acids (FIG. 5). Naïve $CD4^+$ T cells were isolated from wild-type C57BL/6J (B6) mice and cultured with bile acids under Th17 differentiation conditions and, as a counter-screen, Treg differentiation conditions (FIG. 6). Strikingly, two distinct derivatives of LCA were found to significantly affect Th17 and Treg cell differentiation. While 3-oxoLCA inhibited Th17 differentiation, as shown by reduced IL-17a, isoalloLCA enhanced Tregs, as shown by increased FoxP3 expression (FIG. 1a, b and 6d, e). Although isoalloLCA strongly enhanced FoxP3 expression in the presence of low, but not high, TGF-β concentrations (FIGS. 1a and 7a-c), its Treg-enhancing activity required TGF-β, because pretreatment of cells with anti-TGF-β antibody prevented FoxP3 enhancement (FIG. 7d, e).

The modulatory effects of 3-oxoLCA on Th17 cells and isoalloLCA on Tregs were cell-type specific, as neither compound affected T cell differentiation into Th1 or Th2 cells assessed by the expression of the cytokines IFN-γ and IL-4 and the transcription factors T-bet and GATA3 (FIG. 1a, b and 7f, g). Although 3-oxoLCA did not affect Tregs (FIGS. 1b and 6e), isoalloLCA reduced Th17 cell differentiation by ~50% without affecting RORγt expression (FIG. 1a, b and 7 h). Both compounds exhibited dose-dependent effects (FIG. 8a). While 3-oxoLCA did not affect cell proliferation, isoalloLCA addition to T cells led to reduced proliferation compared to DMSO control (FIG. 8b). IsoalloLCA treatment did not impair cell viability (FIG. 8c) or T cell receptor (TCR)-mediated activation, as indicated by similar expression of TCR activation markers such as CD25, CD69, Nur77 and CD44 (FIG. 8d). TCR activation promotes Treg-enhancement by isoalloLCA, as increasing TCR activation with higher concentrations of anti-CD3 resulted in stronger effects on FoxP3 expression without affecting cell viability (FIG. 8e, f).

Figure 2:
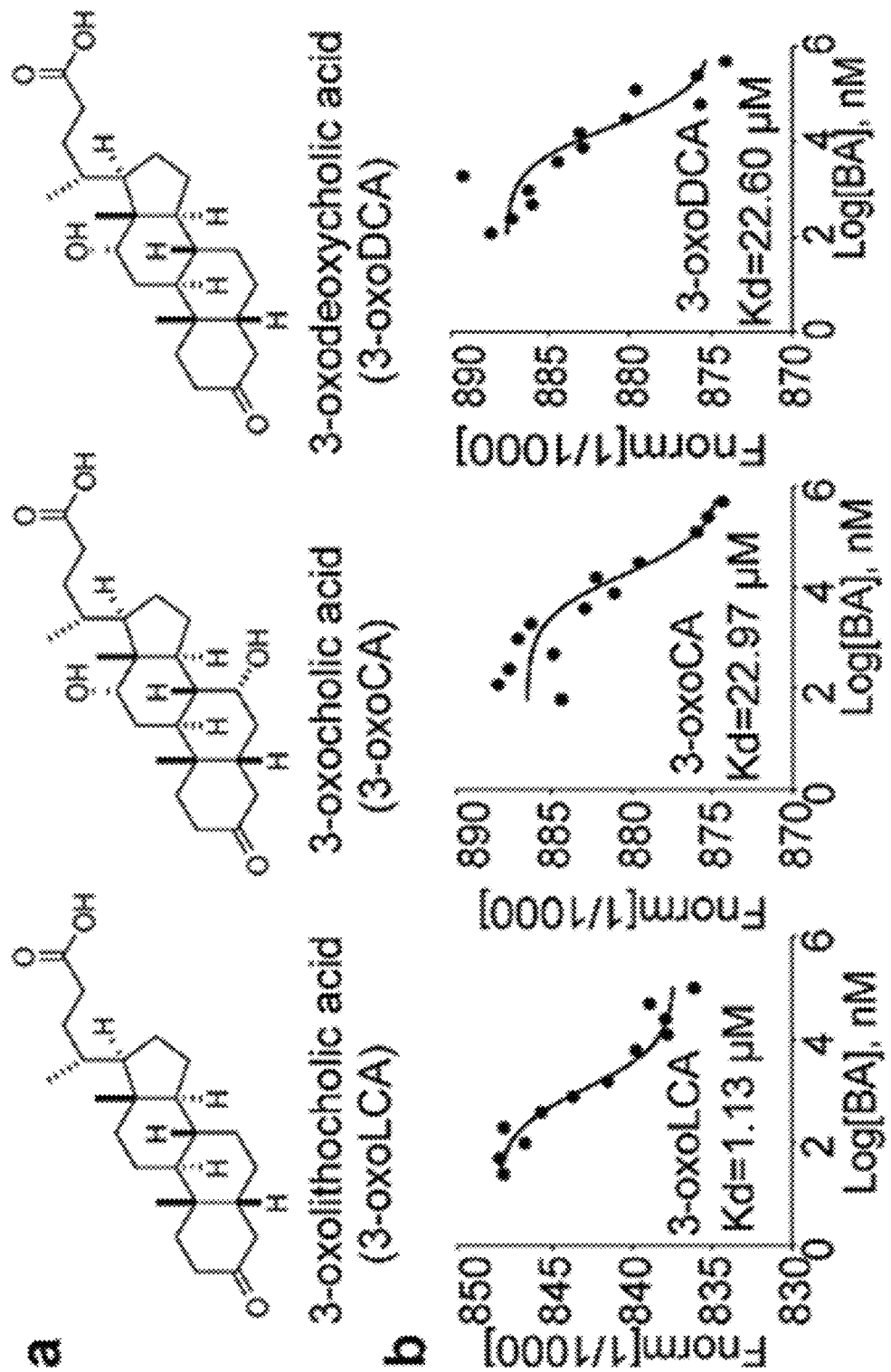
FIG. 2 shows 3-oxoLCA binds to RORγt and inhibits its transcriptional activity. a, Chemical structures of 3-oxoLCA, 3-oxocholic acid (3-oxoCA) and 3-oxodeoxycholic acid (3-oxoDCA). b, Microscale thermophoresis assay. 3-oxoLCA binds to RORγt LBD at a much lower Kd value than the other two structurally similar bile acids. c and d, Flow cytometric analyses and quantification of IL-17a production from mouse (n=3/group), naïve CD4⁺ T cells cultured for 3 days under Th17 polarization condition. DMSO or bile acids at 20 μM were added 18 h after cytokine addition. e, RORγt luciferase reporter assay in HEK293 cells treated with a positive control ML209 (2 μM), 3-oxoLCA (10 μM), 3-oxoCA (10 μM), 3-oxoDCA (10 μM), or DMSO. The ratio of firefly to *Renilla* luciferase activity is presented on the y-axis (n=3/group). n, number of biologically independent samples. Data are shown as the mean±standard deviation by unpaired t-test with 2-tailed p-value.
Figure 2:
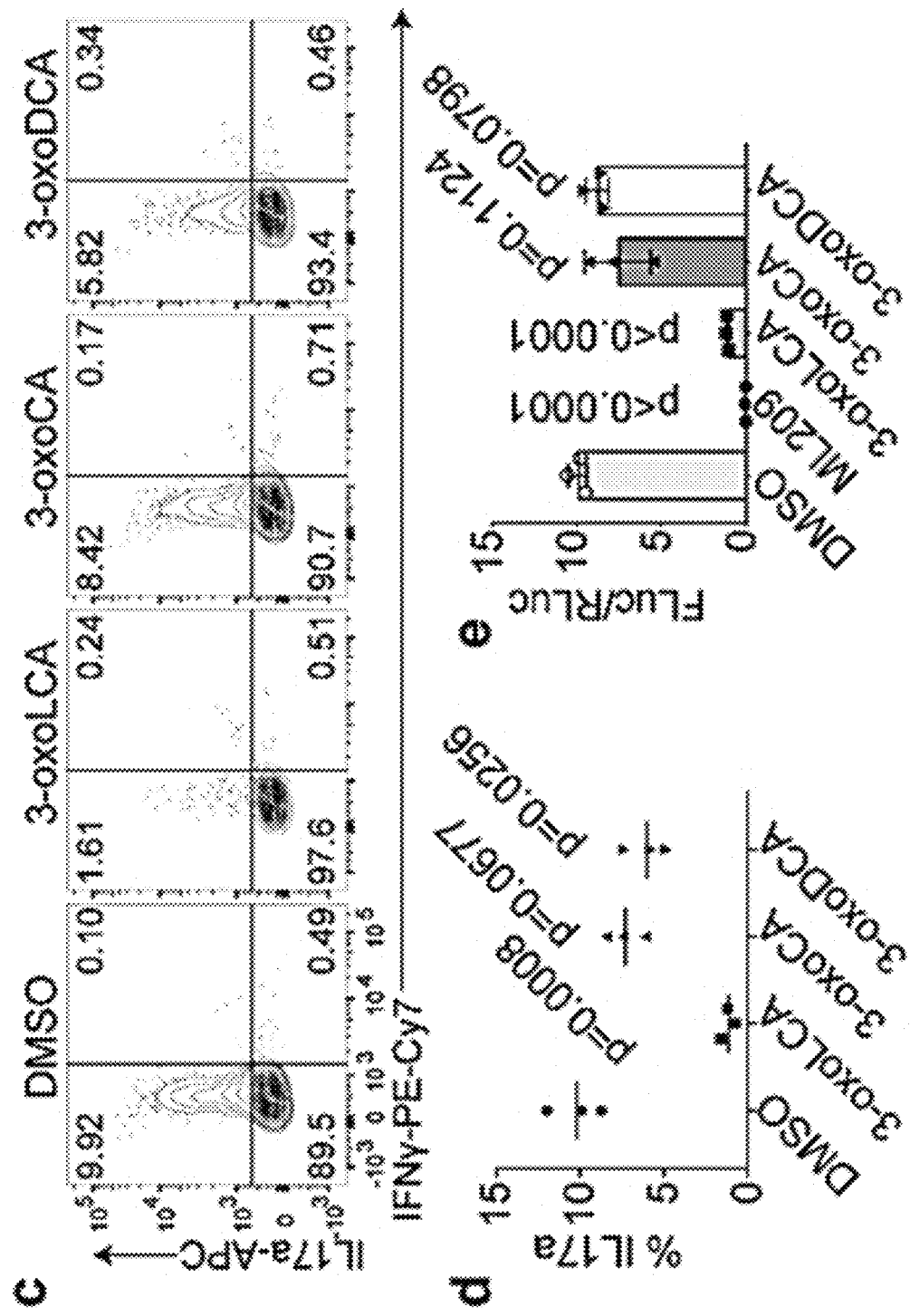

3-oxoLCA inhibits Th17 cell differentiation. We next examined if 3-oxoLCA physically interacts with the RORγt protein in vitro. A microscale thermophoresis (MST) assay was performed with recombinant human RORγt ligand-binding domain (LBD). 3-oxoLCA exhibited a robust physical interaction with the RORγt LBD at the equilibrium dissociation constant (Kd) of ~1 μM. We also tested two other structurally similar 3-oxo derivatives of bile acids, 3-oxocholic acid (3-oxoCA) and 3-oxodeoxycholic acid (3-oxoDCA) (FIG. 2a) and demonstrated that these derivatives had ~20 times higher Kd values than 3-oxoLCA (FIG. 2b). Neither 3-oxoCA nor 3-oxoDCA inhibited Th17 cell differentiation as robustly as 3-oxoLCA (FIG. 2c, d). Next, we examined if 3-oxoLCA modulates the transcriptional activity of RORγt. We assayed the effect of the bile acids on firefly luciferase expression directed by a fusion protein of RORγt and Gal4-DBD (DNA-binding domain) in human embryonic kidney (HEK) 293 cells[14]. Cells treated with ML209, a specific RORγt antagonist, completely lost RORγt activity[19]. Likewise, 3-oxoLCA treatment significantly reduced the RORγt reporter activity (FIG. 2e). Altogether, these data suggest that 3-oxoLCA likely inhibits Th17 cell differentiation by physically interacting with RORγt and inhibiting its transcriptional activity.

Figure 3:
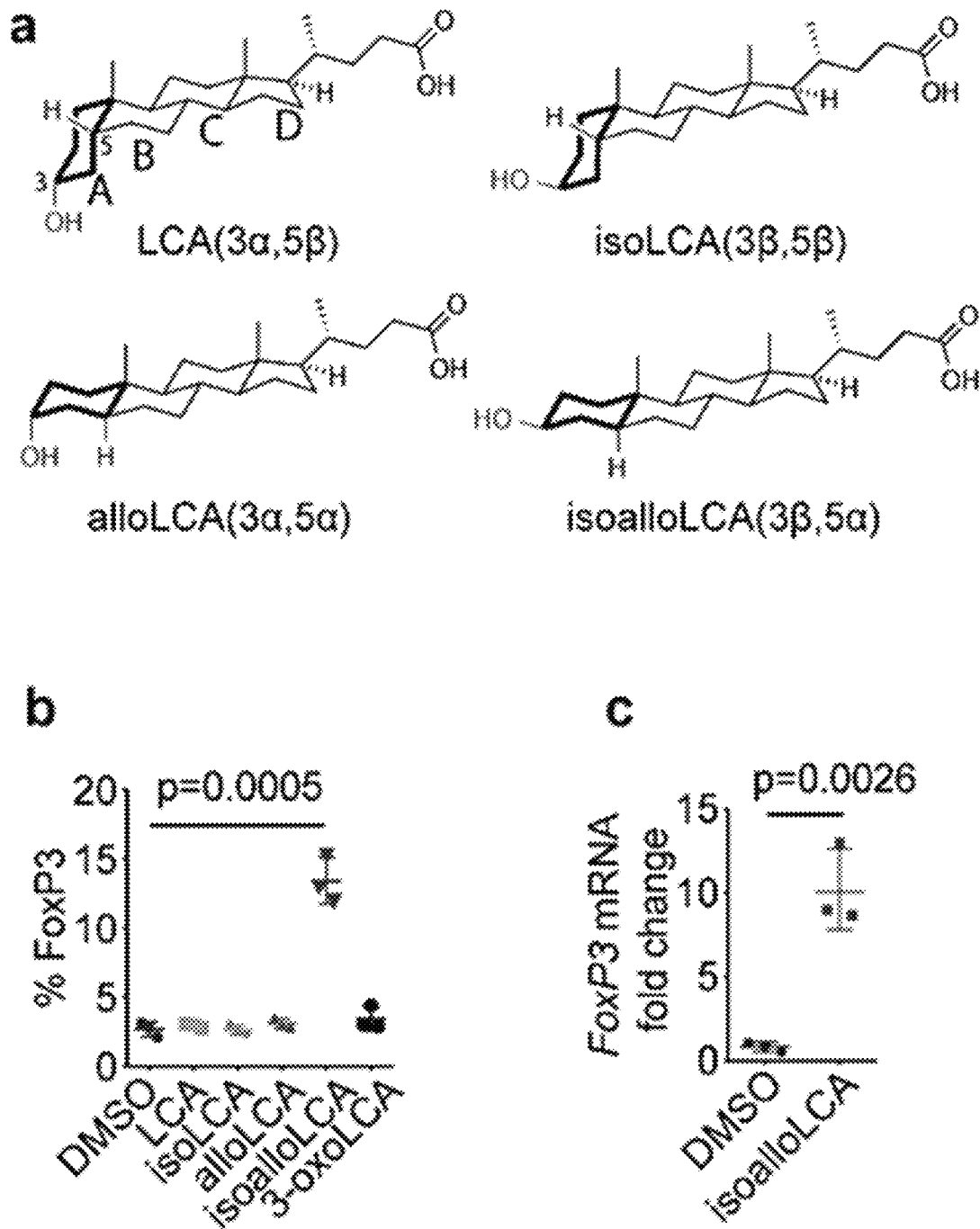
FIG. 3 shows mitoROS is necessary and sufficient for isoalloLCA-dependent enhanced expression of FoxP3. a, Chemical structures of LCA and its isomers: isoLCA, alloLCA and isoalloLCA. b, FoxP3 expression from mouse naïve CD4⁺ T cells cultured for 3 days with anti-CD3/28 and IL-2. DMSO or bile acids at 20 μM were added to cell culture (n=3/group). c, qPCR analysis for FoxP3 transcripts in DMSO- or isoalloLCA- (20 μM) treated cells (n=3/group). d, Diagram of the FoxP3 gene locus containing the promoter region (Pro) and intronic enhancer regions (CNS1, CNS2 and CNS3). e and f, Flow cytometric analyses and quantification of CD4⁺ T cells stained intracellularly for FoxP3. Naïve CD4⁺ T cells isolated from wild-type control, CNS1, CNS2 or CNS3 knockout mice were cultured with anti-CD3/28 and IL-2, in the presence of DMSO or isoalloLCA (20 μM) (n=3/group). g, Mitochondrial ROS production measured by mitoSOX staining with T cells cultured in the presence of DMSO or LCA isomers for 48 h. Staining intensity was reported as mean fluorescence intensity from flow cytometry analysis (PE channel). Different conditions were then normalized as fold change to the values of DMSO condition (n=3/group). h and i, Representative FACS plots and quantification of T cells stained intracellularly for FoxP3, cultured with anti-CD3/28, IL-2 and TGF-β (0.05 ng/ml) in the presence of DMSO, LCA, isoalloLCA (20 μM) or retinoic acid (1 nM), with DMSO or mitoQ (0.5 μM) for 72 h (n=3/group). j and k, Flow cytometric analyses and quantification of CD4⁺ T cells stained intracellularly for FoxP3. Naïve CD4⁺ T cells isolated from control or CNS3 knockout mice were cultured with anti-CD3/28 and IL-2 in the presence of DMSO or mitoPQ (10 μM) (n=3/group). n, number of biologically independent samples. Data are shown as the mean±standard deviation by unpaired t-test with 2-tailed p-value.
Figure 3:
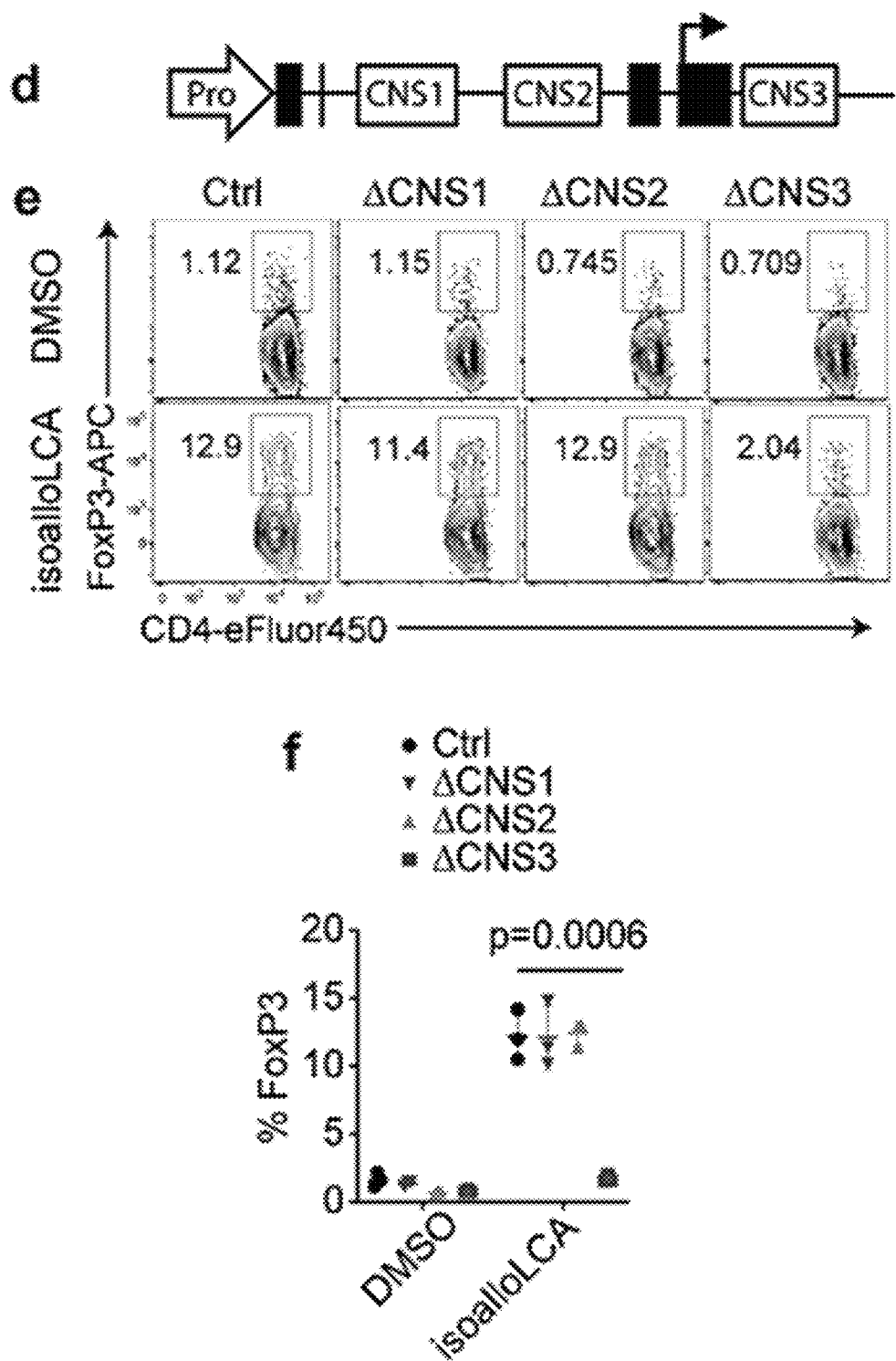
Figure 3:
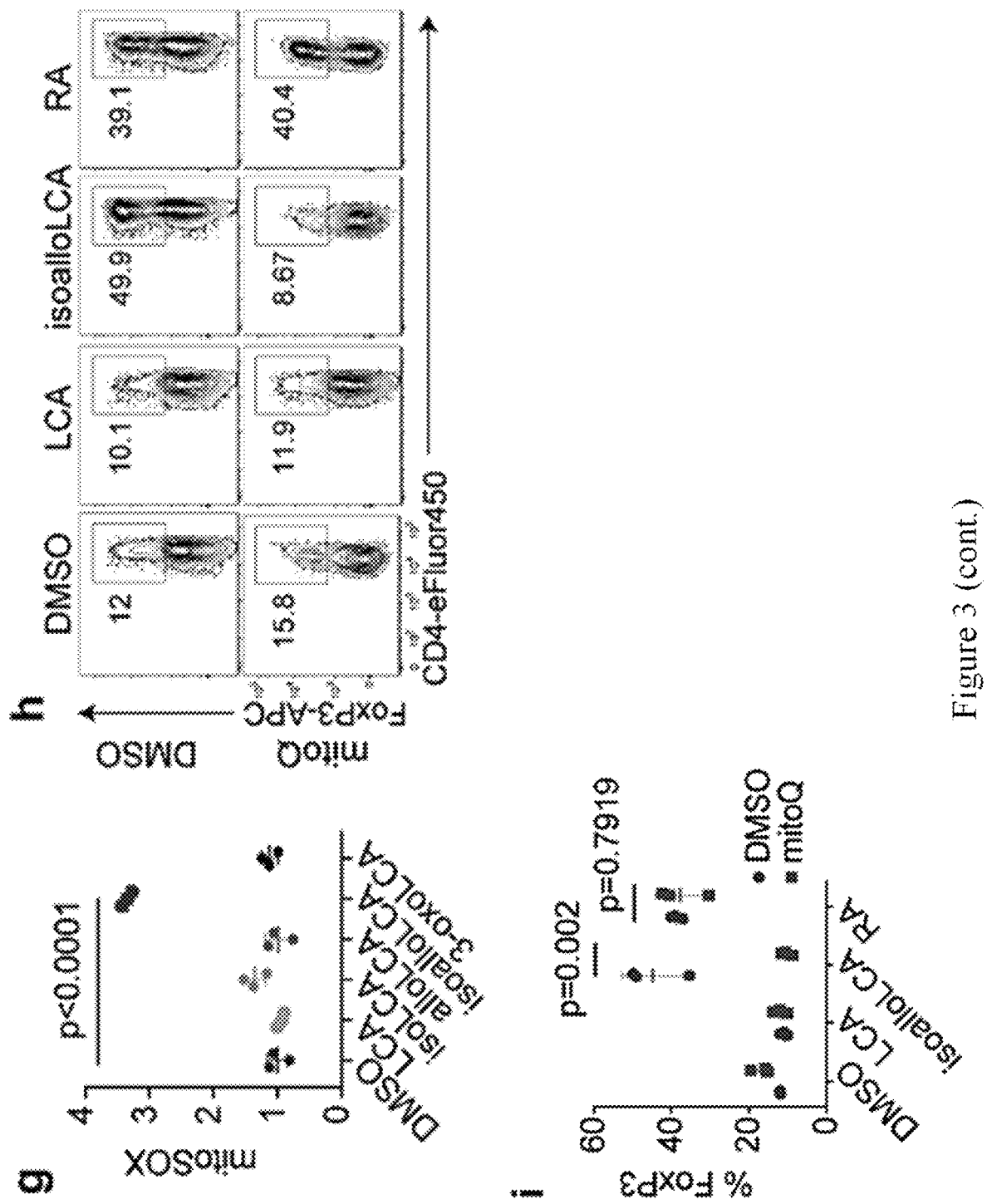
Figure 3:
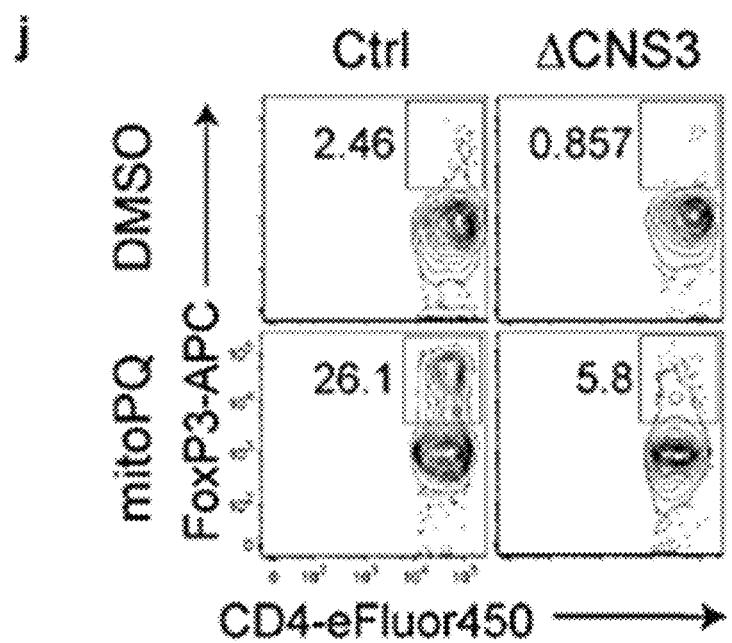
Figure 3:
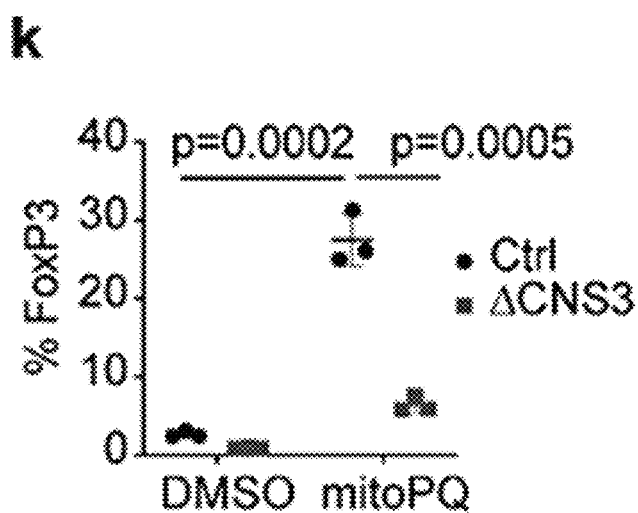

IsoalloLCA promotes Treg differentiation. We next sought to uncover the mechanism by which isoalloLCA exerts its enhancing effects on Tregs. LCA has a 3α-hydroxyl group as well as a cis 5f-hydrogen configuration at the A/B ring junction and can undergo isomerization, presumably via the actions of gut bacterial enzymes[2], to form isoLCA (30,50), alloLCA (3α,5α) or isoalloLCA (3β,5α) (FIG. 3a). Among LCA isomers, isoalloLCA has the lowest log D value (2.2), comparable to previously reported log D values of chenodeoxycholic acid (CDCA, 2.2) and ursodeoxycholic acid (UDCA, 2.2) (Table 2), suggesting isoalloLCA is less lipophilic than other isomers. IsoalloLCA, but not the other LCA isomers, enhanced FoxP3 expression, confirming that both the 30-hydroxyl group and trans (5α-hydrogen) A/B ring configuration of isoalloLCA are required for Treg enhancement (FIG. 3b). Compared to DMSO-treated cells, isoalloLCA-treated cells inhibited T effector cell proliferation in vitro, indicating they had acquired regulatory activity (FIG. 9a, b). T cells isolated from FoxP3-GFP reporter mice exhibited both increased FoxP3 mRNA expression (FIG. 3c) and enhanced GFP levels following isoalloLCA treatment (FIG. 9c). Thus, isoalloLCA-induced enhanced expression of FoxP3 occurs at the FoxP3 mRNA transcriptional level.

FoxP3 transcription is regulated by three conserved non-coding enhancers, termed CNS1, 2 and 3 (FIG. 3d), which have distinct roles in Treg development, stability and function[20-22]. Treg-promoting small molecules such as the bacterial metabolite butyrate and the vitamin A derivative retinoic acid (RA) enhance FoxP3 expression in a CNS1-dependent manner[23,24]. TGF-β also partially requires CNS1 for its Treg-promoting activity due to the binding of its downstream signaling molecule SMAD3 to the CNS1 enhancer[22,25]. Whereas $CD4^+$ T cells from mice with deletions in CNS1 and CNS2 up-regulated FoxP3 in response to isoalloLCA, cells lacking CNS3 failed to respond (FIG. 3e, f). In contrast, RA and TGF-β boosted Treg differentiation in CNS3-deficient cells, albeit with reduced efficiency (FIG. 9d). Thus, unlike other small molecules that promote Treg differentiation in a CNS1-dependent manner, the FoxP3-enhancing activity of isoalloLCA requires CNS3.

We investigated other known regulators of T cell function. The transcription factor cRel binds to the CNS3 enhancer to induce FoxP3 expression[22]. We found that WT and cRel-deficient cells express similar levels of FoxP3 upon isoalloLCA treatment (FIG. 9e, f). LCA targets the vitamin D receptor (VDR)[26] and the farnesoid X receptor (FXR)[21]. VDR was also implicated in the modulation of both Th17 and Treg cell function[28-31]. Compared to a DMSO-treated control, isoalloLCA-treated cells deficient in VDR or FXR had similar amounts of FoxP3 induction (FIG. 9g). Thus, CNS3-dependent activation of FoxP3 by isoalloLCA is unlikely to be mediated through the actions of cRel, VDR or FXR. VDR and FXR also failed to contribute to the suppressive activities of 3-oxoLCA on Th17 cells (FIG. 9h). Of note, conjugating glycine to 3-oxoLCA or isoalloLCA reduced their immunomodulatory effects (FIG. 9i-k).

CNS3 was previously implicated in Treg cell development by promoting epigenetic modifications such as H3K27 acetylation (H3K27Ac) and H3K4 methylation at the FoxP3 promoter region[21]. Cells treated with isoalloLCA, compared to those treated with DMSO, had increased H3K27Ac levels at the FoxP3 promoter region (FIG. 10a). Consistent with this, isoalloLCA treatment increased histone acetyltransferase p300 recruitment (FIG. 10b). However, isoalloLCA did not affect H3K4 methylation (FIG. 10c). A pan-bromodomain inhibitor iBET that antagonizes H3K27Ac prevented isoalloLCA-dependent enhancement of FoxP3 in a dose-dependent manner (FIG. 10d, e). In line with previous work[21], CNS3 deficiency not only reduced basal levels of H3K27Ac but also abrogated the isoalloLCA-dependent increase of H3K27Ac at the FoxP3 promoter region (FIG. 10f). Therefore, CNS3 is likely needed to establish a permissible chromatin landscape, whereupon the promoter region is further acetylated following isoalloLCA treatment.

Increased mitoROS enhances FoxP3 expression. Cellular metabolism and epigenetic modification are intricately related. For example, byproducts of mitochondrial metabolism serve as substrates for histone acetylation and methylation[32]. Tregs mainly rely on oxidative phosphorylation (OxPhos) for their energy production[33-35]. Recent studies identified two metabolites, 2-hydroxyglutarate and D-mannose, that promote Treg generation by modulating mitochondrial activities[36,37]. To assess whether isoalloLCA affects OxPhos, we measured the oxygen consumption rate (OCR), with T cells cultured for 48 hours following DMSO or isoalloLCA treatment. At this time point, FoxP3 is not yet strongly induced, thus making it possible to assess isoalloLCA effects on cellular metabolism before cells are fully committed to becoming Tregs. Compared to DMSO, isoalloLCA treatment increased OCR, both in WT and CNS3-KO cells (FIG. 10g), suggesting that isoalloLCA treatment increases mitochondrial activity. Reactive oxygen species (ROS) are produced as byproducts of mitochondrial OxPhos. Whereas D-mannose increases cytoplasmic ROS production[37], isoalloLCA treatment led to increased production of mitochondrial ROS (mitoROS) without affecting cytoplasmic ROS (FIGS. 3g and 10h, i). Unlike isoalloLCA, other LCA isomers failed to increase mitoROS production (FIG. 3g). Furthermore, isoalloLCA-treated cells displayed a modest, but significant, increase in total mitochondrial mass and mitochondrial membrane potential (FIG. 10j, k). To test if mitoROS is directly involved in enhanced Treg differentiation by isoalloLCA, we employed mitoQ, a mitochondrially-targeted antioxidant, to reduce ROS levels in mitochondria (FIG. 10l). Importantly, in the presence of mitoQ, isoalloLCA was no longer effective in enhancing Treg differentiation (FIG. 3h, i). In contrast, RA-dependent induction of Tregs was unaffected by mitoQ treatment (FIG. 3h, i). We next investigated if mitoROS production is responsible for the enhanced H3K27Ac levels at the FoxP3 promoter of isoalloLCA-treated cells. Co-treating cells with isoalloLCA and mitoQ decreased H3K27Ac levels compared to those treated with isoalloLCA only (FIG. 10m). Stronger TCR stimulation that enhances FoxP3 expression (FIG. 8d, e) also increased mitoROS production (FIG. 10n)[38]. Although TGF-β, which is essential for the FoxP3-enhancing activity of isoalloLCA (FIG. 7d, e), was not required for the increased mitoROS production (FIG. 10o), it was required for the isoalloLCA-induced acetylation of H3K27 at the FoxP3 promoter (FIG. 10m). Because FoxP3 itself enhances mitochondrial OxPhos[39], and FoxP3-expressing Tregs had higher mitoROS levels compared to other CD4+ T cell subsets (FIG. 10p), we investigated if increased mitoROS production was a secondary effect of enhanced FoxP3 expression. CNS3-deficient cells that did not express high levels of FoxP3 in response to isoalloLCA treatment nevertheless exhibited enhanced OxPhos and increased levels of mitoROS (FIGS. 3e, f and 10g, q). We then investigated whether mitoROS is sufficient to promote Treg differentiation using the mitochondria-targeted redox cycler, mitoParaquat (mitoPQ)[40]. The addition of mitoPQ to T cell culture was sufficient to enhance mitoROS production and Treg differentiation in a dose-dependent manner (FIG. 10r, s). Like isoalloLCA, Treg differentiation induced by mitoPQ required the CNS3 enhancer and TGF-β (FIGS. 3j, k and 10t). Taken together, our data support a model in which isoalloLCA promotes Treg differentiation by enhancing mitoROS production and increasing H3K27 acetylation at the FoxP3 promoter region, which also requires TGF-β-induced signaling (FIG. 10u).

Figure 1:
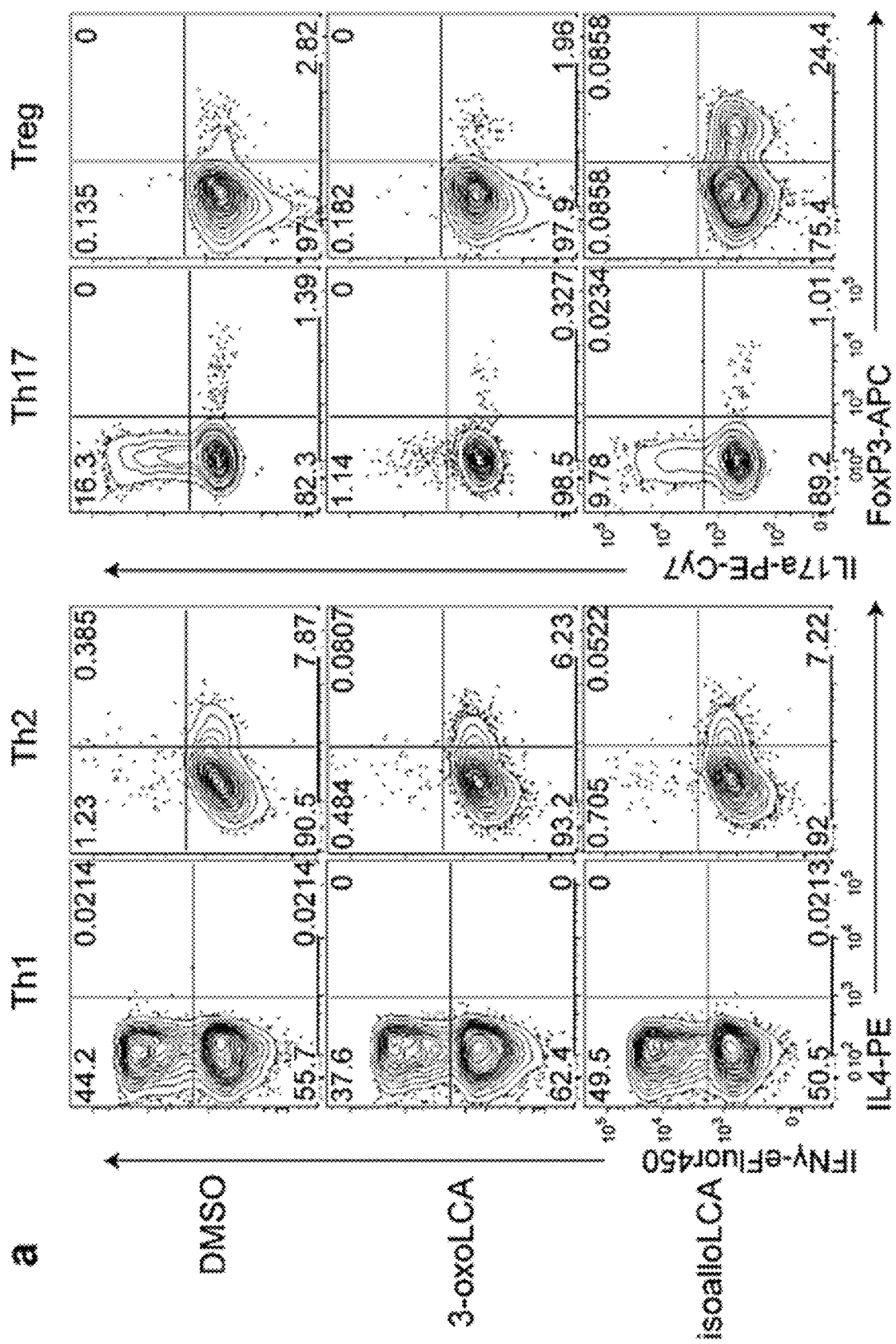
FIG. 1 shows 3-oxoLCA inhibits Th17 cell differentiation while isoalloLCA enhances Treg differentiation. a and b, Flow cytometry and its quantification of intracellular staining for IFN-γ and IL-4 or IL-17a and FoxP3 in sorted naïve T cells from wild-type B6 mice activated and expanded in the presence of mouse Th1, Th2, Th17 and Treg polarizing cytokines (n=4, 3, 4, 3). A low concentration of TGF-β (0.01 ng/ml) was used for Treg culture. DMSO, 3-oxoLCA (20 μM) or isoalloLCA (20 μM) was added on day 0 and CD4⁺ T cells were gated for analyses on day 3 for Th17 and Treg, day 5 for Th1 and Th2. n, number of biologically independent samples. Data are shown as the mean±standard deviation by unpaired t-test with 2-tailed p-value.
Figure 1:
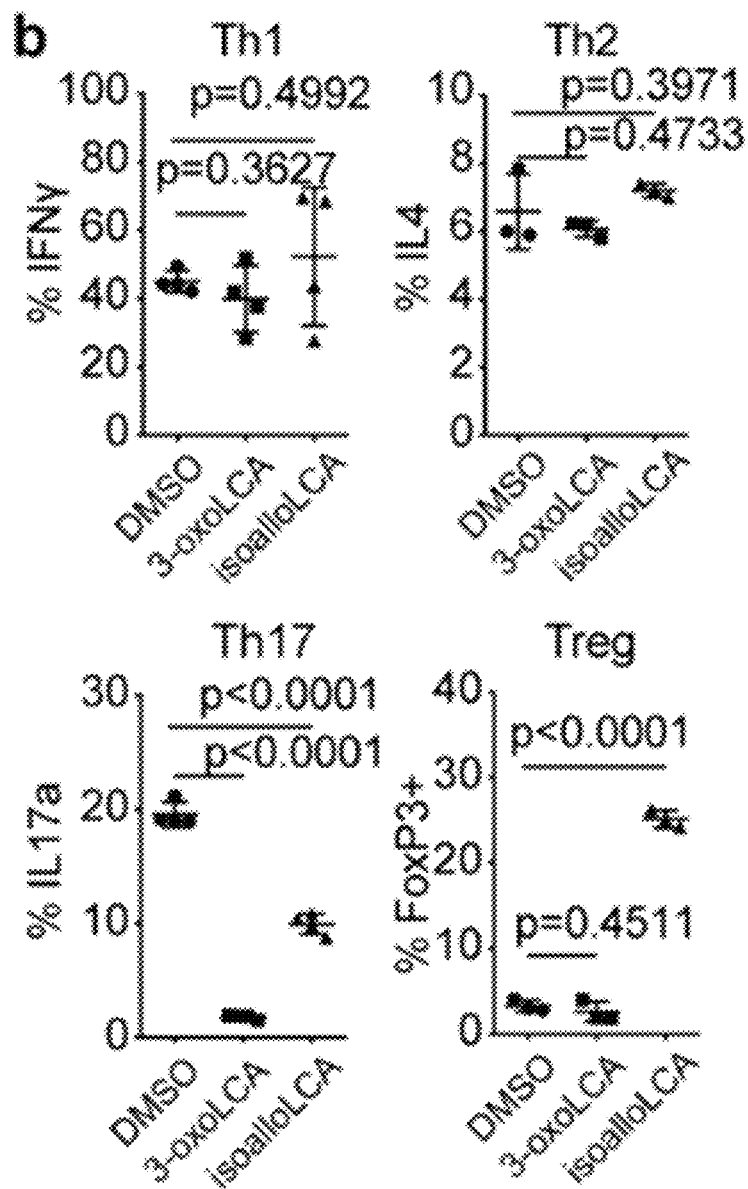
Figure 4:
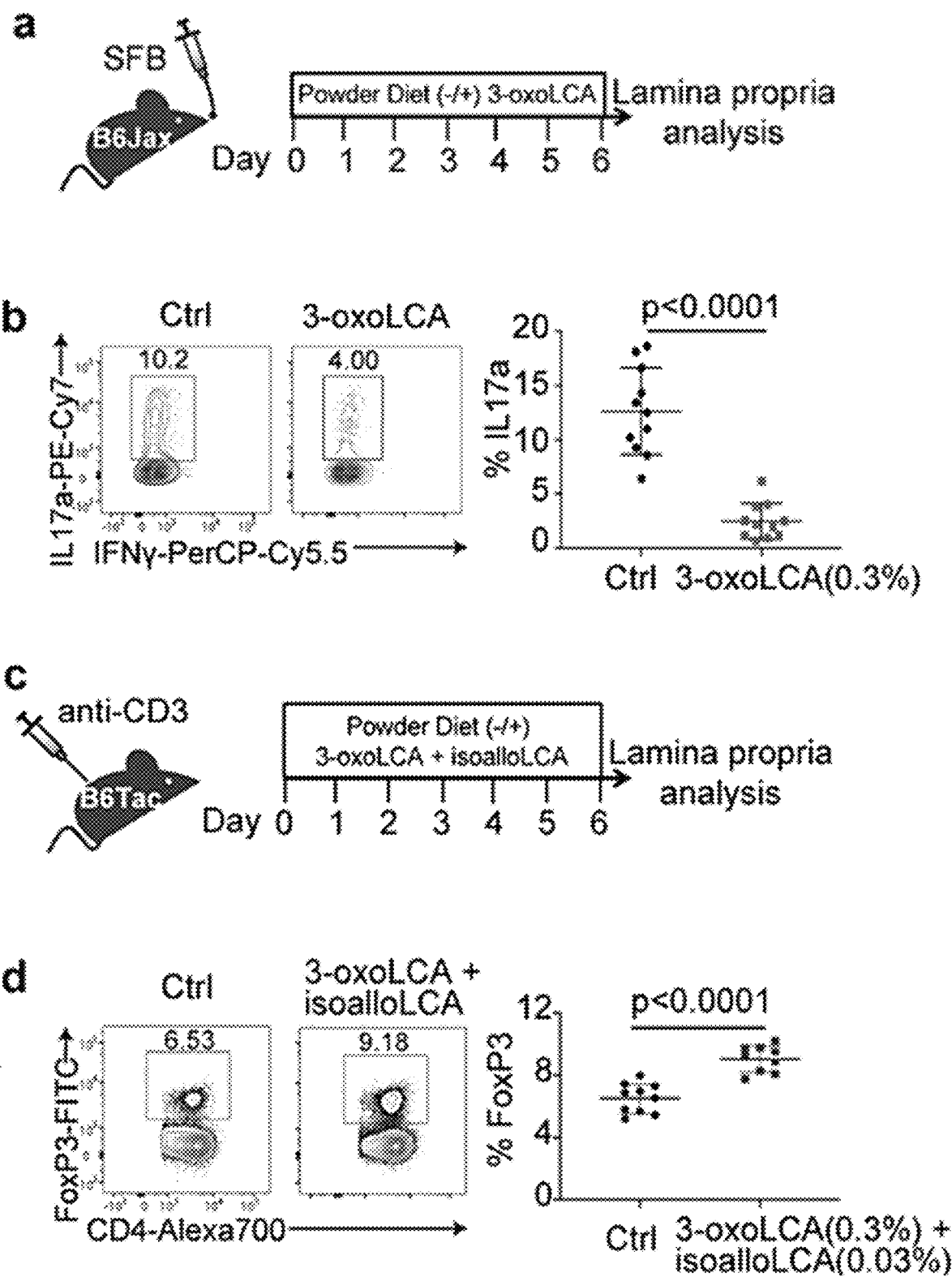
FIG. 4 shows 3-oxoLCA inhibits Th17 development while isoalloLCA enhances Treg cells in vivo. a and b, Experimental scheme (a) and flow cytometric analysis (b) of Th17 induction by SFB. Jax-B6 animals were gavaged with SFB-rich fecal pellets and kept on 3-oxoLCA (0.3%) for a week (n=11 mice/group). c and d, Experimental scheme (c) and flow cytometric analysis (d) of anti-CD3 experiment with a mixture of 3-oxoLCA+isoalloLCA (n=10/9 mice for Ctrl/3-oxoLCA+isoalloLCA). B6 animals were i.p. injected with anti-CD3 and fed a control diet or mixture of 3-oxoLCA (0.3%)+isoalloLCA (0.03%) during the experiments. e and f, Experimental scheme (e) and flow cytometric analysis (f) of T cells isolated from the ileal lamina propria. Bone marrow cells from WT (CD45.1) and ΔCNS3 (CD45.2) mice were mixed at a 1:1 ratio and transferred into irradiated WT (CD45.1) recipient mice. Five weeks after the transfer, recipient mice were fed a control diet or a diet containing a mixture of 3-oxoLCA (0.3%)+isoalloLCA (0.03%), followed by an anti-CD3 injection (n=10 mice/ group). Data shown as the mean±standard deviation by unpaired t-test with 2-tailed p-value.
Figure 4:
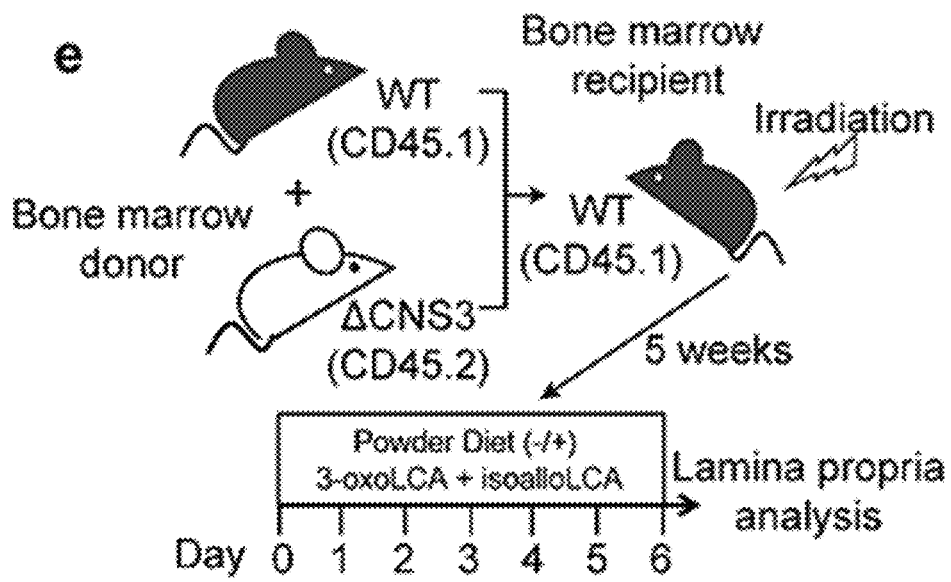
Figure 4:
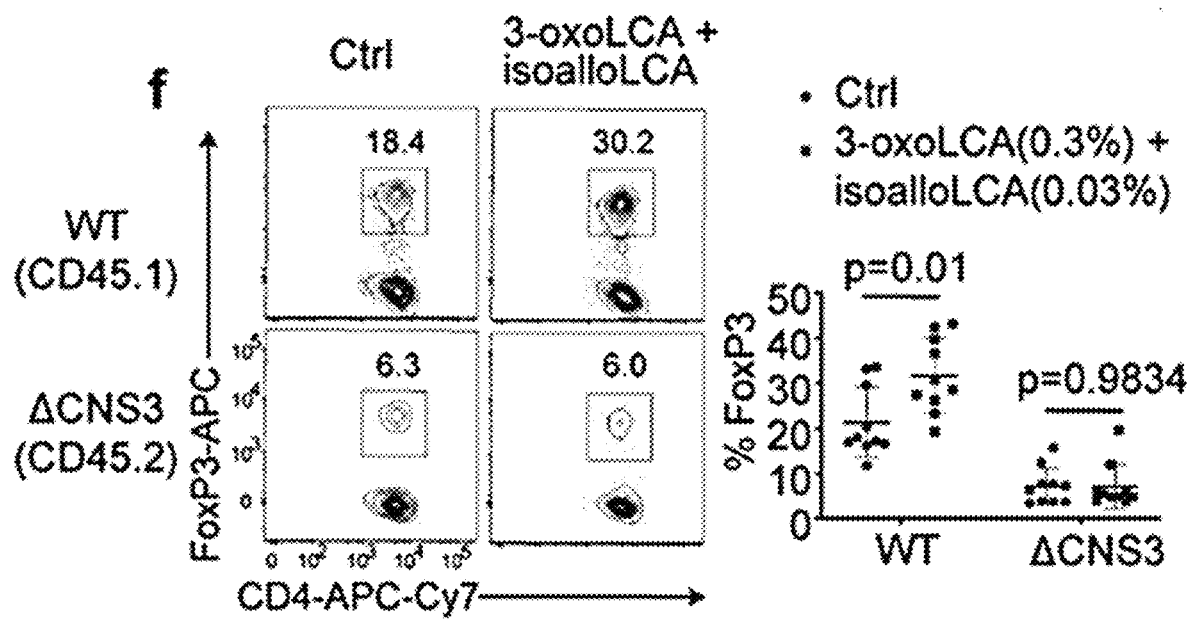

Bile acids modulate T cell activities in vivo. We next examined whether 3-oxoLCA and isoalloLCA influence Th17 and Treg cell differentiation in vivo using the mouse model. Segmented filamentous bacteria (SFB), a murine commensal, is known to induce Th17 cell differentiation in the small intestine of B6 mice[41]. C57BL/6NTac mice from Taconic Biosciences (Tac) have abundant Th17 cells in their small intestine owing to the presence of SFB. In contrast, $C_{57}BL/6J$ mice from Jackson Laboratories (Jax), which lack SFB, have few intestinal Th17 cells. To determine whether 3-oxoLCA suppresses Th17 cell differentiation in vivo, we gavaged Jax-B6 mice with an SFB-containing fecal slurry and fed these animals either a control diet or 0.3% (w/w) 3-oxoLCA-containing chow for one week (FIG. 4a). The resulting average concentration of this metabolite in cecal contents was 24 picomol/mg of wet mass (approximately equivalent to µM) (FIG. 11a, b). This concentration was sufficient to suppress Th17 differentiation in vitro (FIG. 1c). Indeed, 3-oxoLCA treatment significantly reduced the percentage of ileal Th17 cells (FIG. 4b). When we quantified the average levels of 3-oxoLCA in the stool of human patients with ulcerative colitis or in the ceca of conventionally housed mice, we observed a mean concentration of 23 or 1.0 picomol/mg, respectively (FIG. 11c, d). SFB colonization levels were comparable between control and 3-oxoLCA-treated groups, suggesting that the change in Th17 cell percentage was not due to a decrease in SFB colonization (FIG. 11e). In addition, Tac-B6 mice with pre-existing SFB had reduced levels of Th17 cell percentages when fed with 3-oxoLCA compared to those fed with vehicle (FIG. 11f-h). 3-oxoLCA treatment did not affect Treg percentages (FIG. 11i). Even under gut inflammatory conditions induced by anti-CD3 injection, known to produce a robust Th17 cell response[18,42] mice treated with 1%, but not with 0.3%, 3-oxoLCA had reduced Th17 cell levels (FIG. 11j-1).

To examine the effects of isoalloLCA on Tregs in vivo, we fed SFB-colonized B6 mice a control diet or a diet containing 0.03% (w/w) isoalloLCA. IsoalloLCA alone was insufficient to enhance Treg percentages both at steady state (FIG. 11m) and following anti-CD3 treatment (FIG. 11n). We noted that 3-oxoLCA further enhanced Treg differentiation induced by isoalloLCA in vitro (FIG. 11o, p). In line with this observation, a mixture of 0.3% (w/w) 3-oxoLCA and 0.03% (w/w) isoalloLCA significantly enhanced the Treg population in mice treated with anti-CD3 compared to control diet (FIG. 4c, d). Consistent with the mechanism in vitro, this treatment led to increased mitoROS production among CD4+ T cells in the ileal lamina propria (FIG. 11q). Importantly, the 3-oxoLCA/isoalloLCA-induced enhanced FoxP3 expression in vivo was also dependent on the CNS3 enhancer because ACNS3, unlike WT, cells no longer responded to this treatment in a mixed bone marrow experiment (FIG. 4e, f). Feeding both isoalloLCA and 3-oxoLCA in chow resulted in an average concentration of 47 picomol/mg isoalloLCA in cecal contents (FIG. 11b). This concentration was sufficient to enhance Treg differentiation in vitro (FIG. 1c). The mean concentration of isoalloLCA in the stool of human ulcerative colitis patients was 2 picomol/mg and ranged from 0-17 picomol/mg (FIG. 11c). These values are within an order of magnitude of the concentrations observed in mice fed 0.03% isoalloLCA and 0.3% 3-oxoLCA, suggesting that the in vivo levels of isoalloLCA achieved are physiologically relevant.

We next asked whether the immunomodulatory roles of 3-oxoLCA and isoalloLCA are mediated through changes in the composition of the gut bacterial community. 16S rDNA sequencing with fecal samples of mice fed bile acid-containing diets revealed no significant perturbations in the gut bacterial community, compared to those on a control diet (FIG. 12a-e). Furthermore, 3-oxoLCA treatment reduced Th17 cell induction in the colons of germ-free B6 mice infected with Citrobacter rodentium (FIG. 12f, g). Thus, the Th17 and Treg modulatory activities of 3-oxoLCA and isoalloLCA do not likely require the presence of a community of commensal bacteria. Altogether, these data suggest that both 3-oxoLCA and isoalloLCA directly modulate Th17 and Treg cell responses in mice in vivo.

Lastly, we investigated if in vitro treatment of T cells with isoalloLCA produced Tregs competent to exert suppressive function in vivo. The same number of FoxP3+ T cells (CD45.2), sorted from T cell cultures with low or high TGF-β concentrations (TGF-β-lo/-hi Tregs) in the absence or presence of isoalloLCA, were adoptively transferred into Rag1 KO mice that had also received CD45RB$^{hi}$ naïve CD4+ T cells (CD45.1) (FIG. 13a, b). Mice that received CD45RB$^{hi}$ or CD45RB$^{hi}$ and TGF-β-lo Tregs developed significant weight loss and shortened colon phenotypes, both of which are indicators of colitis-associated symptoms (FIG. 13c-f). In contrast, adoptive transfer of isoalloLCA-treated Tregs protected mice from developing colitis-associated symptoms to the same degree as those transferred with TGF-β-hi Tregs (FIG. 13c-f). Tregs treated with isoalloLCA were more stable in terms of FoxP3 expression, compared to TGF-β-lo Tregs treated with DMSO, analyzed eight weeks post transfer (FIG. 13g-j). In addition, mice receiving isoalloLCA-treated Tregs had reduced numbers of CD45.1V T effector cells (FIG. 13k). Therefore, isoalloLCA likely promotes stability of Treg cells and enhances their function following adoptive transfer in vivo, leading to decreased proliferation of T effector cells.

Certain bile acids are thought to be tissue-damaging agents that promote inflammation due to their enhanced accumulation in patients with liver diseases and their chemical properties as detergents that disrupt cellular membranes[43]. Recent studies, however, have begun to reveal their anti-inflammatory roles, particularly in the innate immune system by suppressing NF-κB-dependent signaling pathways[44,45] and by inhibiting NLRP3-dependent inflammasome activities[11]. Our studies reveal additional anti-inflammatory roles of two LCA metabolites found in both humans and rodents[46-48] that directly affect CD4+ T cells: 3-oxoLCA suppresses Th17 differentiation while isoalloLCA enhances Treg differentiation. Our data suggest that both 3-oxoLCA and isoalloLCA are present in the stool samples of human colitis patients as well as in the ceca of conventionally-housed Jax-B6 mice (FIG. 11c, d). Importantly, both bile acids are completely absent in germ-free B6 mice (FIG. 11d). These data suggest that gut-residing bacteria may contribute to the production of 3-oxoLCA and isoalloLCA. Given the significant roles of Th17 and Treg cells in a wide variety of inflammatory diseases and their close relationship with gut-residing bacteria, our study suggests the existence of novel modulatory pathways that regulate T cell function through bile acid metabolites.

Key Reagent Table

| REAGENT | SOURCE | IDENTIFIER |
|---|---|---|
| Antibodies | | |
| FACS antibody | | |
| IFNγ | eBioscience | clone: XMG1.2 |
| IL-4 | Biolegend | clone: 11B11 |
| IL-17a | eBioscience | clone: eBio17B7 |
| Foxp3 | eBioscience | clone: FJK-16s |
| CD4 | eBioscience | clone: RM4-5 |
| CD3e | eBioscience | clone: 145-2C11 |
| CD45 | Biolegend | clone: 30-F11 |
| CD25 | eBioscience | clone: PC61.5 |
| CD69 | eBioscience | clone: H1.2F3 |
| CD44 | Biolegend | clone: IM7 |
| CD62L | eBioscience | clone. MEL-14 |
| CD45RB | Biolegend | clone: C363-16A |
| Nur77 | eBioscience | clone: 12.14 |
| ChIP antibody | | |
| Rabbit IgG | abcam | ab46540 |
| H3K27Ac | abcam | ab4729 |
| H3K4me1 | abcam | ab8895 |
| p300 | abcam | ab 14984 |
| Cytokines | | |
| IL-2 | PEPROTECH | 200-02 |
| IL-4 | R & D systems | 404-ML-010 |
| IL-6 | eBioscience | 14-8061-62 |
| IL-12 | PEPROTECH | 210-12 |
| TGFβ | PEPROTECH | 100-21 |
| hamster IgG | MP Biomedicals | 856984 |
| anti-CD3 | eBioscience | clone: 145-2C11 |
| anti-CD28 | eBioscience | clone: 37.51 |
| anti-IL-4 | eBioscience | clone: 11B11 |
| anti-IFNγ | eBioscience | clone: XMG1.2 |
| anti-TGFβ | eBioscience | clone: 1D11.16.8 |
| IgG1 isotype | eBioscience | clone: P3.6.2.8.1 |
| Chemicals | | |
| DMSO | Sigma | D8418 |
| 1,25VD3 | Sigma | D1530 |
| Retinoic acid | Sigma | R2625 |
| iBET | Millipore | 401010 |
| Aqua | ThermoFisher | L34957 |
| AnnexinV | eBioscience | BMS306FI/100 |
| CFSE | Biolegend | 423801 |
| mitoQ | Focus Biomolecules | 10-1363 |
| mitoSOX | ThermoFisher | M36008 |
| DCFDA | Sigma | D6883 |
| JC-1 | ThermoFisher | T3168 |
| PMA | Sigma | P1585 |
| Ionomycin | Sigma | I3909 |
| GolgiPlug | BD | 555029 |
| Seahorse drugs | | |
| XF mito stress kit | Agilent | 103015-100 |
| XF glycolysis kit | Agilent | 103020-100 |
| Bile Acids | | |
| screen library | Michael Fischbach lab | |
| 3-oxoLCA | Steraloids | C1750-000 |
| isoalloLCA | Steraloids | C0700-000 |
| isoLCA | Steraloids | C1165-000 |
| Bulk chemical synthesis | Michael Krout lab | |

Animals. C57BL/6, FoxP3-GFP, FXR-KO, VDR-KO, CD45.1, Rag1-KO mice were purchased from Jackson Laboratory. SFB-containing C57BL/6 mice were purchased from Taconic bioscience. FoxP3-CNS-KO and control mice were provided by the Ye Zheng Lab. All animal procedures were approved by the Institutional Animal Care and Use Committee at Harvard Medical School.

Chemical Synthesis of 3-oxoLCA, isoalloLCA, glyco-3-oxoLCA, and glyco-isoalloLCA. Detailed synthesis methods and characterization data are described above Measurement of lipophilicity. Partitioning Method: 2 µL of 10 mM stock solutions of each target compound was added to a 1 mL each of 50 mM ammonium bicarbonate (pH=8), and 1 mL of n-octanol in an Eppendorf tube. The resulting two-phase mixture was vortexed and then shaken for 18 h at 20° C. The two phases were then carefully separated into the aqueous sample (bottom layer), and organic sample (top-layer) and placed separately in autosampler vials and analyzed by LC-MS/MS. LC-MS Method: a Thermo q-Exactive Plus LC-MS equipped with an Ultimate 3000 HPLC was operated in negative ion mode after optimized to detect the [M– H]$^-$ of the bile acids. Mobile phase A was 5 mM ammonium acetate with 0.012% formic acid and mobile phase B was HPLC grade methanol. A Dikma Inspire C8 column (3 µm particle size, 100 mm length, 4.6 mm ID) was used for analysis. Each injection was 5 µL, and a constant flow rate of 0.400 L/min was used. The gradient started at 0% B and was held constant for 2 minutes. Then the mobile phase composition was linearly changed to 100% B over 8 minutes and held at 100% for the following 5 minutes. The mobile phase composition was changed to 0% B over the following 0.1 minutes and the system was allowed to equilibrate to starting conditions over 1.9 minutes. Standards of all targets were used to establish retention times. Better than 2 ppm mass accuracy was obtained on all measurements. The LC-MS analysis was done in triplicate, while the partitioning was done once for each target's [M– H]$^-$ ion. Calculation of log D: the total response of target in octanol was divided by the total response in the aqueous phase to get a partitioning coefficient. Then, log base 10 was taken and reported.

TABLE 2

Lipophilicity of bile acids

| Bile acid | Abbreviation | Log D (pH = 8.0) |
| --- | --- | --- |
| Lithocholic acid | LCA | 3.6 |
| Isolithocholic acid | isoLCA | 3.5 |
| Allolithocholic acid | alloLCA | 3.5 |
| Isoallolithocholic acid | isoalloLCA | 2.2 |
| 3-oxolithocholic acid | 3-oxoLCA | 2.4 |
| Deoxycholic acid | DCA | 2.7 |
| Chenodeoxycholic acid | CDCA | 2.2 |
| Ursodeoxycholic acid | UDCA | 2.2 |
| Obeticholic acid | OCA | 2.5 |
| Cholic acid | CA | 1.1 |

Human fecal specimens. Fecal samples were obtained from patients with active ulcerative colitis under an Institutional Review Board-approved protocol and informed consent was obtained at Weill Cornell Medicine (WCM). Active inflammation was defined by a Mayo endoscopic score of >1.

In vivo bile acid analysis. Stock solutions of all bile acids were prepared by dissolving the compounds in molecular biology grade DMSO (Sigma Aldrich). These solutions were used to establish standard curves. Glycocholic acid (GCA) or β-muricholic acid (β-MCA) (Sigma Aldrich) was used as the internal standard for mouse and human samples, respectively. Bile acids were extracted from mouse cecal and human fecal samples and quantified by Ultra-High Performance Liquid Chromatography-Mass Spectrometry (UPLC-MS) as previously reported[49]. The limits of detection of individual bile acids in tissues (in picomol/mg wet mass) are as follows: βMCA, 0.10; isoalloLCA, 0.45; isoLCA, 0.29; LCA, 0.12; alloLCA, 0.43; and 3-oxoLCA, 0.18.

In Vitro T Cell Culture. Naïve CD4$^+$ (CD62L$^+$ CD44$^-$ CD25$^-$ CD4$^+$) T cells were isolated from the spleens and the lymph nodes of mice of designated genotypes with FACS sorting. For certain experiments, naïve CD4$^+$ T cells were enriched using naïve CD4$^+$ T cell isolation kits (Miltenyi). Naïve CD4$^+$ T cells (40,000 cells) were cultured in a 96-well plate pre-coated with hamster IgG (MP Biomedicals) in T cell medium (RPMI, 10% fetal bovine serum, 25 mM glutamine, 55 µM 2-mercaptoethanol, 100 U/mL penicillin, 100 mg/mL streptomycin) supplemented with 0.25 µg/mL anti-CD3 (clone 145-2C11) and 1 µg/mL anti-CD28 (clone 37.51). For Th0 culture, T cells were cultured with the addition of 100 U/mL of IL-2 (PEPROTECH). For Th1 cell differentiation, T cells were cultured with the addition of 100 U/mL of IL-2, 10 µg/mL of anti-IL-4 (clone 11B11) and 10 ng/mL of IL-12 (PEPROTECH). For Th2 cell differentiation, T cells were cultured with the addition of 10 µg/mL of anti-IFNγ (clone XMG1.2) and 10 ng/mL of IL-4 (R&D Systems). For Th17 cell differentiation, T cells were cultured with the addition of 10 ng/mL of IL-6 (eBioscience) and 0.5 ng/mL of TGF-β (PEPROTECH). For Treg culture, T cells were cultured with the addition of 100 U/mL of IL-2 and various concentrations of TGF-β. For most in vitro experiments to test the effects of isoalloLCA, no additional TGF-β was added. Bile acids, retinoic acid (Sigma) or mitoQ (Focus Biomolecules), or mitoPQ (Sigma) were added either at 0 or 16 h time points. Compounds with low water solubility were sonicated before adding to the culture. Cells were harvested and assayed by flow cytometry on day 3. For ROS and mitochondrial membrane potential detection, cells cultured for 2 days were incubated with 5 µM of mitoSOX (ThermoFisher), 10 µM of DCFDA (Sigma) or 2 µM of JC-1 (ThermoFisher) for 30 min and assayed with flow cytometry.

Flow Cytometry. Cells harvested from in vitro culture or in vivo mice experiments were stimulated with 50 ng/mL PMA (Phorbol 12-myristate 13-acetate, Sigma) and 1 µM ionomycin (Sigma) in the presence of GolgiPlug (BD) for 4 h to determine cytokine expression. After stimulation, cells were stained with cell surface marker antibodies and LIVE/DEAD Fixable dye, Aqua, to exclude dead cells, fixed and permeabilized with a FoxP3/Transcription factor staining kit (eBioscience), followed by staining with cytokine- and/or transcription factor-specific antibodies. All flow cytometry analyses were performed on an LSR II flow cytometer (BD) and data were analyzed with FlowJo software (TreeStar).

Cell Proliferation Assay. Naïve CD4$^+$ T cells were labeled with 1 µM carboxyfluorescein succinimidyl ester (CFSE, BioLegend) and cultured for 3 days prior to FACS analysis.

In Vitro Suppression Assay. A total of 2.5×10$^4$ freshly-purified naïve CD4$^+$CD25-CD44-CD62Lhigh T cells (Tconv) from CD45.1 B6 mice were labeled with 1 µM CFSE, activated with soluble anti-CD3 (1 µg/mL) and 5×10$^4$ APCs in 96-well round-bottom plates for 3 days in the presence of tester cells (CD45.2). The CFSE dilution of CD45.1 Tconv cells was assessed by flow cytometry.

Mammalian Luciferase Reporter Assay. Reporter assays were conducted as previously described[14]. Briefly, 50,000 human embryonic kidney 293 cells per well were plated in 96-well plates in antibiotic-free Dulbecco's Modified Eagle Media (DMEM) containing 1% fetal calf serum (FCS). Cells were transfected with a DNA mixture containing 0.5 µg/mL of firefly luciferase reporter plasmid (Promega pGL4.31

[luc2P/Gal4UAS/Hygro]), 2.5 ng/mL of a plasmid containing Renilla luciferase (Promega pRL-CMV), and Gal4-DNA binding domain-RORγ (0.2 μg/mL). Transfections were performed using TransIT-293 (Mirus) according to the manufacturer's instruction. Bile acids or vehicle control were added 24 h after transfection and luciferase activity was measured 16 h later using the dual-luciferase reporter kit (Promega).

Microscale Thermophoresis Assay. The binding affinity of the compounds with RORγ ligand-binding domain (LBD) was analyzed by microscale thermophoresis (MST). Purified RORγ-LBD was labeled with the Monolith NT™ Protein Labeling Kit RED (NanoTemper Technologies). Serially-diluted compounds, with concentrations of 1 mM to 20 nM, were mixed with 55 nM labeled RORγ-LBD at room temperature and loaded into Monolith™ standard-treated capillaries. Binding was measured by monitoring the thermophoresis with 20% LED power and 'Medium' MST power on a Monolith NT.115 instrument (Nano Temper Technologies) with the following time setting: 5s Fluo, Before; 20s MST On; and 5s Fluo, After. Kd values were fitted using the NT Analysis software (Nano Temper Technologies).

RT-qPCR. Total RNA was isolated from cultured T cells using an RNeasy kit (Qiagen) and reverse transcribed using a PrimeScript RT kit (Takara). All qPCRs were run on the Bio-Rad CFX real-time system using iTaq Universal SYBR Green Supermix (Bio-Rad). j-actin was used as an internal control to normalize the data across different samples. Primers used for qPCR were as follows: FoxP3-F, 5'-ACTGGGGTCTTCTCCCTCAA-3' (SEQ ID NO:1); FoxP3-R, 5'-CGTGGGAAGGTGCAGAGTAG-3' (SEQ ID NO:2); β-actin-F, 5'-CGCCACCAGTTCGCCATGGA-3' (SEQ ID NO:3); β-actin-R, 5'-TACAGCCCGGGGAG-CATCGT-3' (SEQ ID NO:4).

Metabolic Assays. In vitro differentiated cells were cultured in the presence of DMSO or isoalloLCA for 48 h, and washed extensively before the assay. Oxygen consumption rate (OCR) was determined using a Seahorse XF96 Extracellular Flux Analyzer (Seahorse Bioscience) following protocols recommended by the manufacturer and according to the previously published method[51]. Briefly, cells were seeded on XF96 microplates (150,000 cells/well) that had been pre-coated with poly-D-lysine (Sigma) to immobilize cells. Cells were maintained in XF medium in a non-CO$_2$ incubator for 30 min before the assay. The Mito stress test kit (Agilent) was used to test OCR by sequential injection of 1 μM oligomycin, 1.5 μM FCCP and 0.5 μM rotenone/antimycin A. Data were analyzed by wave software (Agilent).

Chromatin Immunoprecipitations. Chromatin immunoprecipitation (ChIP) assays were performed according to standard protocol. Briefly, naïve CD4+ T cells were cultured for 48 h, and fixed for 10 min with 1% formaldehyde. Then 0.125 M glycine was added to quench the formaldehyde. Cells were lysed, and chromatin was harvested and fragmented by sonication at a concentration of $10^7$ cells/ChIP sample. Chromatin was immunoprecipitated with 5 μg of ChIP or IgG control antibodies at 4° C. overnight and incubated with protein G magnetic beads (ThermoFisher) at 4° C. for 2 h, washed, and eluted in 150 μL elution buffer. Eluate DNA and input DNA were incubated at 65° C. to reverse the crosslinking. After digestion with proteinase K, DNA was purified with the QIAquick PCR purification kit (Qiagen). The relative abundance of precipitated DNA fragments was analyzed by qPCR using SYBR Green Supermix (Bio-Rad). The primers used were as follows: FoxP3-Promoter-F, 5'-TAATGTGGCAGTTTCCCACAAGCC-3' (SEQ ID NO:5); FoxP3-Promoter-R, 5'-AATACCTCTCTGCCACTTTCGCCA-3' (SEQ ID NO:6); FoxP3-CNS1-F, 5'-AGACTGTCTG-GAACAACCTAGCCT-3' (SEQ ID NO:7); FoxP3-CNS1-R, 5'-TGGAGGTACAGAGAGGTTAAGAGCCT-3' ((SEQ ID NO:8); FoxP3-CNS2-F, 5'-ATCTGGC-CAAGTTCAGGTTGTGAC-3' (SEQ ID NO:9); FoxP3-CNS2-R, 5'-GGGCGTTCCTGTTTGACTGTTTCT-3' (SEQ ID NO:10); FoxP3-CNS3-F, 5'-TCTCCAGGCTTCAGAGATTCAAGG-3' (SEQ ID NO:11); FoxP3-CNS3-R, 5'-ACAGTGGGATGAGGATA-CATGGCT-3' (SEQ ID NO:12); FoxP3-ex10-F, 5'-CTG-CATCGTAGCCACCAGTA-3' (SEQ ID NO: 13); FoxP3-ex10-R, 5'-AACTATTGCCATGGCTTCC-3' (SEQ ID NO: 14); Hsp90ab-F, 5'-TTACCTTGACGG-GAAAGCCGAGTA-3' (SEQ ID NO:15); Hsp90ab-R, 5'-TTCGGGAGCTCTCTTGAGTCACC-3' (SEQ ID NO:16).

Isolation of Lamina Propria Lymphocytes. Gut tissues were harvested and treated with 1 mM DTT at room temperature for 10 min, and 5 mM EDTA at 37° C. for 20 min to remove epithelial cells, and dissociated in digestion buffer (RPMI, 1 mg/mL collagenase type VIII, 100 μg/mL DNase I, 5% FBS) with constant stirring at 37° C. for 30 min. Mononuclear cells were collected at the interface of a 40%/80% Percoll gradient (GE Healthcare). Cells were then analyzed by flow cytometry. The distal one-third of the small intestines was considered ileum.

Animal Experiments. For bile acid feeding experiments, the standard mouse diet in ground meal format (PicoLab Diet, #5053) was evenly mixed with a measured amount of bile acid compounds and provided in glass feeder jars and replenished when necessary. Colonization of mice with SFB was done with fresh fecal samples, derived from il23r; rag2 double-knockout mice that are known to carry much higher levels of SFB compared to conventional B6 mice. Fecal samples were homogenized in water using a 70-μm cell strainer and a 5 mL syringe plunger. Supernatant was introduced into mice using a 20G gavage needle at 250 μL/animal, approximately equal to the amount of ¼ mouse fecal pellets. Successful colonization was assessed by quantitative PCR, using the following primers: SFB-F, 5'-GACGCTGAGGCATGAGAGCAT-3' (SEQ ID NO: 17); SFB-R, 5'-GACGGCACGAATTGTTATTCA-3' (SEQ ID NO: 18); universal 16S-F, 5'-ACTCCTACGG-GAGGCAGCAGT-3' (SEQ ID NO: 19); universal 16S-R, 5'-ATTACCGCGGCTGCTGGC-3' (SEQ ID NO:20). For the *Citrobacter rodentium* infection experiment, age- and sex-matched germ-free mice were orally infected with approximately 1×10$^6$ CFU of *C. rodentium* and sacrificed for analysis at 6 days post-infection. Animals were kept in IsoCage system (Tecniplast) and fed an autoclaved diet with or without 0.3% 3-oxoLCA (w/w) during the experiment.

Bone Marrow Transfer. Bone marrow cells were isolated from the femur and tibia of B6 (CD45.1) mice or of CNS3 knockout mice (CD45.2). Red blood cells were removed by using an ammonium-chloride-potassium lysing buffer. The two populations were mixed at a 1:1 ratio and a total of 1×10$^7$ cells were transferred into each irradiated (1000 rad) CD45.1 mouse (5-weeks old) by retro-orbital injection. Sulfamethoxazole-trimethoprim (240 mg in 250 ml drinking water) was provided for 2 weeks after irradiation.

Adoptive Transfer Colitis. CD45RB$^{hi}$ adoptive transfer colitis was performed as described[51]. Briefly, isolated CD4+ CD25-CD45RB$^{hi}$ naïve T cells were sorted from wild-type B6 (CD45.1) mice by FACS and 0.5 million cells were adoptively transferred into each Rag1-KO recipient mouse.

In addition, the same number of in vitro cultured and sort-purified CD45.2+ FoxP3-GFP+ cells was transferred into the recipient mice. Naïve CD4 T cells, isolated from CD45.2 FoxP3-IRES-GFP mice, were cultured under TGF-β-lo (0.05 ng/ml TGF-β), isoalloLCA (20 μM isoalloLCA and 0.01 ng/ml TGF-β) or TGF-β-hi (1 ng/ml TGF-β) conditions. Mice were then monitored and weighed each week. At week 8, colon tissues were harvested, and lamina propria lymphocytes were analyzed by flow cytometry. H&E staining and disease scoring were performed by the Rodent Histopathology Core at Harvard Medical School.

Isolation of Fecal Bacterial Microbiota and 16S rRNA Gene Sequencing Analysis. Mouse fecal microbiota DNA was isolated by using QIAamp Fast DNA Stool Mini Kit (QIAGEN) according to the manufacturer's instructions. The samples were quantified using an Agilent 4200 Tapestation instrument, with corresponding Agilent Genomic DNA ScreenTape assays. The samples were then normalized to 12.5 ng of input in 2.5 μL (5 ng/μL), and amplified using IDT primers specific to the V3 and V4 region: Forward 5'-TCGTCGGCAGCGTCAGATGTGTATAAGA-GACAGCCTACGGGNGGCWGCAG-3' (SEQ ID NO:21) Reverse 5'-GTCTCGTGGGCTCG-GAGATGTGTATAAGAGACAGGAC-TACHVGGGTATCTAATCC-3' (SEQ ID NO:22). The amplification was done using the KAPA HiFi HotStart Ready Mix (2×) (Roche Sequencing Solutions). Residual primers were eluted away using Aline PCRCLean DX beads in a 0.8×SPRI-based cleanup. The purified amplicons were then ligated with indexing adapters using Illumina's Nextera XT Index Primers. Following this step, a final cleanup was performed using Aline PCRClean DX beads. The resulting purified libraries were run on an Agilent 4200 Tapestation instrument, with a corresponding Agilent High Sensitivity D1000 ScreenTape assay to visualize the libraries and check that the size of the library matched the expected ~630 bp product. Concentrations obtained from this assay were used to normalize all samples in equimolar ratio. The pool was denatured and loaded onto an Illumina MiSeq instrument, with an Illumina MiSeq V3 600-cycle kit to obtain Paired-End 300 bp reads. The pool was loaded at 10.5 μM, with 50% PhiX spiked in to compensate for low base-diversity. The basecall files were demultiplexed through the BioPolymer Facility's pipeline, and the resulting FASTQ files were used in subsequent analysis. Raw fastq sequences were then quality-filtered and analyzed by following QIIME2 version 2018.11 and DADA2 1.6.0[52-54] Operational Taxonomic Units (OTUs) were picked with 97% sequence similarity. The phylogenetic affiliation of each OTU was aligned to the Greengenes reference database version 13_8 and 99% ID.

Data and Software Availability. 16S rDNA datasets are available through NCBI under accession number PRJNA528994.

Statistical Analyses. Statistical analysis tests were performed with Prism V8.0.2 (GraphPad).

REFERENCES

1. H. Shapiro, et al. *J Exp Med* 215, 383-396 (2018).
2. J. M. Ridlon et al. *J Lipid Res* 47, 241-259 (2006).
3. A. S. Devlin et al. *Nat Chem Biol* 11, 685-690 (2015).
4. J. P. Hamilton et al. *Am J Physiol Gastrointest Liver Physiol* 293, G256-263 (2007).
5. H. Bernstein et al. *World J Gastroenterol* 15, 3329-3340 (2009).
6. J. I Barrasa et al. *Toxicol In Vitro* 27, 964-977 (2013).
7. C. G. Buffie et al. *Nature* 517, 205-208 (2015).
8. H. Duboc et al. *Gut* 62, 531-539 (2013).
9. P. Martinez-Moya et al. *Int Immunopharmacol* 15, 372-380 (2013).
10. F. G. Schaap et al. *Nat Rev Gastroenterol Hepatol* 11, 55-67 (2014).
11. C. Guo et al. *Immunity* 45, 944 (2016).
12. C. Ma et al. *Science* 360, (2018).
13. W. Cao et al. *Immunity* 47, 1182-1196 e1110 (2017).
14. J. R. Huh et al. *Nature* 472, 486-490 (2011).
15. L. Jin et al. *Mol Endocrinol* 24, 923-929 (2010).
16. F. R. Santori et al. *Cell Metab* 21, 286-297 (2015).
17. P. Soroosh et al. *Proc Natl Acad Sci USA* 111, 12163-12168 (2014).
18. E. Esplugues et al. *Nature* 475, 514-518 (2011).
19. J. R. Huh, et al. *Eur J Immunol* 42, 2232-2237 (2012).
20. Y. Feng et al. *Cell* 158, 749-763 (2014).
21. Y. Feng et al. *Nature* 528, 132-136 (2015).
22. Y. Zheng et al. *Nature* 463, 808-812 (2010).
23. R. M. Samstein et al. *Cell* 150, 29-38 (2012).
24. N. Arpaia et al. *Nature* 504, 451-455 (2013).
25. S. Z. Josefowicz et al. *Nature* 482, 395-399 (2012).
26. S. M. Schlenner et al. *J Exp Med* 209, 1529-1535 (2012).
27. M. Makishima et al. *Science* 296, 1313-1316 (2002).
28. R. Nanduri et al. *J Biol Chem* 290, 12222-12236 (2015).
29. L. E. Jeffery et al. *Journal of immunology* 183, 5458-5467 (2009).
30. S. Gorman et al. *Journal of immunology* 179, 6273-6283 (2007).
31. S. W. Kang et al. *Journal of immunology* 188, 5276-5282 (2012).
32. J P. Etchegaray et al. *Trends Immunol* 33, 168-173 (2012).
34. M. D. Buck et al. *J Exp Med* 212, 1345-1360 (2015).
35. V. A. Gerriets et al. *The Journal of clinical investigation* 125, 194-207 (2015).
36. T. Xu et al. *Nature* 548, 228-233 (2017).
37. D. Zhang et al. *Nat Med* 23, 1036-1045 (2017).
38. M. D. Buck et al. *Cell* 166, 63-76 (2016).
39. A. Angelin et al. *Cell Metab* 25, 1282-1293 e1287 (2017).
40. II Ivanovet al. *Cell* 139, 485-498 (2009).
41. N. Gagliani et al. *Nature* 523, 221-225 (2015).
42. M. Trauner et al. *N Engl J Med* 339, 1217-1227 (1998).
43. P. Vavassori et al. *Journal of immunology* 183, 6251-6261 (2009).
44. T. W. Pols et al. *Cell Metab* 14, 747-757 (2011).
45. G. Kakiyama et al. *Journal of lipid research* 55, 978-990 (2014).
46. K. Sakai et al. *Microbiology and immunology* 24, 187-196 (1980).

What is claimed is:

1. A method for promoting differentiation of T regulatory (Treg) lymphocytes and/or suppressing inflammatory Th17 cells, wherein the method comprises contacting naive CD4+ T lymphocytes with an effective amount of a compound having the following structure

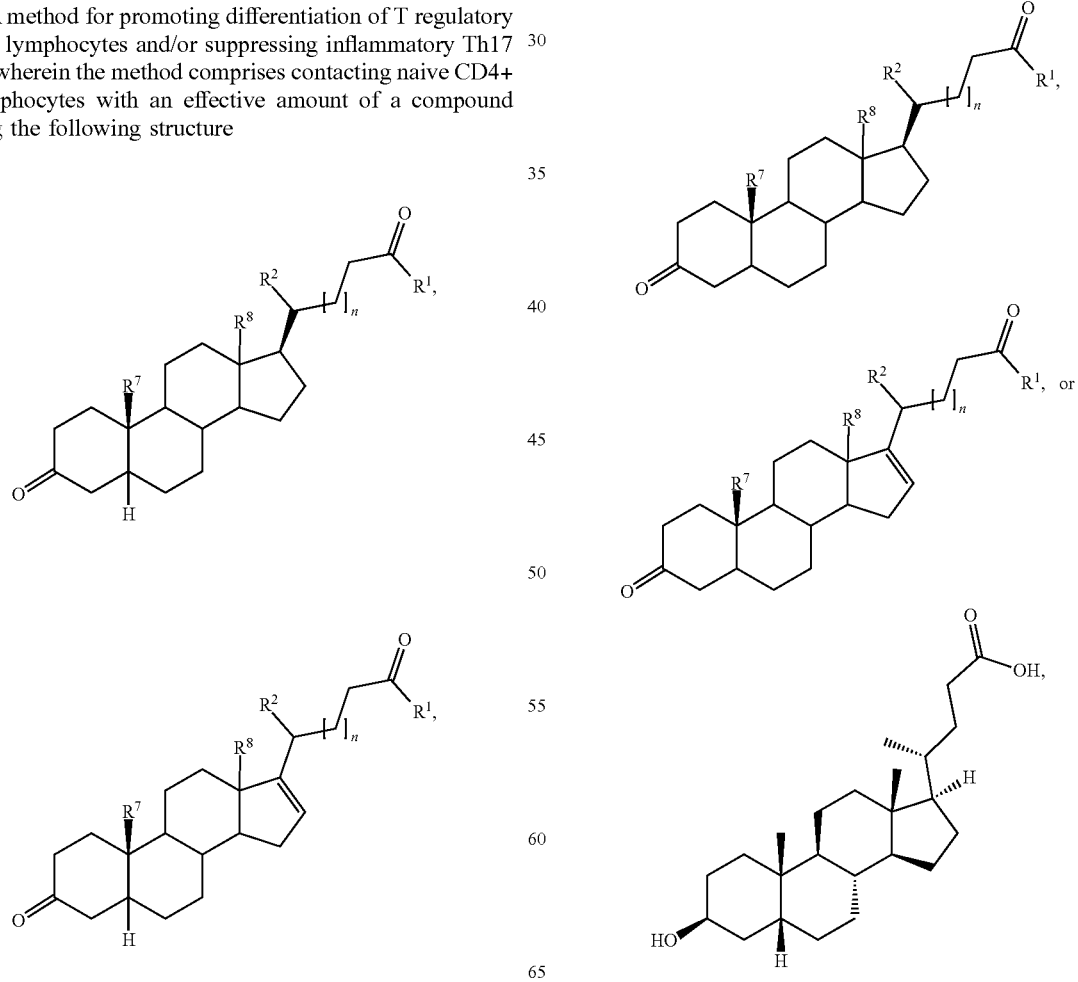

wherein:
R¹ is substituted or unsubstituted alkyl, substituted or unsubstituted hydroxyl, or substituted or unsubstituted amino;
R² is H, alkyl, or substituted or unsubstituted cycloalkyl;
R⁷ is H or substituted or unsubstituted alkyl;
R⁸ is H or substituted or unsubstituted alkyl;
and n is independently 0, 1, 2, 3, 4, 5, or 6;
or a pharmaceutically acceptable salt, solvate, hydrate, prodrug, or stereoisomer, thereof, or a combination thereof.

2. The method according to claim 1, wherein the compound has the following structure:

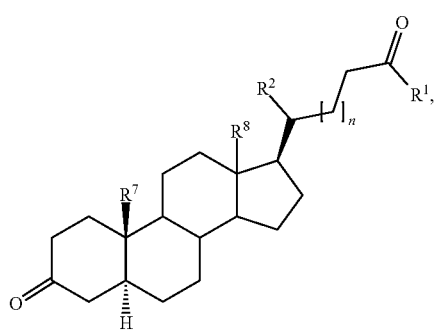

Xc

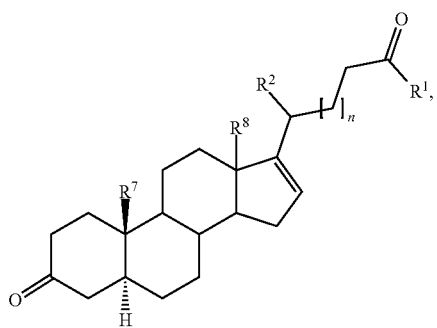

Xd

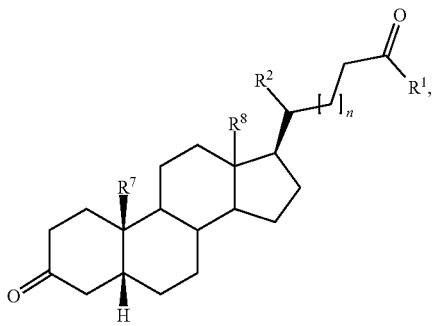

Xlc

Xld and wherein R¹, R², R⁷, R⁸, and n are as in claim 1; or a pharmaceutically acceptable salt, solvate, hydrate, prodrug, or stereoisomer, thereof, or a combination thereof.

3. The method according to claim 1, wherein R² is H, Me, Et, n-Pr, i-Pr, n-Bu, i-Bu, sec-Bu, t-Bu, substituted alkyl, or cycloalkyl and R⁸ is methyl.

4. A method for promoting differentiation of T regulatory (Treg) lymphocytes, wherein the method comprises contacting naive CD4+ T lymphocytes with an effective amount of a compound, wherein the compound according to formula I is allo-lithocholic acid (alloLCA) or iso-allo-lithocholic acid (iso-alloLCA).

5. The method of claim 1, wherein the compound is 3-oxoLCA.

* * * * *

SEQUENCE LISTING

<160> NUMBER OF SEQ ID NOS: 22

<210> SEQ ID NO 1

```
<211> LENGTH: 20
<212> TYPE: DNA
<213> ORGANISM: Artificial Sequence
<220> FEATURE:
<223> OTHER INFORMATION: Primer

<400> SEQUENCE: 1
actggggtct tctccctcaa                                                    20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cgtgggaagg tgcagagtag                                                    20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
cgccaccagt tcgccatgga                                                    20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tacagcccgg ggagcatcgt                                                    20

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
taatgtggca gtttcccaca agcc                                               24

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
aatacctctc tgccactttc gcca                                               24

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
```

-continued

```
agactgtctg gaacaaccta gcct                                          24

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
tggaggtaca gagaggttaa gagcct                                        26

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
atctggccaa gttcaggttg tgac                                          24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
gggcgttcct gtttgactgt ttct                                          24

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
tctccaggct tcagagattc aagg                                          24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
acagtgggat gaggatacat ggct                                          24

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ctgcatcgta gccaccagta                                               20

<210> SEQ ID NO 14
<211> LENGTH: 19
<212> TYPE: DNA
```

<213> ORGANISM: Artificial Sequence
<220> FEATURE:
<223> OTHER INFORMATION: Primer

<400> SEQUENCE: 14
aactattgcc atggcttcc                                                19

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ttaccttgac gggaaagccg agta                                          24

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
ttcgggagct ctcttgagtc acc                                           23

<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
gacgctgagg catgagagca t                                             21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
gacggcacga attgttattc a                                             21

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
actcctacgg gaggcagcag t                                             21

<210> SEQ ID NO 20
<211> LENGTH: 18
<212> TYPE: DNA
<213> ORGANISM: Artificial Sequence
<220> FEATURE:
<223> OTHER INFORMATION: Primer

<400> SEQUENCE: 20
attaccgcgg ctgctggc                                                 18

```
<210> SEQ ID NO 21
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (42)..(42)
<223> OTHER INFORMATION: n is a, c, g, or t

<400> SEQUENCE: 21
tcgtcggcag cgtcagatgt gtataagaga cagcctacgg gnggcwgcag         50

<210> SEQ ID NO 22
<211> LENGTH: 55
<212> TYPE: DNA
<213> ORGANISM: Artificial Sequence
<220> FEATURE:
<223> OTHER INFORMATION: Primer

<400> SEQUENCE: 22
gtctcgtggg ctcggagatg tgtataagag acaggactac hvgggtatct aatcc    55
```